(12) United States Patent
Srinivasan et al.

(10) Patent No.: US 9,795,662 B2
(45) Date of Patent: Oct. 24, 2017

(54) VACCINE COMPRISING AMA1 AND RON2

(71) Applicant: The United States of America, as represented by the Secretary, Department of Health and Human Services, Washington, DC (US)

(72) Inventors: Prakash Srinivasan, Germantown, MD (US); Louis Howard Miller, Cabin John, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/902,117

(22) PCT Filed: Jul. 1, 2014

(86) PCT No.: PCT/US2014/045065
§ 371 (c)(1),
(2) Date: Dec. 30, 2015

(87) PCT Pub. No.: WO2015/002959
PCT Pub. Date: Jan. 8, 2015

(65) Prior Publication Data
US 2016/0158332 A1 Jun. 9, 2016

Related U.S. Application Data

(60) Provisional application No. 61/841,479, filed on Jul. 1, 2013.

(51) Int. Cl.
| | | |
|---|---|---|
| *A61K 45/06* | (2006.01) | |
| *A61K 39/015* | (2006.01) | |
| *C07K 14/445* | (2006.01) | |
| *C07K 16/20* | (2006.01) | |
| *A61K 39/00* | (2006.01) | |

(52) U.S. Cl.
CPC ............ *A61K 39/015* (2013.01); *A61K 45/06* (2013.01); *C07K 14/445* (2013.01); *C07K 16/205* (2013.01); *A61K 2039/55566* (2013.01); *A61K 2300/00* (2013.01); *C07K 2317/10* (2013.01); *C07K 2317/21* (2013.01); *C07K 2317/76* (2013.01); *C07K 2319/00* (2013.01)

(58) Field of Classification Search
None
See application file for complete search history.

(56) References Cited

FOREIGN PATENT DOCUMENTS

| EP | 2520585 | 11/2012 |
|---|---|---|
| WO | WO 02/077195 A2 | 10/2002 |

OTHER PUBLICATIONS

Cruse et al., Illustrated Dict. of Immunology, 2nd ed., CRC Press, 2003, p. 46.*
Cao et al. (2009) Parasitology International 58:29-35 "Rhoptry neck protein RON2 forms a complex with microneme protein AMA1 in *Plasmodium falciparum* merozoites".
Lamarque et al. (2011) PLoS Pathogens 7(2):1-14 "The RON2-AMA1 Interaction is a Critical Step in Moving Junction-Dependent Invasion by Apicomplexan Parasites".
Mahamadou et al. (2011) N. Engl. J. Med. 365(11):1004-1013 "A Field Trial to Assess a Blood-Stage Malaria Vaccine".
Srinivasan et al. (2011) PNAS 108(32):13275-13280 "Binding of *Plasmodium* merozoite proteins RON2 and AMA1 triggers commitment to invasion".
Srinivasan et al. (2013) Nature Communications 4:1-9 "Disrupting malaria parasite AMA1-RON2 interaction with a small molecule prevents erythrocyte invasion".
Srinivasan et al. (2014) PNAS 111(28):10311-10316 "Immunization with a functional protein complex required for erythrocyte invasion protects against lethal malaria".
Thera et al. (2011) N. Engl. J. Med. 365(11):1004-13 "A Field Trial to Assess a Blood-Stage Malaria Vaccine".
Tonkin et al. (2011) Science 333:1-22 "Supporting Online Material for 'Host Cell Invasion by Apicomplexan Parasites: Insights from the Co-Structure of AMA1 with a RON2 Peptide'".
Tonkin et al. (2011) Science 333:463-467 "Host Cell Invasion by Apicomplexan Parasites: Insights from the Co-Structure of AMA1 with a RON2 Peptide".
Tyler et al. (2011) 7(2):1-12 "The C-Terminus of Toxoplasma RON2 Provides the Crucial Link between AMA1 and the Host-Associated Invasion Complex".

* cited by examiner

*Primary Examiner* — Brian J Gangle
(74) *Attorney, Agent, or Firm* — Swanson & Bratschun, L.L.C.

(57) ABSTRACT

Disclosed is a vaccine comprising an immunogenic composition comprising a complex of AMA1 and RON2 (or a fragment thereof), which elicits an immune response to a *Plasmodium* species in a subject upon administration. The resulting immune response is sufficient to impede or prevent infection by a *Plasmodium* species.

19 Claims, 10 Drawing Sheets

```
           Loop Ib         Loop Ic           Loop Id                            Loop Ie              Loop If
       166           177 183     191     195                   211       224               235    262           276
D10  ..LTPVATGNQYLK...FPPTEPLMS...LDEMRHFYKDNKYVKNL...MIPDNDKNSNYKY...YCNKDESKRNSMFCF...
3D7  ..LTPVATGNQYLK...FPPTEPLMS...LDEMRHFYKDNKYVKNL...MIPDNDKNSNYKY...YCNKDESKRNSMFCF...
DD2  ..LTPVATGNQYLK...FPPTEPLMS...LDDMRLLYKDNEDVKNL...MNPDNDKNSNYKY...YCNKDESKRNSMFCF...
HP47 ..LTPVATENQDLK...FPPTEPLMS...LDDMRRFYKDNKYVKNL...MNPDNDKNSNYKY...YCNKDESKRNSMFCF...
HB3  ..LTPVATENQDLK...FPPTEPLIS...LDQMRHLYKDNEYVKNL...MNPDKDENSNYKY...YCNKDESKRNSMFCF...
CAMP ..LKPVATGNQDLK...FPPTEPLIS...LNGMRDFYKNNEYVKNL...MNPDNDKNSNYKY...YCNKDESKRNSMFCF...
FVO  ..LTPVATGNQDLK...FPPTEPLIS...LNGMRDFYKNNEYVKNL...MNPDNDKNSNYKY...YCNKDQSKRNSMFCF...
7G8  ..LTPVATGNQDLK...FPPTKPLIS...LDHMRDFYKNNEYVKNL...MNPDNDKNSNYKY...YCNKDESKRNSMFCF...
HP22 ..LKPVATGNQDLK...FPPTKPLIS...LDDMRDFYKNNEYVKNL...MNPDNDKNSNYKY...YCNKDQSKRNSMFCF...
M24  ..LTPVATENQDLK...FPPTEPLMS...LDQMRDFYKNNEYVKNL...MNPDNDENSNYKY...YCNKDQSKRNSMFCF...
       * ****  *  *    ****.** *    * .* * *:* ***    * *:* :*****    **** ******:*
```

Fig. 8

| | |
|---|---|
| PyRON2L: | KLH - cDITQHATDIGMGPSTSCYTSLLPPPKSICIQQTVKTVLTNSTLASMK-NH2 |
| PyRON2L: | Biotin - Ahx - DITQHATDIGMGPSTSCYTSLLPPPKSICIQQTVKTVLTNSTLASMK-NH2 |
| Pf3D7RON2L: | KLH - cDITQQAKDIGAGPVASCFTTRMSPPQQICLNSVVNTALSTSTQSAMK-NH2 |
| Pf3D7RON2L: | Biotin - Ahx - DITQQAKDIGAGPVASCFTTRMSPPQQICLNSVVNTALSTSTQSAMK-NH2 |
| Pf3D7_DIa: | Biotin - Ahx - LGEDAEVAGTQYRLPS-NH2 |
| Pf3D7_DIb: | Biotin - Ahx - ENSNTTFLTPVATGNQYLKDGGFA-NH2 |
| Pf3D7_DId: | Biotin - Ahx - TLDEMRHFYKDNKYVK-NH2 |
| Pf3D7_DIe: | Biotin - Ahx - GNMIPDNDKNSNYK-NH2 |
| Pf3D7_DIf: | Biotin - Ahx - RYCNKDESKRNSMCFR-NH2 |
| Pf3D7_DIi: | Biotin - Ahx - SDQPKQYEQHLTDYEKIKEGFKNKNASMIKSAFLPTGAFKADRYKSH-NH2 |
| Pf3D7_DId+e: | Biotin - Ahx - SPMTLDEMRHFYKDNKYVKNLDELTLCSRHAGNMIPDNDKNSNYKYPAVYDDKDKKCH-NH2 |
| Pf3D7_DId+c=d: | Biotin - Ahx - SNTTFLTPVATGNQYLKDGGFAFPPTEPLMSPTLDEMRHFYKDNKYVKNL-NH2 |

Fig. 10

VACCINE COMPRISING AMA1 AND RON2

RELATED APPLICATION DATA

This application is a 35 U.S.C. §371 national phase application of PCT/US2014/045065, filed on Jul. 1, 2014 entitled "VACCINE COMPRISING AMA1 AND RON2" which application claims the priority benefit of U.S. Provisional Application No, 61/841,479, filed on Jul. 1, 2013, entitled "VACCINE COMPRISING AMA1 AND RON2", all of which are incorporated herein by reference, in their entirety. Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

STATEMENT OF GOVERNMENT INTEREST

This invention was made with government support; the government has certain rights in this invention.

SEQUENCE LISTING

Incorporated by reference herein in its entirety is the Sequence Listing entitled "Sequence_Listing_ST25.txt", created Jun. 30, 2014, size of 107 kilobytes.

BACKGROUND

*Plasmodium* is the causative agent of malaria, one of the world's deadliest parasitic diseases. Malaria affects over 300 million people worldwide, causing more than 1 million deaths annually, particularly in young children and pregnant women in sub-Saharan Africa. Currently, there is no vaccine available, and there is widespread resistance to common anti-malarial drugs. RTS,S, a leading vaccine candidate which targets the initial infection of the liver, achieved only partial efficacy (Olotu, et al. 2013 *N Engl J Med* 368(12): 1111-1120). However, clinical manifestations of the disease are caused by the blood-stage parasites. These disease-causing forms of the parasite primarily reside within the red blood cells (RBC), which, upon maturation (schizont), releases merozoites, the invasive form of *Plasmodium* that invades new RBCs. Therefore, vaccines targeting the erythrocytic forms of the parasite are desirable for efficient disease control measures.

Apicomplexan parasites have specialized secretory organelles (rhoptries and micronemes) that release their contents during host cell invasion. The micronemes possess the protein apical membrane antigen 1 (AMA1). AMA1 is an essential merozoite surface protein and was previously considered one of the leading blood-stage vaccine candidates (Stowers, et al. 2002 *Infect Immun* 70(12):6961-6967 and Dutta, et al. (2009) *PLoS One* 4(12):e8138). Despite the vaccines' ability to elicit high-titred AMA1-specific antibodies, Phase 2 clinical trials showed only weak efficacy (http://www.ncbi.nlm.nih.gov/pubmed/21916638, Mahamadou, et al. 2011 *New England J Med* 365(11):1004-13), even against homologous parasite (Spring, et al. 2009 *PLoS One* 4(4):e5254, Ouattara, et al. 2010 *Malar J* 9:175 and Thera, et al. 2011 *N Engl J Med* 365(11):1004-1013). Recent efforts to cover the polymorphism in AMA1 demonstrated that combining 4-5 different AMA1 alleles could overcome the strain-specific barrier in vitro (Miura, et al. 2013 *Infect Immun* 81(5):1491-1501, Dutta, et al. 2013 *PLoS Pathog* 9(12):e1003840 and Remarque, et al. 2008 *Infect Immun* 76(6):2660-2670).

The rhoptry neck sub-compartment possesses a distinct protein repertoire, including rhoptry neck protein (RON2).

SUMMARY

The discordance between failure to protect humans in vivo and ability to block vaccine-type parasite invasion in vitro (Spring, et al. 2009 *PLoS One* 4(4):e5254) underscores the need to improve AMA1 vaccine efficacy against homologous parasites. Interaction between AMA1 and another parasite protein RON2 is shown to be essential for successful invasion of RBCs (Lamarque, et al. 2011 *PLoS Pathog* 7(2):e1001276). A small 49-amino acid peptide near the C-terminal of the RON2 protein is sufficient to bind a hydrophobic pocket in AMA1. Small molecules or peptides that block this interaction inhibit merozoite invasion (Srinivasan, et al. 2013 *Nat Commun* 4:2261 and Richard, et al. 2010 *J Biol Chem* 285(19):14815-14822), highlighting the important role of this protein-protein interaction. Crystal structure of the complex revealed that the RON2 peptide (RON2L) binds to a conserved hydrophobic groove in AMA1 resulting in extensive conformational changes in certain loop regions surrounding the groove (Vulliez-Le Normand, et al. 2012 *PLoS Pathog* 8(6):e1002755 and Tonkin, et al. 2011 *Science* 333(6041):463-467). Antibodies that bind in or near the hydrophobic groove block parasite invasion by inhibiting the binding of RON2 (Dutta, et al. 2013 *PLoS Pathog* 9(12):e1003840 and Srinivasan, et al. 2011 *Proc Natl Acad Sci USA* 108(32):13275-13280). It is further shown that a very high concentration of antibodies against the RON2 peptide is required to inhibit merozoite invasion (Srinivasan, et al. 2011 *PNAS* 10:1073). Simply adding anti-AMA1 and anti-RON2 peptide antibodies together does not improve inhibition of invasion.

Described herein is a novel approach based on vaccination with an AMA1-RON2 complex that provides complete protection against lethal *Plasmodium* challenge in an animal model. A highly virulent *P. yoelli* YM (PyYM) mouse model was used. In marked contrast, animals immunized with the two antigens separately are not protected. Indeed, immunization with a functional complex of RON2 peptide (RON2L) induces antibody-mediated, complete protection against lethal *P. yoelli* challenge. The data shows that protection of animals is based on antibodies generated against the complex. Significantly, IgG from mice immunized with the complex transferred protection. Furthermore, IgG from PfAMA1-RON2 immunized animals have enhanced invasion inhibition compared to IgG elicited by AMA1 alone, as passive transfer of IgG but not T cells from AMA1-RON2L vaccinated animals controlled parasitemia.

Protection may be mediated by antibodies recognizing new inhibitory epitopes of AMA1 and/or the AMA1/RON2 peptide complex exposed by the binding of RON2 to AMA1. Interestingly, the qualitative increase in efficacy appears to be, in part, due to a switch in the proportion of antibodies targeting the RON2 binding site in AMA1. This indicates that the complex functions as an antigen exposing unique, inhibitory epitopes that may be distinctive from the two antigens by themselves. Because AMA1 and RON2 are critical for the *Plasmodium* parasite's invasion of the host cell, targeting them by raising a host immune response to a complex of the two proteins should block infection. These results suggest that a multi-allele AMA1 (to overcome polymorphisms) in complex with RON2L should be effective in protecting against all *P. falciparum* parasites.

It is demonstrated herein that the human parasite Pf3D7 AMA1-RON2L complex induces qualitatively higher growth inhibitory antibodies than AMA1 alone in vitro assays. Surprisingly, the results indicate that the increase in inhibitory antibodies generated by the complex may, in part, be due to a switch in the proportion of antibodies against the loops surrounding the hydrophobic groove with which RON2 interacts. The data suggest that a vaccine comprising a multi-allele AMA1 in complex with RON2L may be more efficacious compared to AMA1 alone in targeting both homologous and heterologous parasites.

The invention encompasses treatment and/or prophylaxis of *Plasmodium* infection/malaria (used interchangeably herein) by administration of vaccines disclosed herein. In some embodiments, such vaccines are administered to a subject suffering from malaria or susceptible to *Plasmodium* infection. In some embodiments, a subject is considered to be suffering from malaria, if the subject is displaying one or more symptoms commonly associated with therewith. In some embodiments, the subject is known or believed to have been exposed to at least one *Plasmodium* species. In some embodiments, a subject is considered to be susceptible to *Plasmodium* infection, if the subject is known or believed to have been exposed to a *Plasmodium* species. In some embodiments, a subject is known or believed to have been exposed to a *Plasmodium* species, if the subject has been in contact with other individuals known or suspected to have been infected with the same, and/or if the subject is or has been present in a location in which malaria is known or thought to be prevalent. Vaccines disclosed herein may be administered prior to or after development of one or more symptoms of *Plasmodium* infection/malaria.

Thus, in one aspect, the invention provides a vaccine comprising: i) an immunogenic composition comprising a complex of AMA1 and RON2; and ii) at least one adjuvant and/or at least one physiologically acceptable carrier.

In another aspect, the invention provides a vaccine comprising: i) an immunogenic composition comprising a complex of: a) AMA1 or a fragment thereof; and b) RON2 or a fragment thereof; and ii) at least one adjuvant and/or at least one physiologically acceptable carrier. The full-length RON2 protein is 2189 amino acids (aa). Identified herein is one 49 amino acid region sufficient to bind AMA1 and elicit a protective immune response. A shorter fragment within that 49 aa region or another fragment of the full-length protein may likewise exhibit AMA1 binding capability and elicit a protective immune response. Thus, full-length RON2, RON2 peptide, peptide derived from RON2, RON2L, and a fragment of RON2 (the latter four "terms/phrases" being used interchangeably) are contemplated in the vaccines, methods, and articles of manufacture disclosed herein.

In still another aspect, the invention provides a vaccine comprising: i) an immunogenic composition comprising a fusion protein complex of AMA1 and RON2 (or a fragment thereof); and ii) at least one adjuvant and/or at least one physiologically acceptable carrier. In the instant aspect, it would not be necessary to prepare the individual components and then mix them to form a complex. Rather, a fusion protein is created by joining the genes coding for the separate proteins. Translation of the fusion gene then results in a single polypeptide.

In one embodiment of a vaccine according to the invention, the immunogenic composition elicits an immune response to a *Plasmodium* species in a subject upon administration to the subject. In another embodiment, the immune response is sufficient to impede or prevent infection by a *Plasmodium* species.

In another embodiment of a vaccine according to the invention, the vaccine is for the treatment of or protection from erythrocytic (blood stage) and/or pre-erythrocytic (liver stage) malaria infection in a subject. In another embodiment of a vaccine according to the invention, the vaccine is for the treatment of or protection from erythrocytic malaria infection in a subject. In another embodiment of a vaccine according to the invention, the vaccine is for the treatment of or protection from pre-erythrocytic malaria infection in a subject. In still another embodiment, the treatment manifests itself in the subject as the parasitemia being under control and/or the infection being cleared.

In one embodiment of a vaccine according to the invention, the *Plasmodium* species is selected from the group consisting of *Plasmodium falciparum, Plasmodium knowlesi, Plasmodium vivax, Plasmodium yoelii, Plasmodium malariae, Plasmodium ovale, Plasmodium brasilianum, Plasmodium cynomulgi, Plasmodium inui, Plasmodium rhodiani, Plasmodium schwetzi, Plasmodium semiovale*, and *Plasmodium simium.*

In another embodiment of a vaccine according to the invention, the vaccine further comprises an active agent. The active agent may, without limitation, be an antibiotic, and antigen, or an antibody.

In another aspect, the invention provides a method of protecting a subject from erythrocytic (blood stage) malaria infection comprising administering a vaccine as disclosed herein to the subject in an amount effective to stimulate an immune response, thus protecting the subject from erythrocytic (blood stage) malaria infection.

In another aspect, the invention provides a method of protecting a subject from pre-erythrocytic (liver stage) malaria infection comprising administering a vaccine as disclosed herein to the subject in an amount effective to stimulate an immune response, thus protecting the subject from pre-erythrocytic (liver stage) malaria infection.

In another aspect, the invention provides a method of protecting a subject from both erythrocytic and pre-erythrocytic malaria infection comprising administering a vaccine as disclosed herein to the subject in an amount effective to stimulate an immune response, thus protecting the subject from both pre-erythrocytic and erythrocytic malaria infection. The degree of protection from each may vary.

In another aspect, the invention provides a method of protecting a subject from infection by a *Plasmodium* species comprising administering a vaccine as disclosed herein to the subject in an amount effective to stimulate an immune response, thus protecting the subject from infection with the *Plasmodium* species.

In one embodiment of a method according to the invention, the vaccine is administered orally or parenterally.

In another embodiment of a method according to the invention, the vaccine is administered with another active agent. In yet another embodiment, the active agent is an antibiotic, antigen, or antibody.

In another aspect, the invention provides a method for vaccinating a subject against a *Plasmodium* species comprising administering to the subject an effective amount of a vaccine as disclosed herein.

In yet another aspect, the invention provides a method for generating protective antibodies in a subject against a *Plasmodium* species comprising administering to the subject an effective amount of a vaccine as disclosed herein.

In still another aspect, the invention provides a method for producing an immune response against a *Plasmodium* species in a subject comprising administering a vaccine as disclosed herein to the subject in an amount effective to produce an immune response against the *Plasmodium* species.

In one embodiment of a method according to the invention, the *Plasmodium* species is selected from the group consisting of *Plasmodium falciparum, Plasmodium knowlesi, Plasmodium vivax, Plasmodium yoelii, Plasmodium malariae, Plasmodium ovale, Plasmodium brasilianum, Plasmodium cynomulgi, Plasmodium inui, Plasmodium rhodiani, Plasmodium schwetzi, Plasmodium semiovale,* and *Plasmodium simium*.

In one aspect, the invention provides an article of manufacture comprising a closed, pathogen-impermeable container and a sterile vaccine preparation enclosed within said container, wherein said vaccine preparation comprises a vaccine as disclosed herein.

Other aspects of the invention are described in or are obvious from the following disclosure and are within the ambit of the invention.

BRIEF DESCRIPTION OF THE DRAWINGS

The following Detailed Description, given by way of Examples, but not intended to limit the invention to specific embodiments described, may be understood in conjunction with the accompanying figures, in which:

(FIG. 3A) Five mice per group were immunized with AMA1, RON2L-KLH or AMA1-RON2L complex and challenged with $10^4$ infected RBCs (iRBCs) intravenously. Five mice immunized with buffer in Freund's adjuvant were used as controls. Error bars indicate mean±sem. (FIG. 3B) Kaplan-Meir curve of the overall survival of animals in FIG. 3A. (FIG. 3C) ELISA titers of antibody response against AMA1 and RON2L from sera of mice from FIG. 3a. Sera were used at 1:8000 and 1:2000 dilutions for AMA1 and RON2L, respectively. Error bars indicate mean±sem at $O.D_{405}$. (FIG. 3D) In silico homology model of PyAMA1-PyRON2L complex based on PfAMA1-PfRON2 complex structure. Arrows indicate the two cysteines in the PyRON2L peptide (FIG. 3E) Mutation of Cys 1856 and 1868 to Ala abolishes RON2L binding to PyAMA1. (FIG. 3F) Mutating the two cysteines to alanines (c/a) in the RON2L peptide required for binding to AMA1 abrogates complex driven protection in mice. Five mice per group were challenged with $10^5$ iRBCs. Error bars indicate mean±sem. (FIG. 3G) Protection requires vaccination with the AMA1-RON2L complex as immunizing animals with the two antigens in separate sites (AMA1+RON2L) does not protect. Five mice per group for control and AMA1-RON2L and four mice for AMA1+RON2L were challenged with $10^5$ iRBCs. Error bars indicate mean±sem. (FIG. 3H) Passive transfer of IgG from mice immunized with the AMA1-RON2L complex controls parasitemia. 400 μg of IgG from either control (PBS-Freund's adjuvant immunized mice) or AMA1-RON2L immunized mice were passively transferred on day −1, 0 and +1 and challenged on day 0 with $10^5$ iRBCs using 5 mice per group. Error bars indicate mean±sem. (FIG. 3I) Kaplan-Meir curve of the overall survival of animals in FIG. 3H.

(FIG. 4A) IgG purified from rats immunized with Pf3D7AMA1-RON2L complex induces higher growth inhibition compared to IgG from PfAMA1 immunized rats (n=4). 2 mg/mL IgG was used in the inhibition assay and results are mean±sem of pooled data from two independent experiments. (FIG. 4B) PfAMA1 and PfAMA1-RON2L complex induces similar levels of anti-AMA1 antibodies. ELISA units represent the AMA1-specific antibody titer in purified IgG (2 mg/mL) and serum from four immunized rats used in FIG. 4A. Error bars indicate mean±sem. (FIG. 4C) GIA was measured using increasing concentrations of IgG from AMA1, RON2L and AMA1-RON2L groups. Data shown are the mean parasite inhibition from an assay performed in duplicate. The contribution of anti-RON2L antibody towards the increased GIA observed in the AMA1-RON2L group was analyzed by mixing 1 mg/mL each of anti-RON2L IgG and anti-AMA1 IgG (AMA1+RON2L). Data shown are mean±sem for four rats. (FIG. 4D) Inhibition of invasion is reversed by the addition of recombinant Pf3D7 AMA1 to IgG from PfAMA1 (blue) and PfAMA1-RON2L (red) groups. Data shown are the mean±sem parasite inhibition from two independent experiments performed in duplicate. All four data points are plotted. (FIG. 4E) Binding of biotinylated RON2L peptide to immobilized Pf3D7 AMA1 inhibited by serial dilution of IgG against PfAMA1 (blue) and PfAMA1-RON2L complex (red). The X-axis indicates the amount of total AMA1-specific EU present at each of the dilutions. $EC_{50}$ (50% inhibition of RON2L binding) was measured by plotting a nonlinear fit of the individual data points (*, p=0.018).

(FIG. 5A) View of the loops surrounding the hydrophobic groove in the absence of RON2L. (FIG. 5B) View of the loops in the RON2L-bound form. (FIG. 5C) Overlay of AMA1 loop structures surrounding the hydrophobic groove in the presence (colored) and absence of RON2L (grey). (FIG. 5D) Binding of IgG from AMA1 (blue) and AMA1-

RON2L complex (red) to biotinylated peptides immobilized on streptavidin plates. The X-axis indicates the amount of total AMA1-specific EU present at each of the dilutions. Data are mean±sem (n=4). A representative of 3 independent experiments is shown.

Figure 6:
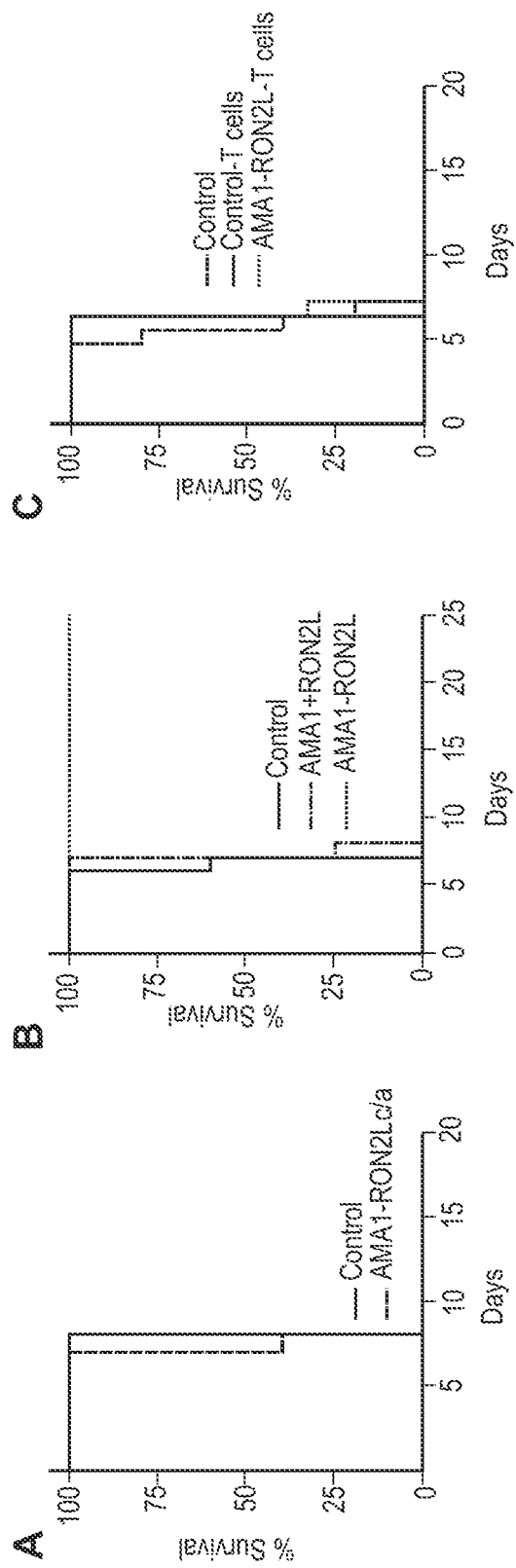

FIG. 6 (i.e., FIGS. 6A-6C, as follows) demonstrates: (FIG. 6A) Kaplan-Meir curve of the overall survival of animals in FIG. 3F. (FIG. 6B) Kaplan-Meir curve of the overall survival of animals in FIG. 3G. (FIG. 6C) T cell transfer does not protect against PyYM challenge. Kaplan-Meir curve of the overall survival of animals after passive transfer of $2 \times 10^6$ T cells from mice immunized with PBS-adjuvant (blue) or mice immunized with PyAMA1-RON2L complex (red) on days −1, 0 and +1. Mice that received no cells were used as infection controls (black). Five mice per group were used and were challenged intravenously with $10^5$ PyYM parasites on day 0.

Figure 7:
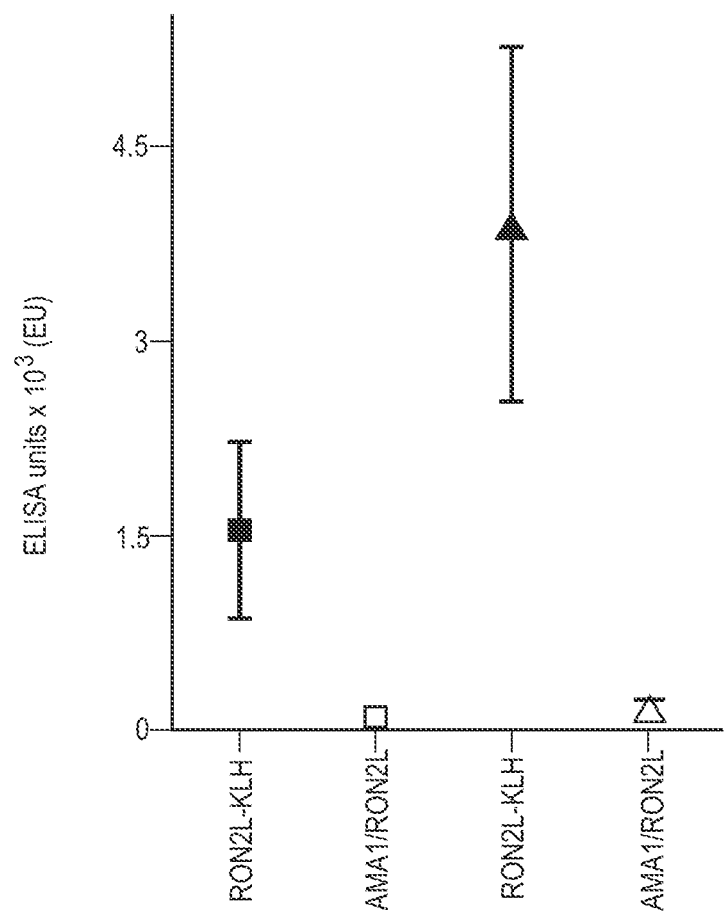

FIG. 7 demonstrates: anti-PfRON2L antibody titers induced by PfRON2L-KLH and PfAMA1-RON2L complex in rats. ELISA units represent the RON2L-specific antibody titer in either purified IgG (2 mg/mL) or serum from four immunized rats used in FIG. 4A. Error bars indicate mean±sem.

FIG. 8 demonstrates: sequence alignment showing polymorphisms in the individual domain I loops surrounding the hydrophobic groove across multiple P. falciparum parasite strains. From the top of the alignment to the bottom, the SEQ ID NOs for the respective sequences are as follows: SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27.

Figure 9:
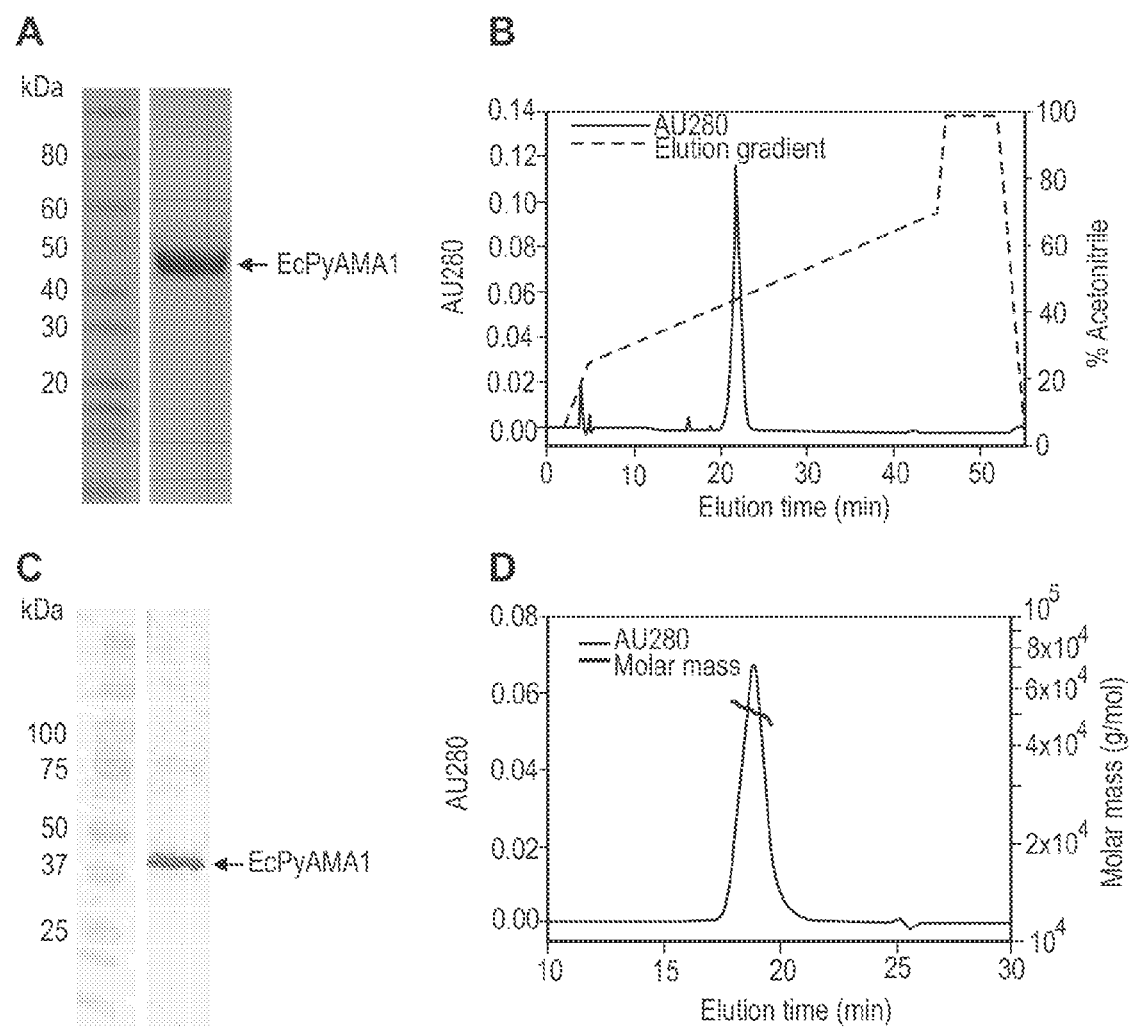

FIG. 9 (i.e., FIGS. 9A-9D, as follows) demonstrates biochemical and biophysical characterization of recombinant EcPyAMA1. Analysis of purified recombinant EcPyAMA1 by (FIG. 9A) Coomassie blue stained SDS-PAGE gel and (FIG. 9B) Western blot with a PyAMA1 specific monoclonal antibody (mAb) 45B1 under non-reduced conditions. Molecular mass markers are shown alongside. (FIG. 9C) Reversed-phase-HPLC analysis showing single peak along with the acetonitrile gradient elution. (FIG. 9D) Analytical size-exclusion chromatography showing single monomeric peak.

FIG. 10 shows: peptide sequences corresponding to PyRON2L, PfRON2L and PfAMA1 domain I and domain II loop regions used herein. Disulfide bridged cysteine residues in the peptides are underlined. All peptides were amidated (NH$_2$) at the C-terminus. From the top sequence to the bottom, the SEQ ID NOs for the respective sequences are as follows: SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, and SEQ ID NO:39.

Figure 11:
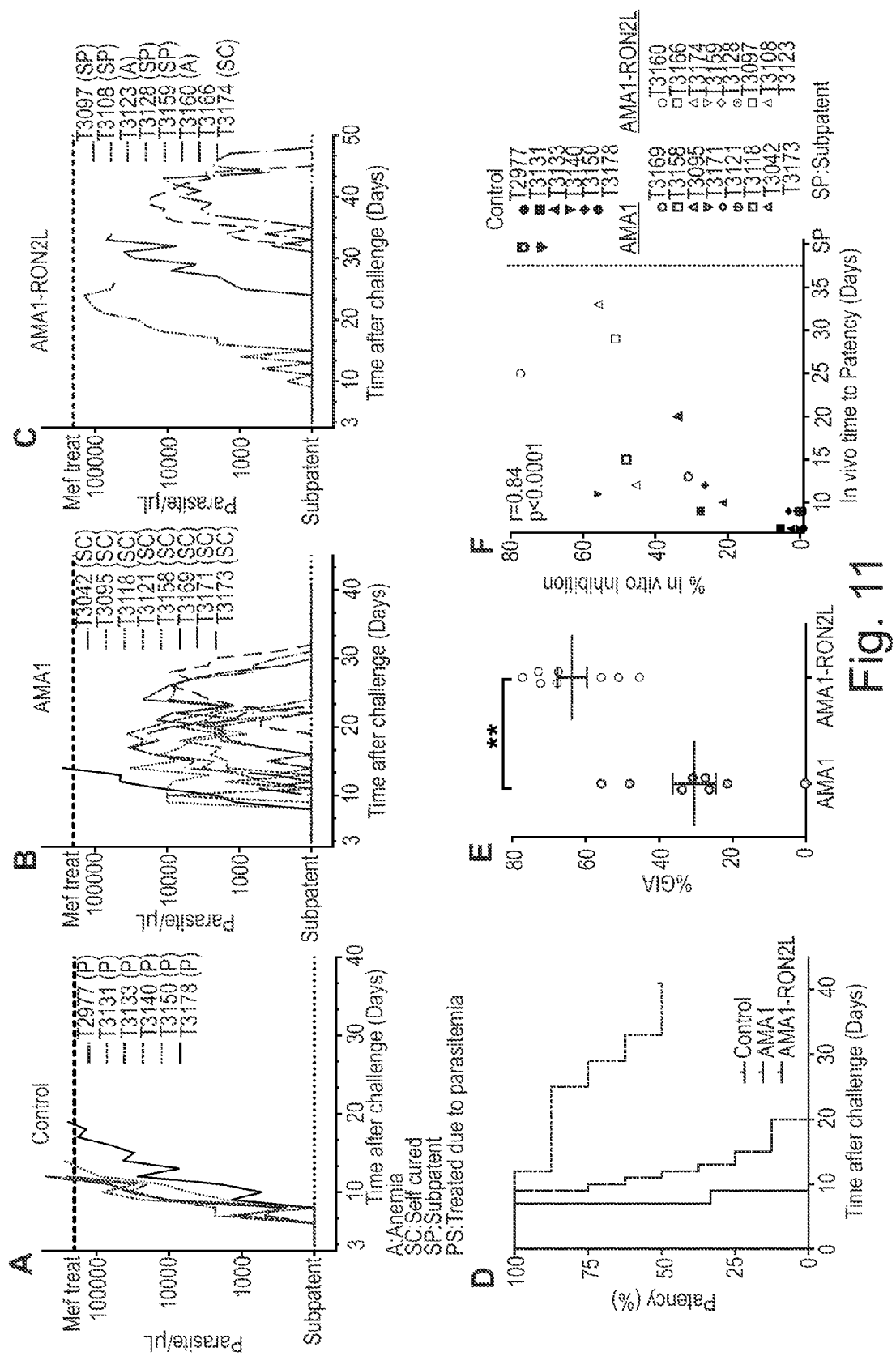

FIG. 11 (i.e., FIGS. 11A-11F, as follows) demonstrates: non-human primate challenge using virulent human malaria parasite P. falciparum. FIGS. 11A-11C: parasitemia of control (FIG. 11A), AMA1 (FIG. 11B), and AMA1-RON2 (FIG. 11C)-vaccinated animals. All control (n=6) and AMA1 (n=8) became infected, but 4/8 animals immunized with AMA1-RON2 complex were sterile-protected, and an additional 3/4 animals had a significantly delayed parasitemia. (FIG. 11D) Time to patency after challenge. (FIG. 11E) IgG purified from the vaccinated animals were tested in an in vitro growth inhibition assay (GIA). AMA1-RON2L-induced IgG inhibited significantly higher than IgG from AMA1 alone at 2.5 mg/mL. (FIG. 11F) Correlation analysis of in vivo protection and in vitro inhibition. AMA1-RON2-immunized animals that were protected correlated well with increased GIA.

DETAILED DESCRIPTION

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

Definitions

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices, and materials are now described.

As used in this application, including the appended claims, the singular forms "a," "an," and "the" include plural references, unless the content clearly dictates otherwise, and are used interchangeably with "at least one" and "one or more." Thus, reference to "a polynucleotide" includes a plurality of polynucleotides or genes, and the like.

As used herein, the term "about" represents an insignificant modification or variation of the numerical value, such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

The terms "subject", "patient", and "individual", as used herein, interchangeably refer to a multicellular animal (including mammals (e.g., humans, non-human primates, murines, ovines, bovines, ruminants, lagomorphs, porcines, caprines, equines, canines, felines, ayes, etc.), avians (e.g., chicken), amphibians (e.g. Xenopus), reptiles, and insects (e.g. Drosophila). "Animal" includes guinea pig, hamster, ferret, chinchilla, mouse and cotton rat.

Reference herein to any numerical range (for example, a dosage range) expressly includes each numerical value (including fractional numbers and whole numbers) encompassed by that range. For example, reference herein to a range of "less than x" (wherein x is a specific number) includes whole numbers x-1, x-2, x-3, x-4, x-5, x-6, etc., and fractional numbers x-0.1, x-0.2, x-0.3, x-0.4, x-0.5, x-0.6, etc. In yet another illustration, reference herein to a range of from "x to y" (wherein x is a specific number, and y is a specific number) includes each whole number of x, x+1, x+2 . . . to y−2, y−1, y, as well as each fractional number, such as x+0.1, x+0.2, x+0.3 . . . to y−0.2, y−0.1. In another example, the term "at least 95%" includes each numerical value (including fractional numbers and whole numbers) from 95% to 100%, including, for example, 95%, 96%, 97%, 98%, 99% and 100%.—the latter will only be kept in and filled in with appropriate numbers if we use any greater than or less than numerical characterization . . . .

The terms "antigen," "immunogen," "antigenic," "immunogenic," "antigenically active," "immunologic", and "immunologically active", as used herein, refer to any substance (including a molecule with one or more epitopes) that is capable of inducing a specific immune response (including eliciting a soluble antibody response) and/or cell-mediated immune response (including eliciting a cytotoxic T-lymphocyte (CTL) response), for example, to a malarial pathogen. The antigen can, in certain embodiments, be a complete protein, portions of proteins, peptides, fusion proteins, glycosylated proteins, and combinations thereof. In the context of the vaccines disclosed herein, one or more antigens (for example, AMA1/RON2 complex) may be provided directly or as part of a recombinant nucleic acid expression system to provide the antigenic complex to trigger an immune response in a subject. The antigen may also be a DNA molecule that produces the antigenic complex in the subject.

In general, "RON2", as used herein, refers to the protein, while "RON2L", as used herein, refers to the peptide sequence (49 amino acids). However, "AMA1/RON2" and "AMA1/RON2L" are used interchangeably herein when referring to the protein complex.

As used herein, the term "protein complex" or "complex" refers to the association of at least AMA1 and RON2. The term "protein complex" or "complex" includes a fusion protein complex. The proteins of the complex may be associated by a variety (including combination) of methods, including, without limitation, functional, stereochemical, conformational, biochemical, or electrostatic association. In another embodiment, a multi-allele AMA1 (to overcome polymorphisms) in complex with RON2L is effective in protecting against both homologous and heterologous parasites.

An "immunogenic composition", as used herein, refers to a composition capable of eliciting an immune response to at least AMA1 or RON2 or AMA1/RON2 complex, when the composition is administered to a subject. The immune response elicited by such a composition comprised in a vaccine according to the invention affects the ability of a *Plasmodium* species to infect a subject immunized with the composition. Preferably, the ability of a *Plasmodium* species to infect an immunized subject is impeded or prevented.

The term "immune response", as used herein, refers to the development in a subject of a secretory and/or humoral and/or cellular immunological response to an antigen. "Humoral" immune response refers to the production of antibodies; "cellular" immune response refers to the activation of T-lymphocytes. An immune response elicited by an immunogenic composition comprised in a vaccine according to the invention may be a protective immune response. In such an embodiment, a protective response is generated in the vaccinated subject. Preferably, a protective immune response protects against subsequent infection by a *Plasmodium* species. The protective immune response may, in another embodiment, eliminate or reduce the level of infection in an infected subject upon vaccination.

An "immunologically effective amount", as used herein, refers to the amount of immunogen that, when administered to a subject, either in a single dose or in a series of doses, is effective for the treatment or prevention of infection by a *Plasmodium* species. This amount may vary depending upon the health and physical condition of the subject to be treated, as well as on the immunogen. Determination of an effective amount of vaccine for administration to a subject is well within the capabilities of those skilled in the art.

The term "polymorphism", as used herein, refers to a polymorphic allele and is discussed in the context of the AMA1 protein. It is also contemplated in the context of the RON2 protein. Polymorphism involves one of two or more variants of a particular amino acid/protein sequence. The most common type of polymorphism involves variation at a single amino acid. Polymorphisms can also involve multiple amino acids at different positions and/or long stretches of amino acids, really, any number of changes in the protein sequence in question, for example, AMA1 or RON2.

An individual referred to as "suffering from" a disease, disorder, and/or condition (e.g., erythrocytic malaria infection) herein has been diagnosed with and/or displays one or more symptoms of the disease, disorder, and/or condition.

As used herein, the term "at risk" for disease (such as erythrocytic malaria infection), refers to a subject (e.g., a human) that is predisposed to contracting the disease and/or expressing one or more symptoms of the disease. Such subjects include those at risk for failing to elicit an immunogenic response to a vaccine against the disease. This predisposition may be genetic (e.g., a particular genetic tendency to expressing one or more symptoms of the disease, such as heritable disorders, the presence of bacterial species blocking antibodies, the presence of reduced levels of bactericidal antibodies, etc.), or due to other factors (e.g., immune suppressive conditions, environmental conditions, exposures to detrimental compounds, including immunogens, present in the environment, etc.). The term subject "at risk" includes subjects "suffering from disease," i.e., a subject that is experiencing the disease. It is not intended that the present invention be limited to any particular signs or symptoms. Thus, it is intended that the present invention encompasses subjects that are experiencing any range of disease, from sub-clinical infection to full-blown disease, wherein the subject exhibits at least one of the indicia (e.g., signs and symptoms) associated with the disease.

Initial manifestations of malaria, common to all malaria species, are similar to flu-like symptoms and can resemble other conditions such as septicemia, gastroenteritis, and viral diseases. The presentation may include headache, fever, shivering, arthralgia (joint pain), vomiting, hemolytic anemia, jaundice, hemoglobinuria, retinal damage, and convulsions. Owing to the non-specific nature of disease presentation, diagnosis of malaria in non-endemic countries requires a high degree of suspicion, which might be elicited by any of the following: recent travel history, splenomegaly (enlarged spleen), fever without localizing signs, thrombocytopenia, and hyperbilirubinemia combined with a normal peripheral blood leukocyte count.

The classic symptom of malaria is paroxysm—a cyclical occurrence of sudden coldness followed by rigor and then fever and sweating, occurring every two days (tertian fever) in *P. vivax* and *P. ovale* infections, and every three days (quartan fever) for *P. malariae*. *P. falciparum* infection can cause recurrent fever every 36-48 hours or a less pronounced and almost continuous fever.

Severe malaria is usually caused by *P. falciparum* (often referred to as *falciparum* malaria). Symptoms of *falciparum* malaria arise 9-30 days after infection (Bartoloni, et al. 2012 *Mediterr J Hematol Infect Dis* 4(1):e2012026). Included among the symptoms of malaria (infection) are complications associated with the disease. Among these is the development of respiratory distress, which occurs in up to 25% of adults and 40% of children with severe *P. falciparum* malaria. Infection with *P. falciparum* may result in cerebral malaria, a form of severe malaria that involves encephalopathy. It is associated with retinal whitening, which may be a useful clinical sign in distinguishing malaria from other causes of fever. Splenomegaly, severe headache, hepatomegaly (enlarged liver), hypoglycemia, and hemoglobinuria with renal failure may occur.

The terms "homologous" and "heterologous", as used herein, refer to polymorphisms within protein, for example, AMA1 alleles among different parasites. Homologous indicates that the vaccine-type allele and the AMA1 sequence in the parasite used for challenge are similar. Heterologous indicates that the vaccine-type allele and the AMA1 sequence in the parasite used for challenge are different.

The methods of protecting and/or vaccinating a subject, as disclosed herein, include treating the subject. The terms "treat," "treatment," or "treating", as used herein, refer to any method used to partially or completely alleviate, ameliorate, relieve, inhibit, prevent, delay onset of, reduce severity of and/or reduce incidence of one or more symptoms or features of a disease, disorder, and/or condition (e.g., erythrocytic malaria infection). Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

As used herein, the terms "immunogenically effective amount," "immunologically effective amount", and "antigenically effective amount" refer to that amount of a molecule that elicits and/or increases production of an immune response (including production of specific antibodies and/or induction of a TCL response) in a host upon vaccination. It is preferred, though not required, that the immunologically-effective (i.e., immunogenically effective) amount is a "protective" amount. The terms "protective" and "therapeutic" amount of a vaccine refer to an amount of the vaccine that prevents, delays, reduces, palliates, ameliorates, stabilizes, and/or reverses disease (for example, erythrocytic malaria infection) and/or one or more symptoms of disease.

As used herein, the term "vaccination" refers to the administration of a vaccine intended to generate an immune response, for example, to a disease-causing agent. For the purposes of the present invention, vaccination can be administered before, during, and/or after exposure to a disease-causing agent, and, in certain embodiments, before, during, and/or shortly after exposure to the agent. In some embodiments, vaccination includes multiple administrations, appropriately spaced in time, of a vaccinating composition (vaccine).

The terms "comprises", "comprising", are intended to have the broad meaning ascribed to them in U.S. Patent Law and can mean "includes", "including" and the like.

Additional Embodiments of the Invention
AMA1/RON2 Complex

The AMA1/RON2 complex may be recombinantly produced, for example, from a genetically engineered system, or it may be a synthetic product, for example, produced by in vitro peptide synthesis or in vitro translation. The AMA1/RON2 complex can, in one embodiment of the invention, be produced by expression of one or more polynucleotides encoding the AMA1 and RON2 proteins. For instance, the complex can be produced by expression of a *Plasmodium* genome encoding an attenuated *Plasmodium* species, wherein the attenuation does not affect the formation of the complex.

For the purposes of making a vaccine, recombinant AMA1 protein may be made, and the RON2L peptide may be synthesized. The recombinant protein can be expressed in a bacterial system, a yeast system (for example, Pichia), a mammalian system, in vitro, and the like.

The AMA1 protein complex or components thereof may be prepared in a variety of ways in accordance with methods well known in the art. In certain embodiments, the complex is produced by expression of one or more polynucleotides encoding the AMA1 and RON2 proteins, fragments of these proteins, or fused molecules. In certain embodiments, in addition to the AMA1 and/or RON2 proteins and/or protein fragments, fused molecules can include other proteins, other fragments, and/or synthetic fragments of amino acid sequence.

Nucleic acid sequences encoding the AMA1 and RON2 proteins are known in the art and are provided, in whole and/or in part, in public databases such as those at the National Center for Biotechnology Information (NCBI). By way of example, but without limitation, AMA1 and RON2 sequences are provided at GenBank Accession Nos. XP_001348015.1 (SEQ ID NO:2), XP_729363.1 (SEQ ID NO:4), SEQ ID NO:6, SEQ ID NO:7, and SEQ ID NO:10. mRNA sequences are provided herein as SEQ ID NO:1 and SEQ ID NO:3 and SEQ ID NO:5 and SEQ ID NO:8 and SEQ ID NO:9. These include representative nucleotide sequences of one strain of *Plasmodium falciparum* parasites. Sequences of AMA1 and RON2 from other parasites and species and strains are readily available in the literature.

However, any *Plasmodium* species comprising an AMA1 and/or RON2 gene locus that is functional or that can be rendered functional via genetic manipulation is suitable for use as a source of the above-mentioned protein complex components. *Toxoplasma* species (for example, *Toxoplasma gondii*) are likewise contemplated for use as a source of the AMA1/RON2 complex components, as are other members of the *Apicomplexa* family of parasites. Furthermore, since AMA1 and RON2 are expressed in *Plasmodium* sporozoites, the vaccine according to one embodiment of the invention may be used to block this stage of the life cycle, as well.

In one embodiment, a vaccine according to the invention comprises: i) an immunogenic composition comprising a complex of: a) AMA1; and b) RON2 or a fragment thereof; and ii) at least one adjuvant and/or at least one physiologically acceptable carrier. The full-length RON2 protein is 2189 amino acids (aa). Identified herein is one 49 amino acid region sufficient to bind AMA1 and elicit a protective immune response. The exemplified 49aa sequence is within the full length protein of the mouse malaria parasite (*Plasmodium yoelli*). The corresponding *Plasmodium falciparum* sequence and others contemplated herein are, for example, and without limitation, provided in the following alignment:

```
Pb
DITQHATDIGMGPSTSCYTSLVPPPKSICIQQTVKAVLTNSTLASMK

Py
DITQHATDIGMGPSTSCYTSLLPPPKSICIQQTVKTVLTNSTLASMK

Pk
DITQHASDIGMGPVTSCYTSTIPPPKQVCIQQAVKVTLTNSTQACMK

Pv
DISQHATDIGMGPATSCYTSTIPPPKQVCIQQAVKATLTSSTQACMK

Pf
DITQQAKDIGAGPVASCFTTRMSPPQQICLNSVVNTALSTSTQSAMK

Tg
DIVQHMEDIGGAPPVSCVTNEILG-VTCAPQAIAKATTSAARVATQ
``` wherein Pb is *Plasmodium berghei*, Py is *Plasmodium yoelli*, Pk is *Plasmodium knowlesi*, Pv is *Plasmodium vivax*, Pf is *Plasmodium falciparum*, and Tg is *Toxoplasma gondii*. The SEQ ID NOs for the sequences shown, above, are as follows: for Pb, SEQ ID NO:11, for Py, SEQ ID NO:12, for Pk, SEQ ID NO:13, for Pv, SEQ ID NO:14, for Pf, SEQ ID NO:15, and for Tg, SEQ ID NO:16.

A shorter fragment within any such contemplated 49 aa region or another fragment of the full-length protein may likewise exhibit AMA1 binding capability and elicit a protective immune response.

In an additional embodiment, at least one protein of the AMA1/RON2 complex is coupled to a carrier protein. Suitable carrier proteins may include, without limitation, albumin, ovalbumin, a toxin, a growth factor, poly-L-lysine, poly-L-glutamine, or mannose-6-phosphate.

In one embodiment, a vaccine according to the invention comprises a vector comprising at least one nucleic acid molecule encoding a *Plasmodium* protein or a fragment thereof, selected from AMA1, RON2, or a complex of AMA1 and RON2. In another embodiment, two or more of such fragments are expressed on a single polypeptide. A vector can be a replicon (plasmid, phagemid, cosmid, baculovirus, bacmid, bacterial artificial chromosome, yeast artificial chromosome, as well as other bacterial, yeast, and viral vectors, such as lentiviruses, retroviruses, adenoviruses, and adeno-associated viruses). The vector can further be an expression vector, which comprises expression control sequences operatively linked to a nucleotide sequence to be expressed.

The AMA1/RON2 complex is, in one embodiment, prepared by mixing recombinant AMA1 protein and RON2L peptide (wherein the ratio of AMA1/RON2L can be adjusted according to specific needs) and incubating at room temperature for about 30 min and formulated with adjuvant. In another embodiment, for human use, the complex is further purified to remove any un-complexed AMA1 and/or RON2. In yet another embodiment, the protein binding results in the presentation of an epitope that allows the desired antibody binding to occur.

A fusion protein can, in one embodiment, be recombinant, created artificially using recombinant DNA technology. A recombinant fusion protein is created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of one or both of the proteins.

The invention also provides polypeptides and corresponding polynucleotides required for synthesis of an AMA1/RON2 protein complex. The complex includes both naturally occurring and unnaturally occurring polynucleotides and polypeptide products thereof. Naturally occurring biosynthesis products include distinct gene and polypeptide species as well as corresponding species homologs expressed in various *Plasmodium* strains. Non-naturally occurring biosynthesis products include variants of the naturally occurring products such as analogs and biosynthesis products including covalent modifications.

Purified and isolated *Plasmodium* polynucleotides (e.g., DNA sequences and RNA transcripts, both sense and complementary antisense strands) encode the bacterial AMA1 and/or RON2 biosynthesis gene products. Genomic DNA comprises the protein coding region for a polypeptide of the complex and includes variants that may be found in other *Plasmodium* strains. "Synthesized," as used herein and is understood in the art, refers to purely chemical, as opposed to enzymatic, methods for producing polynucleotides. "Wholly" synthesized DNA sequences are, therefore, produced entirely by chemical means, and "partially" synthesized DNAs embrace those wherein only portions of the resulting DNA were produced by chemical means. Preferred mRNA sequences encoding *Plasmodium* AMA1 biosynthesis gene products are set out in SEQ ID NO:1 and species homologs thereof. Preferred mRNA sequences encoding *Plasmodium* RON2 biosynthesis gene products are set out in SEQ ID NO:3 and species homologs thereof.

Autonomously replicating recombinant expression constructions such as plasmid and viral DNA vectors incorporating the biosynthesis gene sequences are also provided. Expression constructs wherein AMA1 and/or RON2 biosynthesis polypeptide-encoding polynucleotides are operatively linked to an endogenous or exogenous expression control DNA sequence and a transcription terminator are also provided. The biosynthesis genes may be cloned by PCR, using *Plasmodium* genomic DNA as the template. For ease of inserting the gene into expression vectors, PCR primers are chosen, so that the PCR-amplified gene(s) has a restriction enzyme site at the 5' end preceding the initiation codon ATG, and a restriction enzyme site at the 3' end after the termination codon TAG, TGA or TAA. If desirable, the codons in the gene(s) are changed, without changing the amino acids, according to *E. coli* codon preference described by Grosjean et al. (1982) *Gene*, 18:199-209; and Konigsberg et al. (1983) *Proc. Natl. Acad. Sci. USA*, 80:687-691. Optimization of codon usage may lead to an increase in the expression of the gene product when produced in *E. coli*. If a protein gene product is to be produced extracellularly, either in the periplasm of *E. coli* or other bacteria, or into the cell culture medium, the gene is cloned into an expression vector and linked to a signal sequence.

According to another aspect of the invention, host cells are provided, including prokaryotic and eukaryotic cells, either stably or transiently transformed, transfected, or electroporated with polynucleotide sequences of the complex proteins in a manner which permits expression of AMA1 and/or RON2 biosynthesis polypeptides. Potential expression systems of the invention include bacterial, yeast, fungal, viral, parasitic, invertebrate, and mammalian cells systems. Host cells of the invention are a valuable source of immunogen for development of antibodies specifically immunoreactive with the AMA1/RON2 complex. Host cells of the invention are conspicuously useful in methods for large scale production of AMA1 and/or RON2 biosynthesis polypeptides, wherein the cells are grown in a suitable culture medium and the desired polypeptide products are isolated from the cells or from the medium in which the cells are grown by, for example, immunoaffinity purification or any of the multitude of purification techniques well known and routinely practiced in the art. Any suitable host cell may be used for expression of the gene product, such as *E. coli*, other bacteria, including *P. multocida, Bacillus* and *S. aureus*, yeast, including *Pichia pastoris* and *Saccharomyces cerevisiae*, insect cells, or mammalian cells, including CHO cells, utilizing suitable vectors known in the art. Proteins may be produced directly or fused to a peptide or polypeptide, and either intracellularly or extracellularly by secretion into the periplasmic space of a bacterial cell or into the cell culture medium. Secretion of a protein requires a signal peptide (also known as pre-sequence); a number of signal sequences from prokaryotes and eukaryotes are known to function for the secretion of recombinant proteins. During the protein secretion process, the signal peptide is removed by signal peptidase to yield the mature protein.

To simplify the protein purification process, a purification tag may be added either at the 5' or 3' end of the gene coding sequence. Commonly used purification tags include a stretch of six histidine residues (U.S. Pat. Nos. 5,284,933 and 5,310,663), a streptavidin affinity tag described by Schmidt et al. (1993) Protein Eng., 6:109-122, a FLAG peptide (Hopp, et al. (1988) Biotechnology, 6:1205-1210), glutathione 5-transferase (Smith, et al. (1988) Gene, 67:31-40), and thioredoxin (LaVallie, et at. (1993) Bio/Technology, 11:187-193). To remove these peptide or polypeptides, a proteolytic cleavage recognition site may be inserted at the fusion junction. Commonly used proteases are factor Xa, thrombin, and enterokinase.

In one embodiment, the invention employs purified and isolated Plasmodium AMA1 and/or RON2 biosynthesis polypeptides as described above. The invention also embraces polypeptides that have at least about 99%, at least about 95%, at least about 90%, at least about 85%, at least about 80%, at least about 75%, at least about 70%, at least about 65%, at least about 60%, at least about 55%, and at least about 50% identity and/or homology to the polypeptides of the complex. Percent amino acid sequence "identity" with respect to the preferred polypeptides of the invention is defined herein as the percentage of amino acid residues in the candidate sequence that are identical with the residues in the AMA1 and/or RON2 biosynthesis gene product sequence after aligning both sequences and introducing gaps, if necessary, to achieve the maximum percent sequence identity, and not considering any conservative substitutions as part of the sequence identity. Percent sequence "homology" with respect to the polypeptides of the complex is defined herein as the percentage of amino acid residues in the candidate sequence that are identical with the residues in one of the biosynthesis polypeptide sequences after aligning the sequences and introducing gaps, if necessary, to achieve the maximum percent sequence identity, and also considering any conservative substitutions as part of the sequence identity. Conservative substitutions are well known in the art.

Polypeptides of the complex may be isolated from natural bacterial cell sources or may be chemically synthesized but are preferably produced by recombinant procedures involving host cells. AMA1 and/or RON2 biosynthesis gene products of the invention may be full-length polypeptides, biologically active fragments, or variants thereof which retain specific biological or immunological activity. The biological activity is, in one embodiment, the ability of the two proteins or fragments of either or both to bind to one another. The immunological activity is, in one embodiment, the protective immunological activity of the antigenic gene product, for example, the AMA1/RON2 complex product. Variants may comprise biosynthesis polypeptide analogs wherein one or more of the specified (i.e., naturally encoded) amino acids is deleted or replaced, or wherein one or more non-specified amino acids are added: (1) without loss of one or more of the biological activities or immunological characteristics (activity) specific for the biosynthesis gene product; or (2) with specific disablement of a particular biological activity of the biosynthesis gene product. Deletion variants contemplated also include fragments lacking portions of the polypeptide not essential for biological activity, and insertion variants include fusion polypeptides in which the wild-type polypeptide or fragment thereof have been fused to another polypeptide.

Variant AMA1 and/or RON2 biosynthesis polypeptides include those wherein conservative substitutions have been introduced by modification of polynucleotides encoding polypeptides of the complex. Conservative substitutions are recognized in the art to classify amino acids according to their related physical properties and are known in the art (see, for example, Lehninger (Biochemistry, Second Edition (1975) W. H. Freeman & Co., pp. 71-77).

Variant AMA1 and/or RON2 biosynthesis products of the complex include mature biosynthesis gene products, i.e., wherein leader or signal sequences are removed, having additional amino terminal residues. Variants contemplated herein also include gene products wherein amino-terminal sequences derived from other proteins have been introduced, as well as variants comprising amino-terminal sequences that are not found in naturally occurring proteins.

The invention also embraces variant polypeptides having additional amino acid residues resulting from the use of specific expression systems. For example, use of commercially available vectors that express a desired polypeptide as a fusion protein with glutathione-S-transferase (GST) provide the desired polypeptide having an additional glycine residue at position −1 following cleavage of the GST component from the desired polypeptide. Variants that result from expression using other vector systems are also contemplated.

Antibodies

Antibodies or epitope-binding fragments thereof which specifically bind to at least a portion of the AMA1 or RON2 or the AMA1/RON2 complex inhibit invasion of merozoites into RBCs (red blood cells). These antibodies can be monoclonal and/or polyclonal antibodies, recombinant antibodies (for example, single-chain antibodies, phage-displayed antibodies, diabodies), and antigen-binding fragments of antibodies, such as Fab or Fv. In one embodiment, the antibodies recognize epitopes of AMA1, RON2, as presented in the AMA1/RON2 complex. Methods for raising and purifying antibodies, including neutralizing antibodies, are well known in the art. In additional embodiments, the antibodies are human or humanized. They can also be human or humanized antibody homologs, chimeric antibodies, chimeric antibody homologs, monomers or dimers of antibody heavy or light chains.

The antibodies contemplated include other binding proteins specific for AMA1 and RON2 biosynthesis gene products or fragments thereof. The term "specific for" indicates that the variable regions of the antibodies described herein recognize and bind AMA1 and/or RON2 exclusively (i.e., are oftentimes able to distinguish a single O antigen from related O antigens, but may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds.); Antibodies A Laboratory Manual (1988) Cold Spring Harbor Laboratory; Cold Spring Harbor, N.Y., chapter 6. Antibodies that recognize and bind fragments of the O antigen of the invention are also contemplated, provided that the antibodies are first and foremost specific for, as defined above, an O antigen of the invention from which the fragment was derived.

Such antibodies can further comprise glycosylation that has been modulated by expression in yeast cells that have been engineered to add glycan structures to proteins. Other modifications of antibodies are likewise contemplated, including via covalent attachment of a molecule—acylated antibodies, pegylated antibodies, phosphorylated antibodies, and amidated antibodies.

The antibodies can also be variants having single or multiple amino acid substitutions, deletions, additions, or replacements, as long as they retain their desired biological property(ies), i.e., internalization, binding affinity or avidity, and/or immune effector activity.

The antibodies can, in further embodiments, be labeled (radioisotope labels, fluorescent labels) or conjugated to various moieties, including detectable moieties and drugs or toxins (bacterial toxins, organic chemicals, inorganic chemicals, and the like).

Treatment/Therapy

In certain embodiments, the present invention vaccines and methods to treat (e.g., alleviate, ameliorate, relieve, delay onset of, inhibit progression of, reduce severity of, and/or reduce incidence of one or more symptoms or features of) and/or prevent *Plasmodium* infection.

In some embodiments, methods of vaccination and/or treatment (such as those described in the sections below) involve stratification of a patient population based on prior exposure to *Plasmodium* strains. Such methods involve steps of determining whether a patient has been previously exposed to one or more of the strains. In some embodiments, if it is determined that a patient has been previously been exposed to one or more of the strains, that patient may receive less concentrated, less potent, and/or less frequent doses of the inventive vaccine or composition. If it is determined that a patient has not been previously been exposed to one or more of the *Plasmodium* strains, that patient may receive more concentrated, more potent, and/or more frequent doses of the inventive vaccine.

In one embodiment, the vaccine of the invention treats more than one *Plasmodium* infection, i.e., infection with more than one *Plasmodium* strain/species. In another embodiment, the vaccine according to the invention is administered in combination with a distinct therapy.

A number of factors can be taken into account when determining the distinct therapy: the infecting species of *Plasmodium* parasite, the clinical situation of the patient (for example, adult, child, or pregnant female, with either mild or severe malaria), and the drug susceptibility of the infecting parasites. Drug susceptibility is determined by the geographic area where the infection was acquired. Different areas of the world have malaria types that are resistant to certain medications.

Furthermore, while mild malaria can be treated with oral medication; severe malaria (one or more symptoms of either impaired consciousness/coma, severe anemia, renal failure, pulmonary edema, acute respiratory distress syndrome, shock, disseminated intravascular coagulation, spontaneous bleeding, acidosis, hemoglobinuria [hemoglobin in the urine], jaundice, repeated generalized convulsions, and/or parasitemia ([parasites in the blood]>5%) requires intravenous (IV) drug treatment and fluids in the hospital.

Known drug treatments of malaria include, but are not limited to, chloroquine, quinine sulfate plus doxycycline, tetracycline, clindamycin, atovaquone-proguanil, artemisinin-derived combination therapy (ACTs)—drug combinations like artesunate-amodiaquine, artesunate-mefloquine, artesunate-pyronaridine, dihydroartemisinin-piperaquine, and chlorproguanil-dapsoneartesunate, and spiroindolones.

Vaccine

A "vaccine" is a composition that induces an immune response in the recipient or host of the vaccine. The vaccine can induce protection against infection upon subsequent challenge with a bacterial species, herein a *Plasmodium* species. Protection refers to resistance (e.g., partial resistance) to persistent infection of a host animal with at least one *Plasmodium* species. Neutralizing antibodies generated in the vaccinated host can provide this protection. In other situations, CTL responses can provide this protection. In some situations, both neutralizing antibodies and cell-mediated immune (e.g., CTL) responses provide this protection.

Vaccines are useful in preventing or reducing infection or disease by inducing immune responses, to an antigen or antigens, in an individual. For example, vaccines can be used prophylactically in naive individuals or therapeutically in individuals already infected with at least one *Plasmodium* species.

Protective responses can be evaluated by a variety of methods. For example, either the generation of neutralizing antibodies against *Plasmodium* proteins, specifically, AMA1/RON2, and/or the generation of a cell-mediated immune response against such proteins can indicate a protective response. Protective responses also include those responses that result in lower number of bacteria colonized in a vaccinated host animal exposed to a given inoculum (of the bacteria) as compared to a host animal exposed to the same inoculum, but that has not been administered the vaccine.

The compositions of the present invention are preferably given to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of who/what is being treated. Prescription of treatment, e.g., final decisions on acceptable dosage etc., will be dictated by Vaccine Regulatory Authorities, after review of safety and efficacy data following human immunizations. Thus, a vaccine according to the invention comprises an immunoprotective or immunotherapeutic and non-toxic amount of the vaccine strain. Suitable dosage amounts can be determined by the person skilled in the art.

In general, a vaccine according to the invention will include a "therapeutic agent" (the immunogenic composition comprising the AMA1/RON2 complex), in addition to one or more inactive, agents such as a sterile, biocompatible pharmaceutical carrier including, but not limited to, sterile water, saline, buffered saline, or dextrose solution. Alternatively or additionally, the vaccine may comprise a pharmaceutically acceptable excipient, which, as used herein, includes any and all solvents, dispersion media, diluents, or other liquid vehicles, dispersion or suspension aids, disintegrating agents, surface active agents, isotonic agents, thickening or emulsifying agents, preservatives, buffering agents, solid binders, granulating agents, lubricants, coloring agents, sweetening agents, flavoring agents, perfuming agents, and the like, as suited to the particular dosage form desired. Remington's The Science and Practice of Pharmacy, 21st Ed., A. R. Gennaro, (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component of the vaccine, its use is contemplated to be within the scope of this invention.

Thus, vaccines according to the present invention, and for use in accordance with the present invention, may include, in addition to active ingredient, a pharmaceutically or physiologically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration. Examples of techniques and protocols mentioned above can be found in Remington's Pharmaceutical Sciences, 16th edition, Osol, A. (Ed.), 1980.

Vaccines according to the invention may, in one embodiment, contain an adjuvant. The term "adjuvant", as used herein, refers to any compound which, when injected together with an antigen, non-specifically enhances the immune response to that antigen. Exemplary adjuvants include Complete Freund's Adjuvant, Incomplete Freund's Adjuvant, Gerbu adjuvant (GMDP; C. C. Biotech Corp.), RIBI fowl adjuvant (MPL; RIBI Immunochemical Research, Inc.), metal salts (aluminum salts, calcium salts), potassium alum, aluminum phosphate, aluminum hydroxide, QS21 (Cambridge Biotech), TITERMAX® adjuvant (CytRx Corporation), and QUIL A® adjuvant. Other compounds that may have adjuvant properties include binders such as carboxymethylcellulose, ethyl cellulose, microcrystalline cellulose, or gelatin; excipients such as starch, lactose or dextrins, disintegrating agents such as alginic acid, sodium alginate, PRIMOGEL®, corn starch and the like; lubricants such as magnesium stearate or STEROTEX®; glidants such as colloidal silicon dioxide; sweetening agents such as sucrose or saccharin, a flavoring agent such as peppermint, methyl salicylate or orange flavoring, and a coloring agent.

Furthermore, a useful compendium of many adjuvants is prepared by the National Institutes of Health and can be found on the internet (www.niaid.nih.gov/daids/vaccine/pdf/compendium.pdf). Hundreds of different adjuvants are known in the art and could be employed in the practice of the present invention. Exemplary adjuvants that can be utilized in accordance with the invention include, but are not limited to, cytokines, aluminum salts (e.g., aluminum hydroxide, aluminum phosphate, etc.), gel-type adjuvants (e.g., calcium phosphate, etc.); microbial adjuvants (e.g., immunomodulatory DNA sequences that include CpG motifs; endotoxins such as monophosphoryl lipid A); exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes), Q57, saponins (e.g., QS21), squalene, tetrachlorodecaoxide, CPG 7909, poly[di(carboxylatophenoxy)phosphazene] (PCCP), interferon-gamma, block copolymer P1205 (CRL1005), interleukin-2 (IL-2), polymethyl methacrylate (PMMA), etc.

Vaccines according to the invention may, in another embodiment, be formulated using a diluent. Exemplary "diluents" include water, physiological saline solution, human serum albumin, oils, polyethylene glycols, glycerin, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose. Exemplary "carriers" include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

The AMA1/RON2 protein complex may, for example, be formulated into an emulsion or into biodegradable microspheres or liposomes.

Vaccines according to the invention may, in still another embodiment, contain an excipient. The term "excipient" refers herein to any inert substance (e.g., gum arabic, syrup, lanolin, starch, etc.) that forms a vehicle for delivery of an antigen. The term excipient includes substances that, in the presence of sufficient liquid, impart to a composition the adhesive quality needed for the preparation of pills or tablets.

As mentioned above, in some embodiments, interfering agents and/or binding agents in accordance with the invention may be utilized for prophylactic applications. In some embodiments, prophylactic applications involve systems and methods for preventing, inhibiting progression of, and/or delaying the onset of bacterial infection. In some embodiments, interfering agents may be utilized for passive immunization (i.e., immunization wherein antibodies are administered to a subject). In some embodiments, vaccines for passive immunization may comprise antibody interfering agents, such as those described herein. In some embodiments, passive immunization occurs when antibodies are transferred from mother to fetus during pregnancy. In some embodiments, antibodies are administered directly to an individual (e.g., by injection, orally, etc.). Of note, it is possible to immunize a person and use their antibodies for passive protection in another individual.

For example, in some embodiments, interfering agent and/or binding agent polypeptides, nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in the vaccines described herein. In some embodiments, interfering agents and/or binding agents that are not polypeptides, e.g., that are small molecules, umbrella topology glycans and mimics thereof, carbohydrates, aptamers, polymers, nucleic acids, etc., are included in the vaccines.

Administration

The mode of administration of a vaccine according to the present invention is any suitable route that delivers an immunoprotective or immunotherapeutic amount of the vaccine to the subject and is described below.

Vaccines may be administered using any amount and any route of administration effective for treatment and/or vaccination. The exact amount required will vary from subject to subject, depending on the species, age, and general condition of the subject, the severity of the infection, the particular composition, its mode of administration, its mode of activity, and the like. Vaccines are typically formulated in dosage unit form for ease of administration and uniformity of dosage. It will be understood, however, that the total daily usage of the vaccines of the present invention will be decided by the attending physician within the scope of sound medical judgment. The specific therapeutically effective dose level for any particular subject or organism will depend upon a variety of factors including the severity of the malaria infection; the activity of the specific vaccine composition employed; the half-life of the composition after administration; the age, body weight, general health, sex, and diet of the subject; the time of administration, route of administration, and rate of excretion of the specific components employed; the duration of the treatment; drugs used in combination or coincidental with the specific components employed; and like factors, well known in the medical arts.

Vaccines according to the invention may be administered by any route. In some embodiments, the vaccines are administered by a variety of routes, including oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical or transcutaneous (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

In general, the most appropriate route of administration will depend upon a variety of factors including the nature of the agent being administered (e.g., its stability upon administration), the condition of the subject (e.g., whether the subject is able to tolerate a particular mode of administration), etc. In specific embodiments, vaccines may be administered intranasally. In specific embodiments, vaccines may be administered by intratracheal instillation. In specific embodiments, vaccines may be administered by bronchial instillation. In specific embodiments, vaccines may be administered by inhalation. In specific embodiments, vaccines may be administered as a nasal spray. In specific embodiments, vaccines may be administered mucosally. In specific embodiments, vaccines may be administered orally. In specific embodiments, vaccines may be administered by intravenous injection. In specific embodiments, vaccines may be administered by intramuscular injection. In specific embodiments, vaccines may be administered by subcutaneous injection. The oral or nasal spray or aerosol route (e.g., by inhalation) is most commonly used to deliver therapeutic agents (e.g., an immunogenic composition, comprising the AMA1/RON2 complex) directly to the lungs and respiratory system. However, the invention encompasses the delivery of such a composition by any appropriate route taking into consideration likely advances in the sciences of drug delivery.

For oral administration, a vaccine according to the invention may be presented as capsules, tablets, dissolvable membranes, powders, granules, or as a suspension. The vaccine may have conventional additives, such as lactose, mannitol, corn starch, or potato starch. The vaccine also may be presented with binders, such as crystalline cellulose, cellulose derivatives, acacia, corn starch, or gelatins. Additionally, the vaccine may be presented with disintegrators, such as corn starch, potato starch, or sodium carboxymethylcellulose. The vaccine may be further presented with dibasic calcium phosphate anhydrous or sodium starch glycolate. Finally, the vaccine may be presented with lubricants, such as talc or magnesium stearate.

For parenteral administration, a vaccine according to the invention may be prepared with a sterile aqueous solution, which is preferably isotonic with the blood of the subject. Such a formulation may be prepared by dissolving a solid active ingredient in water containing physiologically compatible substances, such as sodium chloride, glycine, and the like, and having a buffered pH compatible with physiological conditions, so as to produce an aqueous solution, then rendering said solution sterile. The vaccine may be presented in unit or multi-dose containers, such as sealed ampoules or vials. The vaccine also may be delivered by any mode of injection, including any of those described herein.

Vaccines for rectal or vaginal administration are typically suppositories, which can be prepared by mixing an immunogenic composition with suitable non-irritating excipients such as cocoa butter, polyethylene glycol, or a suppository wax, which are solid at ambient temperature but liquid at body temperature and, therefore, melt in the rectum or vaginal cavity and release the immunogenic composition.

Solid dosage forms for oral administration include capsules, tablets, pills, powders, dissolvable membranes, and granules. In such solid dosage forms, the immunogenic composition is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), taste/olfactory components, and mixtures thereof. In the case of capsules, tablets and pills, the dosage form may comprise buffering agents.

Dosage forms for topical and/or transdermal administration of a vaccine in accordance with this invention may include ointments, pastes, creams, lotions, gels, powders, solutions, sprays, inhalants and/or patches. Generally, the immunogenic composition is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active therapeutic agent (e.g., the immunogenic composition) to the body. Such dosage forms may be prepared, for example, by dissolving and/or dispensing the immunogenic composition in the proper medium. Alternatively or additionally, the rate may be controlled by either providing a rate controlling membrane and/or by dispersing the compound in a polymer matrix and/or gel.

For transdermal administration, the vaccine according to the invention may be combined with skin penetration enhancers, such as propylene glycol, polyethylene glycol, isopropanol, ethanol, oleic acid, N-methylpyrrolidone, and the like, which increase the permeability of the skin to the immunogenic composition and permit the composition to penetrate through the skin and into the bloodstream. Enhancer and immunogenic composition also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The ensuing vaccine may be administered transdermally, at or near the site on the subject where the infection, neoplasm, or other disorder may be localized. Alternatively, the vaccine may be administered transdermally at a site other than the affected area, in order to achieve systemic administration.

For intranasal administration (e.g., nasal sprays) and/or pulmonary administration (administration by inhalation), a vaccine according to the invention, including an aerosol formulation, may be prepared in accordance with procedures well known to persons of skill in the art. Aerosol formulations may comprise either solid particles or solutions (aqueous or non-aqueous). Nebulizers (e.g., jet nebulizers, ultrasonic nebulizers, etc.) and atomizers may be used to produce aerosols from solutions (e.g., using a solvent such as ethanol); metered-dose inhalers and dry-powder inhalers may be used to generate small-particle aerosols. The desired aerosol particle size can be obtained by employing any one of a number of methods known in the art, including, without limitation, jet-milling, spray drying, and critical-point condensation.

Vaccines for intranasal administration may be solid formulations (e.g., a coarse powder) and may contain excipients (e.g., lactose). Solid formulations may be administered from a container of powder held up to the nose, using rapid inhalation through the nasal passages. Vaccines for intranasal administration may also comprise aqueous or oily solutions of nasal spray or nasal drops. For use with a sprayer, the vaccine may comprise an aqueous solution and additional agents, including, for example, an excipient, a buffer, an isotonicity agent, a preservative, or a surfactant. A nasal spray may be produced, for example, by forcing a suspension or solution of the immunogenic composition through a nozzle under pressure.

Formulations of a vaccine according to the invention for pulmonary administration may be presented in a form suitable for delivery by an inhalation device and may have a particle size effective for reaching the lower airways of the lungs or sinuses. For absorption through mucosal surfaces, including the pulmonary mucosa, the formulation may comprise an emulsion that includes, for example, a bioactive peptide, a plurality of submicron particles, a mucoadhesive macromolecule, and/or an aqueous continuous phase. Absorption through mucosal surfaces may be achieved through mucoadhesion of the emulsion particles.

Vaccines according to the invention for use with a metered-dose inhaler device may include a finely-divided powder containing the immunogenic composition as a suspension in a non-aqueous medium. For example, the composition may be suspended in a propellant with the aid of a surfactant (e.g., sorbitan trioleate, soya lecithin, or oleic acid). Metered-dose inhalers typically use a propellant gas (e.g., a chlorofluorocarbon, a hydrochlorofluorocarbon, a hydrofluorocarbon, or a hydrocarbon) stored in a container (e.g., a canister) as a mixture (e.g., as a liquefied, compressed gas). Inhalers require actuation during inspiration. For example, actuation of a metering valve may release the mixture as an aerosol. Dry-powder inhalers use breath-actuation of a mixed powder.

A vaccine according to the invention also may be released or delivered from an osmotic mini-pump or other timed-release device. The release rate from an elementary osmotic mini-pump may be modulated with a microporous, fast-response gel disposed in the release orifice. An osmotic mini-pump would be useful for controlling release, or targeting delivery, of the vaccine.

A vaccine according to the invention may be administered or introduced to a subject by known techniques used for the introduction of drugs, including, for example, injection and transfusion.

A vaccine according to the invention may be administered to a subject, either alone or in combination with one or more drugs used to treat the infection or a symptom of the same. A vaccine according to the invention may be administered alone or in combination with other treatments, either simultaneously or sequentially dependent upon the condition to be treated.

Dosages

The dosage of a vaccine (or other composition) according to the invention can be determined by, for example, first identifying doses effective to elicit a prophylactic and/or therapeutic immune response. This may be accomplished by measuring the serum titer of *Plasmodium*-specific immunoglobulins (anti-AMA1 or -RON2 or -AMA1/RON2 antibodies) and/or by measuring the inhibitory ratio of antibodies in serum samples. The dosages can be determined from animal studies, including animals that are not natural hosts to the parasite species in question. For example, the animals can be dosed with a vaccine candidate, e.g., a vaccine according to the invention, to partially characterize the immune response induced and/or to determine if any neutralizing antibodies have been produced. In addition, routine human clinical studies can be performed to determine the effective dose for humans.

In one embodiment, a vaccine dose consists of a range of about 1 µg to about 1 mg total protein. In another embodiment, the range is about 0.1 mg to about 1.0 mg total protein. Such a dosage could be adjusted based on the amount of polypeptide delivered. More precise dosages can further be determined by assessing the immunogenicity of the AMA1/RON2 complex.

Effective doses may be extrapolated from dose-response curves derived from in vitro and/or in vivo animal models. For example, various immunization schedules could be evaluated for optimum ensuing protection (and therapy).

An immunologically effective amount, based upon human studies, would, in one embodiment, be sufficient to stimulate an acceptable level of protective immunity in a population. For some vaccines (in certain embodiments), this immunologically effective level would provide an 80% efficacy against a malaria. For other vaccines (in other embodiments), an immunologically effective amount would be one that protects against severe malaria but may not protect against all symptoms of the infection.

In one embodiment, a vaccine according to the invention may be administered to a subject at risk of developing malaria, in an amount effective to prevent the disorder in the subject. As used herein, the phrase "effective to prevent the disorder" includes effective to hinder or prevent the development or manifestation of clinical impairment or symptoms resulting from the disorder, or to reduce in intensity, severity, and/or frequency, and/or delay of onset of one or more symptoms of the disorder.

Combinations

Compositions and vaccines according to the invention can be administered to a subject either alone or in combination with one or more other therapeutic agents including, but not limited to, vaccines and/or antibodies. By "in combination with," it is not intended to imply that the agents must be administered at the same time or formulated for delivery together, although these methods of delivery are within the scope of the invention. Compositions and vaccines according to the invention can be administered concurrently with, prior to, or subsequent to, one or more other desired therapeutics or medical procedures. It will be appreciated that therapeutically active agents utilized in combination may be administered together in a single composition or administered separately in different compositions. In general, each agent will be administered at a dose and/or on a time schedule determined for that agent.

In general, each agent (in this context, one of the "agents" is a composition or vaccine according to the invention) will be administered at a dose and on a time schedule determined for that agent. Additionally, the invention encompasses the delivery of the compositions in combination with agents that may improve their bioavailability, reduce or modify their metabolism, inhibit their excretion, or modify their distribution within the body. Although the compositions (including vaccines) according to the invention can be used for treatment and/or vaccination of any subject, they are preferably used in the treatment and/or vaccination of humans.

The particular combination of therapies (e.g., therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an agent useful for treating, preventing, and/or delaying the onset of a bacterial (or other microorganism) infection may be administered concurrently with another agent useful for treating, preventing, and/or delaying the onset of the bacterial infection), or they may achieve different effects (e.g., prevention of severe illness or control of adverse effects).

A vaccine according to certain embodiments of the invention may further comprise one or more antigens. Such antigens may, for example, be derived from a *Plasmodium* species and may be capable of eliciting an immune response directed to the *Plasmodium* species.

In general, it is expected that agents utilized in combination will be utilized at levels that do not exceed the levels at which they are utilized individually. In some embodiments, the levels utilized in combination will be lower than those utilized individually.

Kits

Kits comprising an immunogenic composition comprising a recombinant AMA1/RON2 complex or a vaccine according to the invention are provided in an additional embodiment. Kits can include one or more other elements including, but not limited to, instructions for use; other reagents, e.g., a diluent, devices or other materials for preparing the vaccine or composition for administration; pharmaceutically acceptable carriers; and devices or other materials for administration to a subject. Instructions for use can include instructions for therapeutic application (e.g., DNA vaccination and protein boosting) including suggested dosages and/or modes of administration, e.g., in a human subject, as described herein.

In another embodiment, a kit according to the invention can further contain at least one additional reagent, such as a diagnostic or therapeutic agent, e.g., a diagnostic agent to monitor an immune response to the vaccines according to the invention in the subject, or an additional therapeutic agent as described herein (see, e.g., the section herein describing combination therapies).

EXAMPLES

The following examples are provided for illustrative purposes only and are not intended to limit the scope of the invention.

Example 1

Recombinant *P. yoelli* AMA1 with a c-terminal His tag was expressed in *E. coli*, purified on a nickel column and subsequently refolded. The refolded protein was confirmed to bind a conformation-dependent mAb to verify proper folding.

PyRON2L peptide comprising the 49-amino acid region that binds AMA1 was synthesized (Lifetein LLC). Mice (5/group) were immunized with PBS (control), PyAMA1, PyRON2L, PyAMA1+PyRON2L (the two antigens injected at separate sites), or PyAMA1 PyRON2L (AMA1-RON2L preformed complex). AMA1/RON2L complex was prepared by mixing AMA1 and RON2L (1:2 ratio) and allowing complex formation to occur at room temperature for 30 min.

Figure 1:
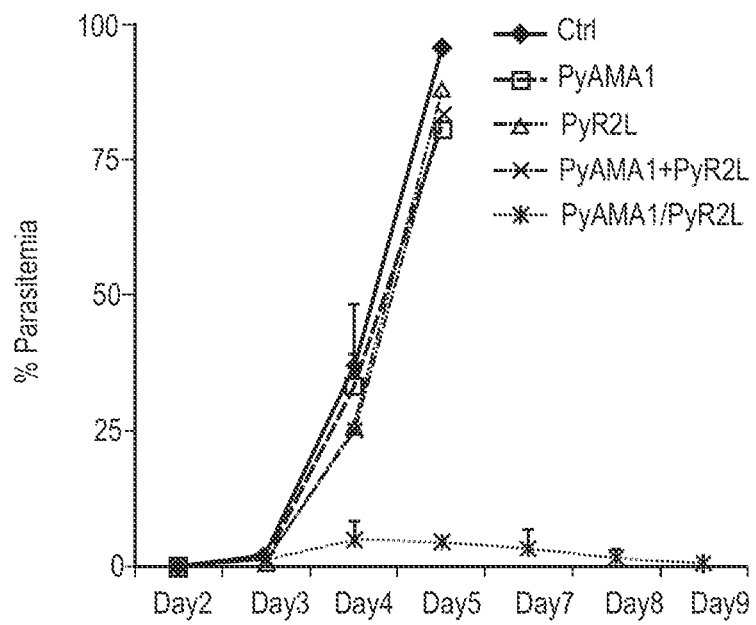
FIG. 1 depicts a graph illustrating the potential of the AMA1-RON2 peptide complex in protecting against a lethal parasite challenge. Mice immunized with buffer (Ctrl), the individual antigens (PyAMA1, PyR2L, respectively), or when mice are immunized with the two antigens separately (not as complex), the animals are not able to control parasitemia (% parasitemia over time increases). On the other hand, mice immunized with AMA1-RON2 complex (PyAMA1/PyR2L) are able to control parasitemia and clear the infection.
Figure 2:
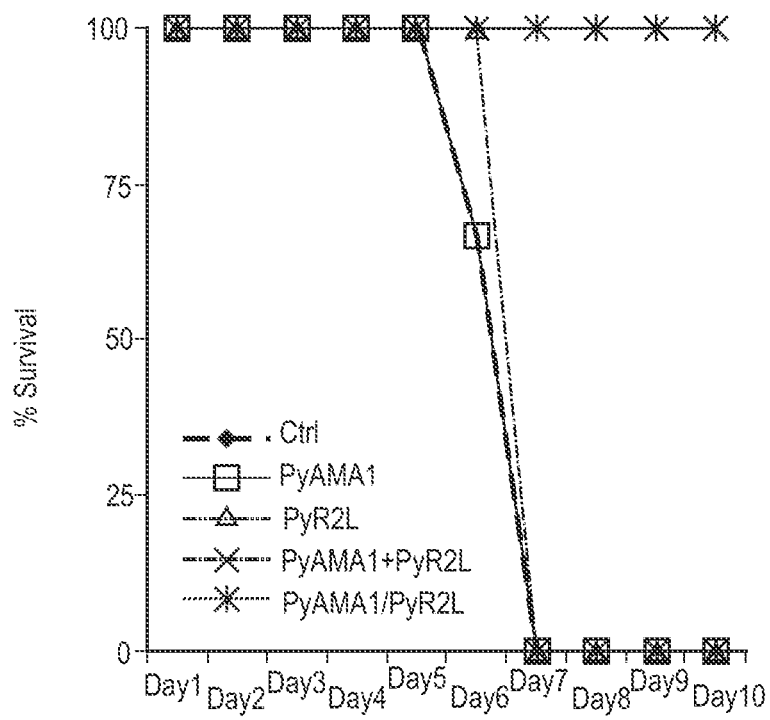
FIG. 2 depicts a graph illustrating the potential of the AMA1-RON2 peptide complex in protecting against a lethal parasite challenge. Mice immunized with buffer (Ctrl), the individual antigens (PyAMA1, PyR2L, respectively), or when mice are immunized with the two antigens separately (not as complex), the animals succumb to the disease (% survival over time decreases). On the other hand, mice immunized with AMA1-RON2 complex (PyAMA1/PyR2L) survive the disease.

Mice were immunized with the respective antigens formulated with Freund's complete adjuvant, followed by boosting with Freund's incomplete adjuvant, each two weeks apart. The AMA1+RON2L group received 10 μg of each antigen in two separate sites (20 μg total/mouse), while the AMA1, RON2L, and AMA1/RON2L groups received 10 μg antigen per animal. Two weeks after the last boost, the mice were challenged intravenously with $10^5$ parasites of a lethal strain of *P. yoelli* (XL). The effect of the vaccination was assessed by counting daily parasitemia from Geimsa-stained blood smears (FIG. 1) and monitoring survival of infected mice (FIG. 2). Control animals injected with PBS developed parasitemia that killed all the mice by Day 5. Similarly, animals that were either immunized with the single antigens (PyAMA1 or PyRON2L) or with both antigens but at different sites (PyAMA1+PyRON2L) developed parasitemia similar to control mice and succumbed to infection by Day 5. In marked contrast, all of the animals immunized with the PyAMA1/PyRON2L complex were able to control parasitemia and were protected.

Example 2

AMA1-RON2L complex, but not AMA1, protects against lethal *P. yoelli* challenge.

Recombinant Protein Production and Peptide Synthesis

*E. coli* expression: synthetic codon optimized *P. yoelii* YM AMA1 (residues 59-479; PlasmoDB accession # PYYM_0916000 (SEQ ID NO:17)) with a C-terminal histidine tag was cloned into pET24a vector. Solubilized inclusion bodies were refolded and affinity purified essentially as described (Miura, et al. 2013 *Infect Immun* 81(5):1491-1501). In brief, solubilized protein was purified on a Ni SEPHAROSE™ 6 FF column (Separation-Pharmacia-Agarose, Fast Flow, GE Healthcare, NJ), followed by separation on Q SEPHAROSE™ FF column (Separation-Pharmacia-Agarose, Fast Flow, GE Healthcare, NJ) using 20 mM Tris and a NaCl gradient at pH 8.0. The EcPyAMA1 eluates were pooled and polished on a S75 size-exclusion column (GE Healthcare, NJ) with a mobile phase consisting of phosphate buffered saline, pH 7.4. Purified recombinant EcPyAMA1 was characterized by Coomassie blue-stained SDS-PAGE gel electrophoresis, Western blot using a protective, conformational mAb 45B1 (Narum, et al. 2000 *Infect Immun* 68(5):2899-2906), reversed-phase-HPLC and analytical size-exclusion column chromatography with online multi-angle light scattering-HPLC (FIG. 9), essentially as previously described (Plassmeyer, et al. 2009 *J Biol Chem* 284(39):26951-26963).

*P. pastoris* expression: recombinant his-tagged Pf3D7 and PfFVO AMA1 full-length ectodomain (residues 25-546) as described previously (Ellis, et al. 2012 *PLoS One* 7(10): e46094) were used in the studies.

Peptide synthesis: all peptides were synthesized by Lifetein LLC (New Jersey, USA) and are listed in FIG. 10. KLH conjugation to RON2L was also performed by Lifetein LLC.

Parasites and Mouse Infections

*P. yoelii* YM parasites were maintained by serial blood passage in BALB/c mice (Charles River Laboratory). For challenge studies following vaccination, the indicated numbers of infected RBCs (iRBCs) were injected intravenously and parasitemia was monitored by counting the number of iRBCs on Giemsa stained blood smears (% parasitemia= (number of iRBCs*100)/number of total RBCs). All experiments were performed in accordance with NIH-approved animal study protocol LMVR-11E.

AMA1-RON2L Complex Preparation, Immunization

AMA1-RON2L complex was prepared by mixing 10 µg of AMA1 with 30 µg of RON2L in 50 µL PBS and incubating at room temperature for 30 min. The complex was emulsified in 50 µL of Freund's adjuvant. For AMA1 alone or RON2L-KLH alone, 10 µg and 30 µg, respectively, were added to 50 µL of PBS and emulsified in an equal volume of adjuvant. BALB/c mice were immunized subcutaneously three times (Freund's complete followed by two injections in Freund's incomplete adjuvant) in three week intervals. The control mice received 50 µL of PBS emulsified in an equal volume of adjuvant. Challenge with PyYM iRBCs were done 3 weeks after the last immunization. For injecting antigens in separate sites, 10 µg PyAMA1 and 30 µg PyRON2L, respectively, in 50 µL of PBS were emulsified separately with adjuvant and injected on opposite sides.

Figure 3:
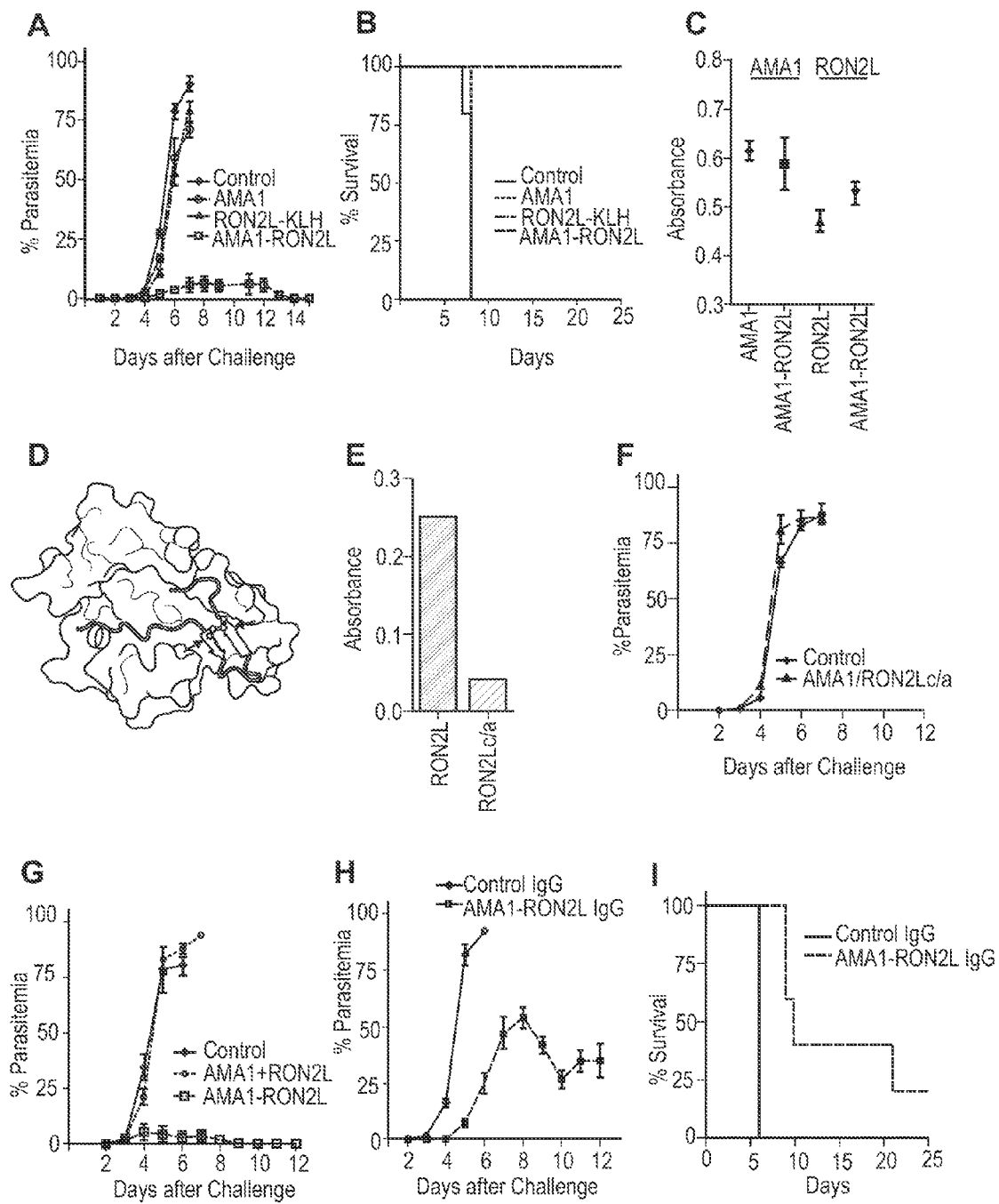
FIG. 3 (i.e., FIGS. 3A-3I, as follows) demonstrates that immunization with AMA1-RON2L complex, but not AMA1 alone, protects mice against lethal *P. yoelii* YM challenge.

To test whether AMA1 or RON2L can protect against a lethal PyYM parasite challenge, animals were immunized with recombinant PyAMA1 or RON2L peptide conjugated to KLH and challenged intravenously with PyYM-infected RBCs (iRBCs). All animals succumbed to the infection similar to control animals (FIG. 3A). This lack of protection against a homologous parasite challenge in animals vaccinated with AMA1 resembles the results from controlled human trials using *P. falciparum* (Spring, et al. 2009 *PLoS One* 4(4):e5254). Strikingly however, all animals immunized with the complex were protected against the lethal parasite challenge (FIGS. 3A and 3B). The amounts of anti-AMA1 antibodies were similar between the groups immunized with the complex or AMA1 alone (FIG. 3C), suggesting that the differences observed between the groups were due to qualitative differences in the antibody specificity.

ELISA

A detailed description of the assay is described elsewhere (Miura, et al. 2008 *J Immunol* 181(12):8776-8783). ELISA plates were coated overnight with 1 µg/mL recombinant AMA1 or 4 µg/mL RON2L peptide. For measuring relative antibodies in immunized mice, a serial dilution of the sera was performed and the dilution that produced an OD>0.5 (in the linear detection range of the assay) was used to compare the anti-AMA1 and anti-RON2L antibodies between the groups.

Antigen-specific ELISA units for PfAMA1 and PfRON2L were measured by first generating a standard curve using serially diluted IgG mixture containing either anti-AMA1 (IgG from four rats immunized with AMA1) or RON2L (IgG from four rats immunized with RON2L-KLH). Antibody units of the standards were assigned based on the reciprocal of the dilution giving an OD 405=1, and all samples were tested against the same standard as described (Miura, et al. 2008 *J Immunol* 181(12):8776-8783).

Competition ELISA was performed as described above with the addition of 0.5 µg/mL biotinylated PfRON2L peptide along with the IgG dilutions (containing the indicated AMA1-EU) to measure the ability of the antibodies to inhibit RON2L binding to Pf3D7AMA1. Streptavidin conjugated to alkaline phosphatase (Life technologies #S-921) was used (1:2000) to measure the amount of biotinylated RON2L bound to AMA1.

If immunity to virulent infection were due to vaccination with a functional AMA1-RON2L complex, it would be expected that mutating the cysteine residues in RON2L, which prevent complex formation with AMA1 (Srinivasan, et al. 2011 *PNAS USA* 108(32):13275-13280) (FIGS. 3D and 3E), would fail to protect mice. Consistent with this, immunization with a mixture of AMA1-RON2Lc/a failed to protect mice against PyYM (FIG. 3F and FIG. 6A).

To determine if protection is simply due to an additive effect of immunizing with two antigens or if a complex is required, animals were immunized with the AMA1-RON2L complex or the two antigens, AMA1 and RON2L (AMA1+ RON2L), injected in two separate sites (FIG. 3G). While mice immunized with the AMA1-RON2L complex were protected, immunizing with the two antigens separately did not protect mice against PyYM (FIG. 3G and FIG. 6B). The data indicate that protection against lethal PyYM parasites requires vaccination with a pre-formed AMA1-RON2L complex.

Example 3

AMA1-RON2 complex-induced protection is largely IgG-mediated.

Passive Transfer Studies

IgG from animals immunized with the PyAMA1-RON2L complex or control PBS as described above were purified on protein G agarose beads (GE health sciences) and dialyzed against RPMI 1640. On days −1, 0, and +1, 400 µg total IgG was injected intravenously into recipient mice and were challenged with 105 PyYM iRBCs on day 0. T cells from immunized animals were purified using the mouse pan T cell isolation kit (Miltenyi #130-095-10). All preparations used contained greater than 80% live cells as measure by counting trypan blue-stained cells. $2\times10^6$ purified T cells were injected on days −1, 0, and +1 and challenged with 105 PyYM iRBCs on day 0. FIGS. 3A and 3G are two independent experiments with mice immunized with AMA1 and/or RON2L separately. Data from two out of three independent experiments were performed with AMA1-RON2L complex are shown in FIGS. 3A and 3G. A third experiment with AMA1-RON2L complex in MONTANIDE™ ISA720 adjuvant (natural metabolizable non-mineral oil and a highly refined emulsifier from the mannide mono-oleate family) also showed complete protection. Data from one out of three independent immunizations performed with AMA1-RON2Lc/a (that does not form a complex) is shown in FIG. 3F.

For *P. falciparum* studies, four Sprague Dawley rats per group (Charles River Laboratory) were immunized subcutaneously with Pf3D7 full-length AMA1 (10 µg), RON2L-KLH (10 µg), or AMA1-RON2L complex (10 µg AMA1 mixed with 30 µg RON2L), emulsified in Freund's complete, followed by two injections in Freund's incomplete adjuvant in three week intervals, as described above. IgG from sera of individual rats were purified on protein G column (GE health sciences) and dialyzed against RPMI 1640. Rat immunizations were carried out in accordance with NIH-approved animal study protocol LMVR-1.

The contribution of antibody or T cells in conferring protection was evaluated through passive transfer studies. Total IgG (400 μg) or T cells (2×10⁶) from animals immunized with AMA1-RON2L complex were injected intravenously in native mice on days −1, 0, and +1 and challenged on day 0 with PyYM. The data suggest that the complex-dependent protection was largely antibody-mediated, as IgG, but not T cells, were able to transfer partial protection (FIGS. 3H and 3I and FIG. 6C). However, the data does not rule out the possibility of a role for T cells together with antibody in mediating complete protection.

Example 4

PfAMA1-RON2L complex induces qualitatively better growth inhibitory antibodies.

The surprising ability of the complex to confer complete protection in mice against virulent PyYM challenge prompted the evaluation of the potential of AMA1-RON2L complex as a blood-stage vaccine candidate for human malaria parasite *P. falciparum* (Pf).

*P. falciparum* Parasite Culture

Parasites were maintained in standard in vitro cultures as described (27) with modifications as follows. Briefly, parasites were grown in RPMI 1640 supplemented with 25 mM HEPES and 50 μg ml⁻¹ hypoxanthine (KD Medical), 0.5% AlbuMAX™ (lipid-rich bovine serum albumin, Invitrogen), 0.23% sodium bicarbonate (Gibco) using O+ RBCs (Interstate Blood Bank, Jackson, Tenn.) and monitored daily by Giemsa-stained blood smears.

In the absence of an easily accessible in vivo model for human malaria, an in vitro growth inhibition activity (GIA) assay is routinely used to measure efficacy of antibodies to Pf blood-stage antigens (Kennedy, et al. 2002 *Infect Immun* 70(12):6948-6960).

Growth Inhibition Assay (GIA)

Purified IgG at the desired concentration was dialyzed against RPMI 1640 (KD Medical) and incubated with iRBCs for 40 h. Parasitemia was quantified by biochemical measurement using a Pf lactate dehydrogenase assay as described previously (28). GIA reversal was performed by mixing the desired concentration of recombinant proteins with 2 mg/mL pooled IgG from four rats in each group before adding to the GIA wells. All assays were performed in duplicate.

Statistical Analysis

Differences in GIA responses between IgG from PfAMA1 and PfAMA1-RON2L groups were measured using non-parametric Mann-Whitney test. Inhibition of RON2L binding to AMA1 was measured by plotting a non-linear regression curve fit of the individual data points and comparing the $EC_{50}$ of the two curve fits.

GIA was used to compare the efficacies of anti-PfAMA1 and anti-PfAMA1-RON2L antibodies in blocking merozoite invasion.

Figure 4:
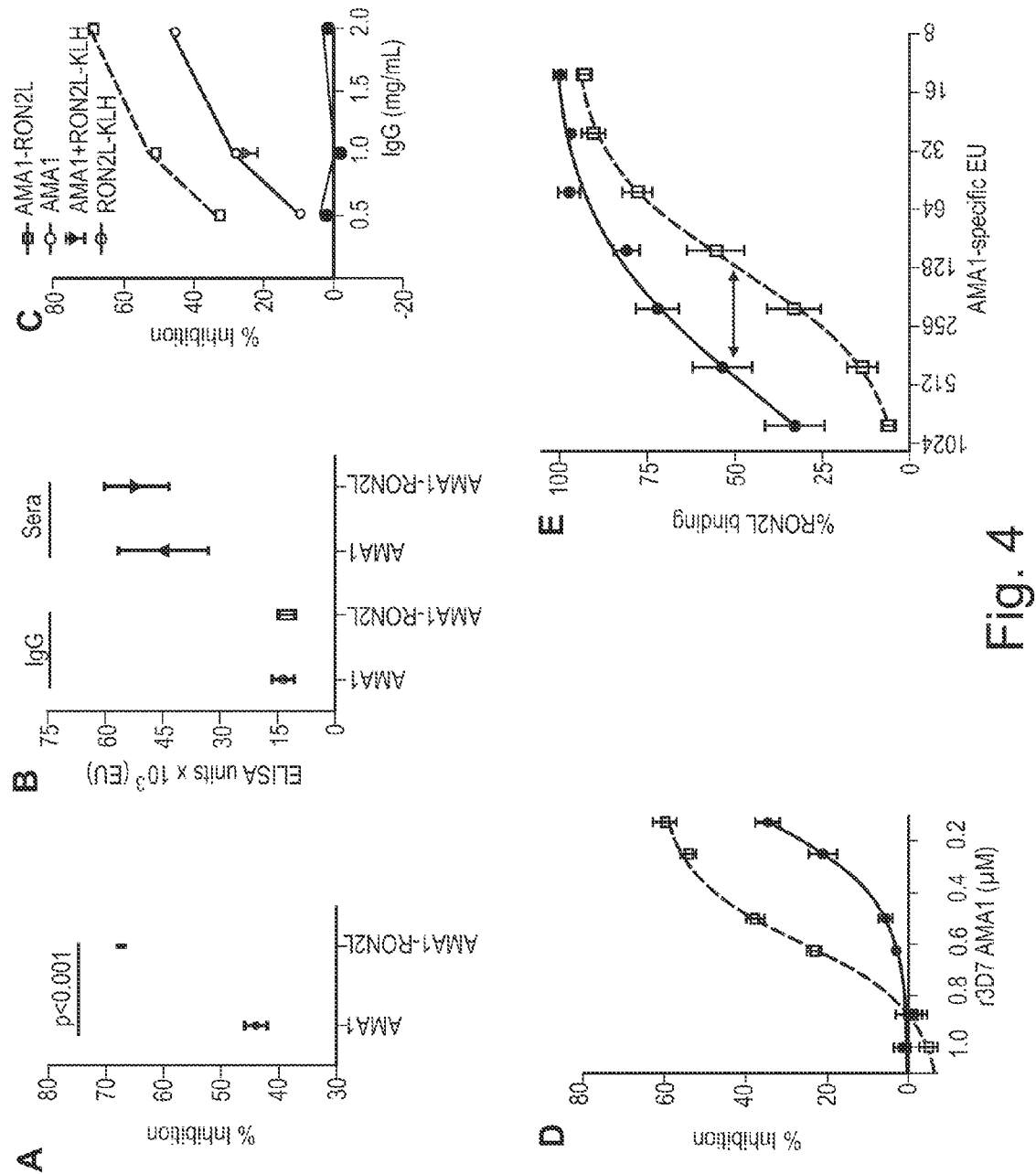
FIG. 4 (i.e., FIGS. 4A-4E, as follows) demonstrates that PfAMA1-RON2L complex generates better quality *P. falciparum* invasion inhibitory antibodies than PfAMA1.

IgG from rats immunized with Pf3D7-allele AMA1-RON2L complex showed significantly higher inhibition of merozoite invasion against homologous Pf3D7 parasites (FIG. 4A). This occurred despite comparable levels of antibodies to AMA1 in the animals immunized with AMA1 or AMA1-RON2L complex (FIG. 4B). Furthermore, antibodies to PfRON2L did not block merozoite invasion at the concentrations tested (FIG. 4C), even though the amount of RON2L-specific antibodies were higher in the RON2L-KLH group than in animals immunized with the complex (FIG. 7). Mixing anti-AMA1 and RON2L IgG (AMA1+ RON2L-KLH) did not recapitulate the increase in GIA observed with PfAMA1-RON2L complex (FIG. 4C), suggesting that RON2L-specific antibodies did not contribute significantly to GIA.

Example 5

Inhibitory antibodies induced by the complex mainly target AMA1.

The molecular basis of the qualitative difference in the antibodies induced by AMA1 and AMA1-RON2L complex was examined. Competition experiments were performed by adding recombinant Pf3D7AMA1 (rAMA1) to the GIA assays. If the increase in GIA observed with IgG from the PfAMA1-RON2L-immunized rats was due to antibodies targeting new epitopes formed by the complex, one would expect rAMA1 not to completely reverse the GIA of IgG from AMA1-RON2L-immunized rats. Interestingly, a concentration-dependent reversal of GIA is observed when rAMA1 was added to IgG from both PfAMA1- and PfAMA1-RON2L-immunized rats (FIG. 4D). This suggests that inhibitory antibodies targeting AMA1 still comprise a major part of the GIA of IgG induced by PfAMA1-RON2L complex. The qualitative increase in GIA may, therefore, be due to a difference in the proportion of inhibitory antibodies in the IgG from AMA1- and AMA1-RON2L complex-immunized rats. This is supported by the observation herein that IgG from Pf complex-immunized animals inhibited RON2L binding to AMA1 significantly higher than IgG induced by PfAMA1 (FIG. 4E). However, the contribution of antibodies targeting new epitopes formed by the PfAMA1-RON2L complex cannot be ruled out, which, in the absence of antibodies to AMA1, may not be sufficient to show significant GIA in this in vitro assay.

Example 6

PfAMA1-RON2L complex induces a switch in the proportion of antibodies to loops surrounding the RON2L binding site.

Homology Modeling of the PyAMA1-PyRON2_D3 Complex

The structural model for PyAMA1 (Asn53-Glu383; XP_729363.1 (SEQ ID NO: 4)) was generated using Modeller 9v8 through the Chimera interface (Pettersen, et al. 2004 *J Comput Chem* 25(13):1605-1612; Eswar, et al. 2006 *Curr Protoc Bioinformatics* Chapter 5:Unit 56), based off of a hybrid model of PfAMA1 (PDB ID 3ZWZ) and PvAMA1 (PDB ID 1Z40), with which it shares 52 and 56% identity, respectively. The region of the DII loop (Lys296-Ser332) disordered in the PfAMA1 co-structure with PfRON2_D3 and in the apo structure of PvAMA1 was removed due to uncertainty in its position while in complex with PyRON2_D3. The final model of PyAMA1 was chosen based on its low value of the normalized Discrete Optimized Protein Energy value (zDOPE).

The core 30 residues of PyRON2_D3 (His2068 to Val2097; XP_727536.1 (SEQ ID NO: 10)) were modelled based on PfRON2_D3 from the published co-structure with PfAMA1 (Vulliez-Le Normand, et al. 2012 *PLoS Pathog* 8(6):e1002755), and initially docked into the PyAMA1 groove using ProtInfoPPC (Kittichotirat, et al. 2009 *Nucleic Acids Res* 37(Web Server issue):W519-525). The PyAMA1-PyRON2_D3 model was refined using Rosetta FlexPepDock (London, et al. 2011 *Nucleic Acids Res* 39(Web Server issue):W249-253) with the complex showing the lowest Rosetta energy score chosen and validated by visual inspection, PISA (Krissinel, et al. 2007 *J Mol Biol* 372(3):774-797), ProQ (Wallner, et al. 2003 *Protein Sci* 12(5):1073-1086), ERRAT (Colovos, et al. 1993 *Protein Sci* 2(9):1511-1519), and MolProbity (Chen, et al. 2010 *Acta Crystallogr D Biol Crystallogr* 66(Pt1):12-21).

Figure 5:
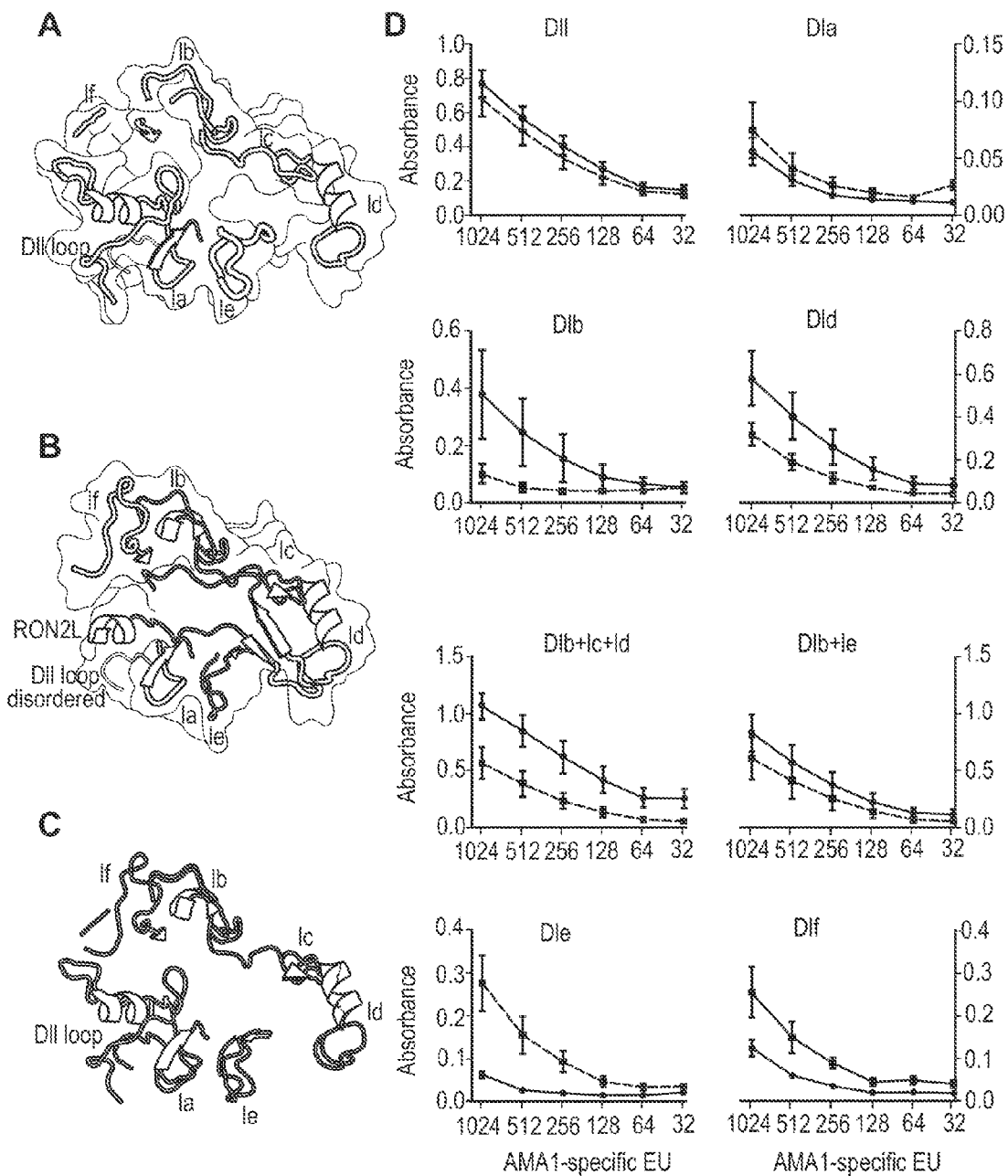
FIG. 5 (i.e., FIGS. 5A-5D, as follows) demonstrates the proportion of anti-AMA1 and anti-AMA1-RON2L complex IgG to loop regions surrounding the AMA1 hydrophobic groove.

The hydrophobic groove in AMA1 is formed by two cysteine-rich domains (Pizarro, et al. 2005 *Science* 308 (5720):408-411), and binding of RON2L displaces the conserved loop (DII) in domain 2 (Vulliez-Le Normand, et al. 2012 *PLoS Pathog* 8(6):e1002755). In addition, domain 1 loops DIb and DIf that were disordered in the apo structure (FIG. 5A) become visible in the complex structure (FIG. 5B) and a conformational change in loop DIe is also observed (FIG. 5C). Previous studies have demonstrated a positive correlation between the amounts of antibodies to loop DId and in vitro GIA (Ouattara, et al. 2013 *J Infect Dis* 207(3): 511-519), suggesting that loop regions could be targets of protective immune responses. In order to determine whether some of the conformational changes and/or stabilization of the loops upon RON2 binding may have contributed to the qualitative increase in inhibitory antibodies induced by the complex, the proportion of antibodies against synthetic biotinylated loop peptides was examined by ELISA (FIG. 5D).

Antibodies to different loop region peptides was measured by first coating individual biotinylated peptides (4 µg/mL) to streptavidin coated plates for 2 hrs at RT followed by the standard ELISA method as described previously. In order to compare the proportion of antibodies between the AMA1 and AMA1-RON2L group, each IgG sample was adjusted to have the same amount of anti-AMA1 ELISA units.

Surprisingly, while the proportion of antibodies against loop DId appears to be higher in the group immunized with AMA1 alone, antibodies to loops DIe and DIf appear to be higher in the group immunized with the AMA1-RON2L complex (FIG. 5D). Interestingly, the immune response against the DII loop, which undergoes the most conformational change, appears to be similar between the two groups (FIG. 5D). DId contains some of the highly polymorphic residues including E197, which has been shown to be a target of strain-specific anti-AMA1 antibodies (Coley, et al. 2006 *Infect Immun* 74(5):2628-2636), while loops DIe and DIf are less polymorphic (FIG. 8). The data suggest that a switch in the proportion of antibodies targeting these loops may contribute to the enhanced AMA1-RON2L complex vaccine efficacy. This suggestion is supported by a recent study showing that monoclonal antibodies targeting loop DIe potently inhibited parasite invasion (Dutta, et al. 2013 *PLoS Pathog* 9(12):e1003840).

Example 7

Non-human primate challenge using virulent human malaria parasite *P. falciparum*.

*Aotus nancymaae* was used as an in vivo human malaria parasite *P. falciparum* model to evaluate the efficacy of AMA1-RON2L complex vaccine. Three groups of monkeys were vaccinated with wither buffer (control), AMA1 alone (40 µg per injection), or AMA1-RON2L complex (1:3 to 1:5 ratio) three times in three week intervals. Four weeks after the last vaccination, all of the monkeys were challenged intravenously with $10^5$ highly virulent FVO strain of human malaria parasite *P. falciparum*. This parasite strain was chosen to ensure the most stringent model to test protective efficacy of the vaccine.

Vaccine efficacy was analyzed by monitoring the infection status and parasite load of the animals by counting parasites in their blood every day. Animals were treated with mefloquine, an antimalarial drug, when the parasitemia reached 200,000 infected cells per microliter blood or when the hematocrit fell below 25%. Antibodies purified from vaccinated animals were also used to directly measure the ability of IgG to block parasite invasion of RBCs using an in vitro growth inhibition assay as previously described.

While an approximate range of 1:3 to 1:5 ratio is described above, a range of about 1:3 to about 1:10 ratio (including any range within that range of ratios) is contemplated. Furthermore, any ratio resulting in vaccine efficacy is contemplated herein.

Thus, a novel approach towards developing a vaccine against the disease causing forms of the malaria parasite is disclosed herein. The lack of protection in humans immunized with AMA1 has been attributed to insufficient amounts of antibody generated using currently available adjuvants and the polymorphisms between the vaccine-type and parasite strains in the field. However, the lack of protection against a controlled, homologous parasite challenge despite the vaccine inducing high anti-AMA1 titers suggests that these may not be the only reason for the failure in human trials.

Evidence is provided herein using *P. yoelii* and *P. falciparum*, two independent host-parasite systems, that, despite similar AMA1 antibody titers, the AMA1-RON2L complex is more effective in inducing invasion-inhibitory, protective antibodies. The results indicate that the increased inhibitory activity of IgG induced by PfAMA1-RON2L complex is, at least in part, due to antibodies that target new AMA1 epitopes surrounding the RON2 binding site. The fact that some of these target sites are less polymorphic bodes well for the development of an effective AMA1-based vaccine.

Certainly, the results described herein have important implications for developing an effective blood-stage malaria vaccine. For instance, a multi-allele AMA1 (to cover polymorphisms) in complex with RON2L can be effective in protecting against both homologous and heterologous parasites.

What is claimed is:

1. A vaccine comprising: i) an immunogenic composition comprising a complex of AMA1 and RON2; and ii) at least one adjuvant.

2. A vaccine comprising: i) an immunogenic composition comprising a complex of: a) AMA1; and b) RON2 and/or a fragment thereof; and ii) at least one adjuvant.

3. The vaccine of claim 2, wherein the composition elicits an immune response to a *Plasmodium* species in a subject upon administration to the subject.

4. The vaccine of claim 3, wherein the immune response is sufficient to impede or prevent infection by a *Plasmodium* species.

5. The vaccine of claim 2, wherein the vaccine is for the treatment of or protection from erythrocytic and/or pre-erythrocytic malaria infection in a subject.

6. The vaccine of claim 5, wherein the treatment manifests itself in the subject as parasitemia being under control and/or the infection being cleared.

7. The vaccine of claim 3, wherein the *Plasmodium* species is selected from the group consisting of *Plasmodium falciparum, Plasmodium knowlesi, Plasmodium vivax, Plasmodium yoelii, Plasmodium malariae, Plasmodium ovale, Plasmodium brasilianum, Plasmodium cynomulgi, Plasmodium inui, Plasmodium rhodiani, Plasmodium schwetzi, Plasmodium semiovale*, and *Plasmodium simium*.

8. A method of protecting a subject from erythrocytic malaria infection comprising administering a vaccine comprising: i) an immunogenic composition comprising a complex of: a) *Plasmodium* protein AMA1 or variant thereof; and b) *Plasmodium* protein RON2 and/or a fragment or variant thereof; wherein the variant has one or more naturally encoded amino acids deleted or replaced or has one or more amino acids added, without loss of a biological or immunological activity of the variant, wherein the biological activity comprises the ability of the two proteins or variants or fragments to hind to one another, and the immunological activity comprises the protective immunological activity of the complex; ii) at least one adjuvant and/or at least one physiologically acceptable carrier to the subject in an amount effective to stimulate an immune response, thus protecting the subject from erythrocytic malaria infection.

9. A method of protecting a subject from pre-erythrocytic malaria infection comprising administering a vaccine comprising: i) an immunogenic composition comprising a complex of: a) *Plasmodium* protein AMA1 or variant thereof; and b) *Plasmodium* protein RON2 and/or a fragment or variant thereof; wherein the variant has one or more naturally encoded amino acids deleted or replaced or has one or more amino acids added, without loss of a biological or immunological activity of the variant, wherein the biological activity comprises the ability of the two proteins or variants or fragments to bind to one another, and the immunological activity comprises the protective immunological activity of the complex; and ii) at least one adjuvant and/or at least one physiologically acceptable carrier to the subject in an amount effective to stimulate an immune response, thus protecting the subject from pre-erythrocytic malaria infection.

10. A method of protecting a subject from both erythrocytic and pre-erythrocytic malaria infection comprising administering a vaccine comprising: i) an immunogenic composition comprising a complex of: a) *Plasmodium* protein AMA1 or variant thereof; and b) *Plasmodium* protein RON2 and/or a fragment or variant thereof; wherein the variant has one or more naturally encoded amino acids deleted or replaced or has one or more amino acids added, without loss of a biological or immunological activity of the variant, wherein the biological activity comprises the ability of the two proteins or variants or fragments to bind to one another, and the immunological activity comprises the protective immunological activity of the complex; and ii) at least one adjuvant and/or at least one physiologically acceptable carrier to the subject in an amount effective to stimulate an immune response, thus protecting the subject from both pre-erythrocytic and erythrocytic malaria infection.

11. A method of protecting a subject from infection by a *Plasmodium* species comprising administering a vaccine comprising: i) an immunogenic composition comprising a complex of: a) *Plasmodium* protein AMA1 or variant thereof; and b) *Plasmodium* protein RON2 and/or a fragment or variant thereof; wherein the variant has one or more naturally encoded amino acids deleted or replaced or has one or more amino acids added, without loss of a biological or immunological activity of the variant, wherein the biological activity comprises the ability of the two proteins or variants or fragments to bind to one another, and the immunological activity comprises the protective immunological activity of the complex; and ii) at least one adjuvant and/or at least one physiologically acceptable carrier to the subject in an amount effective to stimulate an immune response, thus protecting the subject from infection with the *Plasmodium* species.

12. The method of claim 11, wherein the vaccine is administered orally or parenterally.

13. The method of claim 11, wherein the vaccine is administered with another active agent.

14. The method of claim 13, wherein the agent is an antibiotic, antigen, or antibody.

15. A method for vaccinating a subject against a *Plasmodium* species comprising administering to the subject an effective amount of a vaccine comprising: i) an immunogenic composition comprising a complex of: a) *Plasmodium* protein AMA1 or variant thereof; and b) *Plasmodium* protein RON2 and/or a fragment or variant thereof; wherein the variant has one or more naturally encoded amino acids deleted or replaced or has one or more amino acids added, without loss of a biological or immunological activity of the variant, wherein the biological activity comprises the ability of the two proteins or variants or fragments to bind to one another, and the immunological activity comprises the protective immunological activity of the complex; and ii) at least one adjuvant and/or at least one physiologically acceptable carrier.

16. A method for generating protective antibodies in a subject against a *Plasmodium* species comprising administering to the subject an effective amount of a vaccine comprising: i) an immunogenic composition comprising a complex of: a) *Plasmodium* protein AMA1 or variant thereof; and b) *Plasmodium* protein RON2 and/or a fragment or variant thereof; wherein the variant has one or more naturally encoded amino acids deleted or replaced or has one or more amino acids added, without loss of a biological or immunological activity of the variant, wherein the biological activity comprises the ability of the two proteins or variants or fragments to bind to one another, and the immunological activity comprises the protective immunological activity of the complex; and ii) at least one adjuvant and/or at least one physiologically acceptable carrier.

17. A method for producing an immune response against a *Plasmodium* species in a subject comprising administering a vaccine comprising: i) an immunogenic composition comprising a complex of: a) *Plasmodium* protein AMA1 or variant thereof; and b) *Plasmodium* protein RON2 and/or a fragment or variant thereof; wherein the variant has one or more naturally encoded amino acids deleted or replaced or has one or more amino acids added, without loss of a biological or immunological activity of the variant, wherein the biological activity comprises the ability of the two proteins or variants or fragments to bind to one another, and the immunological activity comprises the protective immunological activity of the complex; and ii) at least one adjuvant and/or at least one physiologically acceptable carrier to the subject in an amount effective to produce an immune response against the *Plasmodium* species.

18. The method of claim 11, wherein the *Plasmodium* species is selected from the group consisting of *Plasmodium falciparum, Plasmodium knowlesi, Plasmodium vivax, Plasmodium yoelii, Plasmodium malariae, Plasmodium ovale, Plasmodium brasilianum, Plasmodium cynomulgi, Plasmodium inui, Plasmodium rhodiani, Plasmodium schwetzi, Plasmodium semiovale*, and *Plasmodium simium*.

19. An article of manufacture comprising a closed, pathogen-impermeable container and a sterile vaccine preparation enclosed within said container, wherein said vaccine preparation comprises the vaccine of claim 2.

* * * * *

SEQUENCE LISTING

```
<160> NUMBER OF SEQ ID NOS: 39

<210> SEQ ID NO 1
<211> LENGTH: 1869
<212> TYPE: DNA
<213> ORGANISM: Plasmodium falciparum

<400> SEQUENCE: 1
atgagaaaat tatactgcgt attattattg agcgcctttg agtttacata tatgataaac      60
tttggaagag gacagaatta ttgggaacat ccatatcaaa atagtgatgt gtatcgtcca     120
atcaacgaac atagggaaca tccaaaagaa tacgaatatc cattacacca ggaacataca     180
taccaacaag aagattcagg agaagacgaa aatacattac aacacgcata tccaatagac     240
cacgaaggtg ccgaacccgc accacaagaa caaaatttat tttcaagcat tgaaatagta     300
```

```
gaaagaagta attatatggg taatccatgg acggaatata tggcaaaata tgatattgaa      360
gaagttcatg gttcaggtat aagagtagat ttaggagaag atgctgaagt agctggaact      420
caatatagac ttccatcagg gaaatgtcca gtatttggta aaggtataat tattgagaat      480
tcaaatacta cttttttaac accggtagct acgggaaatc aatatttaaa agatggaggt      540
tttgcttttc ctccaacaga acctcttatg tcaccaatga cattagatga aatgagacat      600
ttttataaag ataataaata tgtaaaaaat ttagatgaat tgactttatg ttcaagacat      660
gcaggaaata tgattccaga taatgataaa aattcaaatt ataaatatcc agctgtttat      720
gatgacaaag ataaaaagtg tcatatatta tatattgcag ctcaagaaaa taatggtcct      780
agatattgta ataaagacga agtaaaagaa acagcatgt tttgttttag accagcaaaa      840
gatatatcat ttcaaaacta tacatattta agtaagaatg tagttgataa ctgggaaaaa      900
gtttgcccta gaaagaattt acagaatgca aaattcggat tatgggtcga tggaaattgt      960
gaagatatac cacatgtaaa tgaatttcca gcaattgatc ttttgaatg taataaatta     1020 gttttttgaat tgagtgcttc ggatcaacct aaacaatatg aacaacattt aacagattat     1080
gaaaaaatta agaaggttt caaaaataag aacgctagta tgatcaaaag tgcttttctt     1140
cccactggtg cttttaaagc agatagatat aaaagtcatg gtaagggtta taattgggga     1200
aattataaca cagaaacaca aaaatgtgaa attttaatg tcaaaccaac atgtttaatt     1260
aacaattcat catacattgc tactactgct ttgtcccatc ccatcgaagt tgaaaacaat     1320
tttccatgtt cattatataa agatgaaata atgaaagaaa tcgaaagaga atcaaaacga     1380
attaaattaa atgataatga tgatgaaggg aataaaaaaa ttatagctcc aagaattttt     1440
atttcagatg ataaagacag tttaaaatgc ccatgtgacc ctgaaatggt aagtaatagt     1500
acatgtcgtt tctttgtatg taatgtgta gaagaagggg cagaagtaac atcaaataat     1560
gaagttgtag ttaaagaaga atataaagat gaatatgcag atattcctga acataaacca     1620
acttatgata aaatgaaaat tataattgca tcatcagctg ctgtcgctgt attagcaact     1680
attttaatgg tttatcttta taaagaaaa ggaaatgctg aaaaatatga taaaatggat     1740
gaaccacaag attatgggaa atcaaattca agaaatgatg aaatgttaga tcctgaggca     1800 tcttttggg gggaagaaaa aagagcatca catacaacac cagttctgat ggaaaaacca     1860
tactattaa                                                             1869
```

<210> SEQ ID NO 2  
<211> LENGTH: 622  
<212> TYPE: PRT  
<213> ORGANISM: Plasmodium falciparum

<400> SEQUENCE: 2

```
Met Arg Lys Leu Tyr Cys Val Leu Leu Leu Ser Ala Phe Glu Phe Thr
1               5                   10                  15

Tyr Met Ile Asn Phe Gly Arg Gly Gln Asn Tyr Trp Glu His Pro Tyr
            20                  25                  30

Gln Asn Ser Asp Val Tyr Arg Pro Ile Asn Glu His Arg Glu His Pro
        35                  40                  45

Lys Glu Tyr Glu Tyr Pro Leu His Gln Glu His Thr Tyr Gln Gln Glu
    50                  55                  60

Asp Ser Gly Glu Asp Glu Asn Thr Leu Gln His Ala Tyr Pro Ile Asp
65                  70                  75                  80

His Glu Gly Ala Glu Pro Ala Pro Gln Glu Gln Asn Leu Phe Ser Ser
                85                  90                  95
```

-continued

```
Ile Glu Ile Val Glu Arg Ser Asn Tyr Met Gly Asn Pro Trp Thr Glu
            100                 105                 110

Tyr Met Ala Lys Tyr Asp Ile Glu Glu Val His Gly Ser Gly Ile Arg
        115                 120                 125

Val Asp Leu Gly Glu Asp Ala Glu Val Ala Gly Thr Gln Tyr Arg Leu
    130                 135                 140

Pro Ser Gly Lys Cys Pro Val Phe Gly Lys Gly Ile Ile Glu Asn
145                 150                 155                 160

Ser Asn Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
            180                 185                 190

Met Thr Leu Asp Glu Met Arg His Phe Tyr Lys Asp Asn Lys Tyr Val
        195                 200                 205

Lys Asn Leu Asp Glu Leu Thr Leu Cys Ser Arg His Ala Gly Asn Met
    210                 215                 220

Ile Pro Asp Asn Asp Lys Asn Ser Asn Tyr Lys Tyr Pro Ala Val Tyr
225                 230                 235                 240

Asp Asp Lys Asp Lys Cys His Ile Leu Tyr Ile Ala Ala Gln Glu
                245                 250                 255

Asn Asn Gly Pro Arg Tyr Cys Asn Lys Asp Glu Ser Lys Arg Asn Ser
            260                 265                 270

Met Phe Cys Phe Arg Pro Ala Lys Asp Ile Ser Phe Gln Asn Tyr Thr
        275                 280                 285

Tyr Leu Ser Lys Asn Val Val Asp Asn Trp Glu Lys Val Cys Pro Arg
    290                 295                 300

Lys Asn Leu Gln Asn Ala Lys Phe Gly Leu Trp Val Asp Gly Asn Cys
305                 310                 315                 320

Glu Asp Ile Pro His Val Asn Glu Phe Pro Ala Ile Asp Leu Phe Glu
                325                 330                 335

Cys Asn Lys Leu Val Phe Glu Leu Ser Ala Ser Asp Gln Pro Lys Gln
            340                 345                 350

Tyr Glu Gln His Leu Thr Asp Tyr Glu Lys Ile Lys Glu Gly Phe Lys
        355                 360                 365

Asn Lys Asn Ala Ser Met Ile Lys Ser Ala Phe Leu Pro Thr Gly Ala
    370                 375                 380

Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
                405                 410                 415

Thr Cys Leu Ile Asn Asn Ser Ser Tyr Ile Ala Thr Thr Ala Leu Ser
            420                 425                 430

His Pro Ile Glu Val Glu Asn Asn Phe Pro Cys Ser Leu Tyr Lys Asp
        435                 440                 445

Glu Ile Met Lys Glu Ile Glu Arg Glu Ser Lys Arg Ile Lys Leu Asn
    450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
                485                 490                 495

Val Ser Asn Ser Thr Cys Arg Phe Phe Val Cys Lys Cys Val Glu Arg
            500                 505                 510
```

| | | | | | | | | | | | | |
|---|---|---|---|---|---|---|---|---|---|---|---|---|
|Arg|Ala|Glu|Val|Thr|Ser|Asn|Asn|Glu|Val|Val|Lys|Glu|Glu|Tyr|
| | |515| | | |520| | | |525| | | | |

| | | | | | | | | | | | | |
|---|---|---|---|---|---|---|---|---|---|---|---|---|
|Lys|Asp|Glu|Tyr|Ala|Asp|Ile|Pro|Glu|His|Lys|Pro|Thr|Tyr|Asp|Lys|
| |530| | | | |535| | | | |540| | | | |

| | | | | | | | | | | | | |
|---|---|---|---|---|---|---|---|---|---|---|---|---|
|Met|Lys|Ile|Ile|Ile|Ala|Ser|Ser|Ala|Ala|Val|Ala|Val|Leu|Ala|Thr|
|545| | | | |550| | | | |555| | | | |560|

| | | | | | | | | | | | | |
|---|---|---|---|---|---|---|---|---|---|---|---|---|
|Ile|Leu|Met|Val|Tyr|Leu|Tyr|Lys|Arg|Lys|Gly|Asn|Ala|Glu|Lys|Tyr|
| | | | |565| | | | |570| | | | |575| |

| | | | | | | | | | | | | |
|---|---|---|---|---|---|---|---|---|---|---|---|---|
|Asp|Lys|Met|Asp|Glu|Pro|Gln|Asp|Tyr|Gly|Lys|Ser|Asn|Ser|Arg|Asn|
| | | |580| | | | |585| | | | |590| | |

| | | | | | | | | | | | | |
|---|---|---|---|---|---|---|---|---|---|---|---|---|
|Asp|Glu|Met|Leu|Asp|Pro|Glu|Ala|Ser|Phe|Trp|Gly|Glu|Lys|Arg|
| | |595| | | | |600| | | | |605| | |

| | | | | | | | | | | | | |
|---|---|---|---|---|---|---|---|---|---|---|---|---|
|Ala|Ser|His|Thr|Thr|Pro|Val|Leu|Met|Glu|Lys|Pro|Tyr|Tyr|
| |610| | | | |615| | | | |620| | |

<210> SEQ ID NO 3
<211> LENGTH: 1674
<212> TYPE: DNA
<213> ORGANISM: Plasmodium yoelii

<400> SEQUENCE: 3

```
atgaaagaaa tatattatat atttatttta tgctctattt atctaataaa cctgagttat      60
tgttccgaag gtccaaatca agttatttca gaagatggca atattaatta tgaatcaatt     120
ccaaaggaaa atactgaaag aagtattaaa ttaattaatc catgggataa atatatggaa     180
aaatatgata tagaaaaggt gcatggttct ggtataagag tcgatttagg tgaagatgca     240
cgggtggaaa tcgagatta tagaatacca tcaggtaaat gcccagttat aggaaaaggt     300
ataactattc aaaattctga agtatcattt ttaaaaccag tagctaccgg tgataagcca     360
gtaagaagtg gaggattggc atttcctgaa acagatgtac acatttctcc tataacaatt     420
accaatctaa aaacaatgta taggaccat caagacatag taaatttaaa tgatatgtca     480
ttgtgtgcaa acatacctc actttatgtt cccggtaaag atgccacatc agcatataga     540
catcccgttg tttatgataa atctaatagt acttgttaca tgttgtatgt agcagcacaa     600
gaaaatatgg gtccaagata ttgtagtaat gatgcaaata atgagaatca accattttgt     660
tttacacccg aaaaaataga aaattataaa gatttatctt atttaactaa aaatttgcgt     720
gatgattggg aaaccagttg tcctaataaa agtataaaaa atgctaaatt tggaatctgg     780
gttgatggtt attgtacaga ttatcaaaag cacgtagttc atgatagtga ttcattatta     840
aaatgtaatc aaatcatttt taacgaaagt gcttctgatc aacctaaaca atatgaaaga     900
cacctagaag atgctaccaa aattcgacaa ggaattgtag agagaaatgg taaacttata     960
ggtgaagctt tattaccaat aggatcttat aaatcaggtc aaattaaaag tcatggaaag    1020
ggatataact ggggaaatta tgatagtaaa aacaataaat gttacatttt cgaaacaaaa    1080
ccaacatgtt taattaatga taagaatttt attgcaacaa ctgctttatc tagtactgaa    1140
gaattcgaag aaaattttcc ttgtgaaata tataaaaata aatagccga gaaattaaa    1200
gtattaaact taaccaaaaa cacctctaat ggaaataatt ccattaaatt tcctaggata    1260
tttatttcaa ctgacaaaaa tagtttaaat tgtccatgtg atcctacgaa attgactgaa    1320
agtacttgtg aattttatgt gtgtagttgt gtagagcaaa gacaatatat agctgagaat    1380
aatgatgtta aataaaaga agagtttata ggtgactatg aaaacccaaa acagaaatta    1440
ttaattatta tagtttttgat tggtgttgga attataatag tcattctatt agtggcttat    1500
```

```
tactttaaaa gtggcaaaaa aggtgaaaat tatgatagaa tgggtcaagc agatgattat    1560
ggtaaatcta atccagaaa agatgaaatg ttagatccag aagtgtcatt ttggggtgaa    1620
gataaaaggg catcacacac aacacccgtt ttgatggaaa aaccatatta ttaa         1674
```

<210> SEQ ID NO 4
<211> LENGTH: 557
<212> TYPE: PRT
<213> ORGANISM: Plasmodium yoelii

<400> SEQUENCE: 4

```
Met Lys Glu Ile Tyr Tyr Ile Phe Ile Leu Cys Ser Ile Tyr Leu Ile
1               5                   10                  15

Asn Leu Ser Tyr Cys Ser Glu Gly Pro Asn Gln Val Ile Ser Glu Asp
            20                  25                  30

Gly Asn Ile Asn Tyr Glu Ser Ile Pro Lys Glu Asn Thr Glu Arg Ser
        35                  40                  45

Ile Lys Leu Ile Asn Pro Trp Asp Lys Tyr Met Glu Lys Tyr Asp Ile
    50                  55                  60

Glu Lys Val His Gly Ser Gly Ile Arg Val Asp Leu Gly Glu Asp Ala
65                  70                  75                  80

Arg Val Glu Asn Arg Asp Tyr Arg Ile Pro Ser Gly Lys Cys Pro Val
                85                  90                  95

Ile Gly Lys Gly Ile Thr Ile Gln Asn Ser Glu Val Ser Phe Leu Lys
            100                 105                 110

Pro Val Ala Thr Gly Asp Lys Pro Val Arg Ser Gly Gly Leu Ala Phe
        115                 120                 125

Pro Glu Thr Asp Val His Ile Ser Pro Ile Thr Ile Thr Asn Leu Lys
    130                 135                 140

Thr Met Tyr Lys Asp His Gln Asp Ile Val Asn Leu Asn Asp Met Ser
145                 150                 155                 160

Leu Cys Ala Lys His Thr Ser Leu Tyr Val Pro Gly Lys Asp Ala Thr
                165                 170                 175

Ser Ala Tyr Arg His Pro Val Val Tyr Asp Lys Ser Asn Ser Thr Cys
            180                 185                 190

Tyr Met Leu Tyr Val Ala Ala Gln Glu Asn Met Gly Pro Arg Tyr Cys
        195                 200                 205

Ser Asn Asp Ala Asn Asn Glu Asn Gln Pro Phe Cys Phe Thr Pro Glu
    210                 215                 220

Lys Ile Glu Asn Tyr Lys Asp Leu Ser Tyr Leu Thr Lys Asn Leu Arg
225                 230                 235                 240

Asp Asp Trp Glu Thr Ser Cys Pro Asn Lys Ser Ile Lys Asn Ala Lys
                245                 250                 255

Phe Gly Ile Trp Val Asp Gly Tyr Cys Thr Asp Tyr Gln Lys His Val
            260                 265                 270

Val His Asp Ser Asp Ser Leu Leu Lys Cys Asn Gln Ile Ile Phe Asn
        275                 280                 285

Glu Ser Ala Ser Asp Gln Pro Lys Gln Tyr Glu Arg His Leu Glu Asp
    290                 295                 300

Ala Thr Lys Ile Arg Gln Gly Ile Val Glu Arg Asn Gly Lys Leu Ile
305                 310                 315                 320

Gly Glu Ala Leu Leu Pro Ile Gly Ser Tyr Lys Ser Gly Gln Ile Lys
                325                 330                 335

Ser His Gly Lys Gly Tyr Asn Trp Gly Asn Tyr Asp Ser Lys Asn Asn
            340                 345                 350
```

```
Lys Cys Tyr Ile Phe Glu Thr Lys Pro Thr Cys Leu Ile Asn Asp Lys
            355                 360                 365

Asn Phe Ile Ala Thr Thr Ala Leu Ser Ser Thr Glu Glu Phe Glu Glu
    370                 375                 380

Asn Phe Pro Cys Glu Ile Tyr Lys Asn Lys Ile Ala Glu Glu Ile Lys
385                 390                 395                 400

Val Leu Asn Leu Asn Gln Asn Thr Ser Asn Gly Asn Asn Ser Ile Lys
                405                 410                 415

Phe Pro Arg Ile Phe Ile Ser Thr Asp Lys Asn Ser Leu Asn Cys Pro
            420                 425                 430

Cys Asp Pro Thr Lys Leu Thr Glu Ser Thr Cys Glu Phe Tyr Val Cys
            435                 440                 445

Ser Cys Val Glu Gln Arg Gln Tyr Ile Ala Glu Asn Asn Asp Val Ile
    450                 455                 460

Ile Lys Glu Glu Phe Ile Gly Asp Tyr Glu Asn Pro Lys Gln Lys Leu
465                 470                 475                 480

Leu Ile Ile Ile Val Leu Ile Gly Val Gly Ile Ile Val Ile Leu
                485                 490                 495

Leu Val Ala Tyr Tyr Phe Lys Ser Gly Lys Gly Asn Tyr Asp
    500                 505                 510

Arg Met Gly Gln Ala Asp Asp Tyr Gly Lys Ser Lys Ser Arg Lys Asp
            515                 520                 525

Glu Met Leu Asp Pro Glu Val Ser Phe Trp Gly Glu Asp Lys Arg Ala
            530                 535                 540

Ser His Thr Thr Pro Val Leu Met Glu Lys Pro Tyr Tyr
545                 550                 555

<210> SEQ ID NO 5
<211> LENGTH: 6570
<212> TYPE: DNA
<213> ORGANISM: Plasmodium falciparum

<400> SEQUENCE: 5
atgttaaaat ttttcatatt cattttacac atatatttat acatcgattc aatatattca      60
tcagaactaa gcaaacatgt aaaacatgat acagatgaat taaaatatgc tagtccaact     120
tatgatccca agaaaggtac caaggttatt ttttatatgc caggaaatga gcaaggcgtt     180
ataccgaata atatacaaaa taaacaacat ggaacctcaa tatatcctgc tattgaatat     240
cctactacta aatatcctgc tattgaatat cctggtagtg aaatgaataa tgggaaaaca     300
ggaactacta attcaggaat atataataaa gcccatggat cttctaatga ttataatgca     360
agtaattctc aagataaaac cataaattta catatagatg aaaataattc aaataattca     420
tatcaaccat atgattcaaa taatactaat aataatacta atagtaataa taatagtaat     480
aataatagta ataataatag taataataat agtaataatt atagtaataa taatagtaat     540
actaatagta atactaatag taatactaat agtaataata atactactaa ttatgattta     600
aacagtgaat atgaaaaaat tagaagaaaa gaagaagaag ctgcaagaag aatagaaaga     660
gaaagaagag cagatataaa tagaaaaaat caagataata attctaacaa atataataat     720
gaacaaaatg gaggatatga atctgatgga aattcaccca atagtagagt aaatataaat     780
ataacaaata tggaacacat ggtaatccg cataataata attcttatgg tcacaaaaat     840
aatatgcata atacaactaa tggtaattat gctaatggta attatgctaa tggtaattat     900
agtaaaggtg attatactaa tggtgattat actaatggtg attataccaa cggagattat     960
```

```
actaatggta taaataataa tatgcatggt aagaataatt ataatacagc taatggtgaa  1020
tatgttaatg gagcttatga tgggttgaat aatggatcat ataaattaat tggtaattta  1080
aataataacc aaaatgtaga taattcttat aatcaaggta atgaaaatga taaaacatac  1140
acatccaatt acaatataaa tcttgaagat aataaaaatt ctccagataa taaccaaaat  1200
tatatatcaa catttaacaa agatataggt ccaaataaat ctgaaagatc atattatgat  1260
gtgtatggaa gagaatatga tgataacaaa tataatccat ataataaaac aaataatcat  1320
aacacaaatc aaaatggatc gacaacgtat gggtccaatg ccaatggaac atacgggcct  1380
aatgaaacat atggatctaa tggaacatac gagcctaatg aatcatatgg acctaatgga  1440
gcatatggac ctaatggaac atatggacac aatggaaagt atgggtctaa gggaacatac  1500
ggaaataatg aaactcctta ttatgtggaa catccagaat atgataatgg aaaatctatg  1560
tccgattttc atgtaaaaga ttccaaggat aatattggac ctgggggaga ttaccctaat  1620
ttgtatcaaa acatatatgg aaatgaaaaa atccaaata tttttccagg aagtcctcgt  1680
aatataaatg tatattctgt tcaccatata ccaaataatg gtgcaaatgg tggtttaaat  1740
agtggtgcaa atggtggttt aaataatggt gcaaatgatg gtttaaataa tggtgcaaat  1800
ggtggtttaa ataatggtgc aaatggtggt ttaaataatg gtgcaaatgg tggtttaaat  1860
aatggtatga caatggtat gaataatggt atgaataatg gtatgaataa tggtatgaat  1920
aatggtatga ataatggtat gaataatggt acaaatggtg gtttaaataa tggtatgaat  1980
aatggtatga ataatggtat gaataatggt atgaataatg gtacatgaa tgacttatat  2040 aatagtgaaa acagtacttt taataacggt ctgaataatt caggaagaac tggattaaat  2100
aatgcatatc ctcataatgg tatgcttaat aatggaaccg aatataatgt acattatgga  2160
aacagtgatt ctaataatac gaatgacagt atgctaaatg aaaactatta tagtgatagt  2220
gactatgatg atcacacccc agggaacaaa aagaaagtat ataaaagtgt agctgaaagg  2280
aataaaaaat ctgcttctca agatagttta ggagcaggat ttagtgatag tgatagcgat  2340
agtgaatacg aagtagtaga tggggaaaat aaaaaaataca aaaagaagaa taaggaaaat  2400
aatgaaaaag ataaatatga aataattgg gattccaata attataattc tgataatgaa  2460
attaaagatg gttatttaag tgaatctgaa agagaatatg caagaaataa agcgaatgaa  2520
attgaagata aaatgaagaa aggagaatat tctcgaaagt ataaaatag taaatcgaat  2580 gaatccggat atgcttcaaa acaaacatcc gattcagatg attctgatat tgaagcaaat  2640
gcattttatg tagataatgg acaagaaatg ttaataaaag aaaagaaca ttattcaagt  2700 gattcagaac atcataagga agaatctgct tctattggaa atttaaatgt atttttcct  2760 gctgaaaatt atcattttc aacgtatatg ggatttgata gaagatcgtt tttaccctct  2820
aatgaaattg aattagaaaa aatgattgga gcgaactttt caaatgaagt taaaaattat  2880
tgtagccgtc aaaatgttgc acaaaaaata ggagactatc tgaatatatc atttgaatat  2940
tctagagcat tagaagaatt aagatctgaa atgatcctag attttaataa acgtaaacat  3000
ttaacaaata atactgatga cacaatttta cacatgatag aaaatgcaga gaaaagaaaa  3060
aatgatccta attataaaga agcgtatgaa aataaagatt atgcaaataa tgctaatatc  3120
tttatgaatg aatatagtaa tccattaagt acaaaatata taaaatatt aaaagaatat  3180 ctttgtcatt tatttgttaa taatccaggt actaaaccat tagagagatt atattataat  3240
agtttagcat taggagaact tgttgaacca ataagaaata aatttaaaag tttagcatca  3300
```

```
tccacaattg attttaatta tgaaattcat atggcttcgg catctaatat atatttactt    3360
gcacatttct tagtattatc cttggcatat cttcatata atgaatattt tacgacagga    3420
accaaatcat tttattcatt accaaccata cttacagcta attctgataa tagttttttc    3480
atgttaaatg aaatgtgtaa tattcattat aatcccaata aaaatttcaa aaagatata     3540 acgtttatac ctattgaatc aaggcctaaa agaactacaa cattttatgg tgagagaaga    3600
ttaacatgtg atttattgga attagtatta aatgctatta tgttaattaa tattaatgaa    3660
ataaacaatg tattttctaa taataatgta gatggatatg aaaattcctt atctttttca    3720
cataatgcta ttagaatatt ttcgaaagta tgtcctaaaa ttaataatga caatgtatta    3780
aaatgtgaat ttgaagaatc aagtttatat aatcctaaaa ttattaagaa tgatacatca    3840
gaaaaatcga gtcaaaaaaa tttaaaaaaa gcatttgatt tattaagaac ttatgctgaa    3900
atagaaggcc attcagctga aggtagcaca agtccatatt atgtaagtct aatattagat    3960
gatatgaaat ataatgattt ttataaatat acactttggt atgaacctag agaattaata    4020
tatggtgata tcagaggtat gcaaatgaaa aaaagaaga aaacaaaata tatatataac    4080
gattttatga aaagagtac ccaattaaaa aagaaattaa taaaaaatga tttgaaatat    4140
aatttaaaga gtaaaggatt agtattttta tatgcaatga ttgataaata tggaagtata    4200
ttaaataaaa gtcaaaaagc aaaagttcaa ttttttaaata gtacttcatc tatacgttat    4260
tatctatatt taaacaaagt aatattcaag tcagcaaaaa cctatttaga tattatgaaa    4320
agagtattag aagaattaca aacgtctacc aatacaccat tgaaattcct tgttagagga    4380
aattatatag aaaatataaa taatattgct agaaatgata atatgtttta tgcaaactta    4440
tttgtattaa cagcattatc cagaagagat ccagtaaaag attattataa tgataaaagg    4500
aaaatgttgt ctgctacatt agctgagaaa tttgctaatt ctacatctat gttaataccg    4560
cacaaactta gaaaattagt tgtatctatg aaaaagggac tgttaaaaaa gaaattactt    4620
acatcattgg ccaaggtaaa attattacaa catatacctg cgcacatgtt agaaaatatc    4680
acatcaagta tacgtttcac aactcatacc atagcaacaa tgcaaattat acaaaatgct    4740
aaatatatgt ccaagcacaa ttttttctcag tatgatagta agggtatgtt agctagacaa    4800
atattcacaa agggtggttt tgcagaatat gcagataatt taatggcaaa atggttttct    4860
aaaggttttg aagaatataa aagagaacaa attgaaaatt tcaaaatgga aaattccatt    4920
gattctgaat taaaagattc cgaaagagaa gatgaaaatg atagttcaga agaaagtgcc    4980
aagaaaaaat tacaagatct tcaattagaa gaaagagaaa aaatgaaaaa agagaacagt    5040
ttattattta atcaaagtga taaatgggat caatttataa ataaggaact tgtaagagca    5100
ttaggtttat ggttagaatt taatgataat ccaactaatg catcttcgtt tgtttataaa    5160
gtagtagaag atagtaaaca tttattagaa aataacatag ataataatat tatttttttca    5220 agaacagtaa aaccaactaa acaaacagct ttcagaagat tctttaataa aatattatct    5280
cttggaaata tgcttttaag aaagcctagt tttagagtag aacatgcatt atggtttggt    5340
gcaactatag atataaaaaa agcatttata ttattagaaa aagtaagtga attacataaa    5400
atgttaaata tcaggatga atcatggtta attaatgaag cttttataga aattgttgat    5460
catgtcgtag atttaagtac atataacat gtacgagaac catttggtgt tgcaagaaat    5520
cctggaatga tggcaataaa tcctaaaatat gcagaattat ctcatgaaaa tcgacttaga    5580
gaattacaaa attctatgtg tgctgatcat tgttcttctg tatggaaagt tatatcttct    5640
tttgcattac accatttaaa gaatcctgat agtttacata catatgaaag caagttttct    5700
```

```
aaaaattctt ttggtaacaa aattgatgat aaagattttg ttcataattt taagatgata    5760
ctaggaggag atgcagtttt acattatttt gataatttat taccaaaaac aatgaaaaag    5820
gatttgaaag caatgaaata tggtgtatca ttaacatctg catattcact caaattaact    5880
aaaattattt ttagtcaaat gcaattacct tacttaagtc aaatgtttta tatgcaagct    5940
ccatattttg gtcattttat aggaaaatgg caaaaaaaaa gacaacaaag cagacttaaa    6000
gaaatcatgt cttttatgac tcttggaagt ttatctgctt atacactttt tagtgctatg    6060
gatataacac aacaagctaa agatataggt gcaggaccag tagctagctg ttttacaact    6120
agaatgtctc ctccacaaca aatatgttta aattcagttg ttaatacggc attatctact    6180
tccactcaat cggctatgaa atgtgttttc tctgttggtc tctttgcatc tatagggcca    6240
tacttatttg ctcctatggc aggtttagct gtatggaata tattaaaatc tgaattcaag    6300
gttttacaaa gaatagatat ggcattaaaa aatgtttttca aaatatgtg gaataaattc    6360 ttatccctaa aaggaattag taaattaaga ggtatttta agagaaagaa agctatgaaa    6420
aaaaaaatta tagaaaatgc cacacgcaag atgaatgaca tgaagaacaa cccagaaaag    6480
gccaaggctc ataaaatggc actaaaaaaa attaataact attctaaagg aagctaccat    6540
tacatatcat acgcgaaaat aagaatataa                                      6570

<210> SEQ ID NO 6
<211> LENGTH: 2189
<212> TYPE: PRT
<213> ORGANISM: Plasmodium falciparum

<400> SEQUENCE: 6

Met Leu Lys Phe Phe Ile Phe Ile Leu His Ile Tyr Leu Tyr Ile Asp
1               5                   10                  15

Ser Ile Tyr Ser Ser Glu Leu Ser Lys His Val Lys His Asp Thr Asp
            20                  25                  30

Glu Leu Lys Tyr Ala Ser Pro Thr Tyr Asp Pro Lys Lys Gly Thr Lys
        35                  40                  45

Val Ile Phe Tyr Met Pro Gly Asn Glu Gln Gly Val Ile Pro Asn Asn
    50                  55                  60

Ile Gln Asn Lys Gln His Gly Thr Ser Ile Tyr Pro Ala Ile Glu Tyr
65                  70                  75                  80

Pro Thr Thr Lys Tyr Pro Ala Ile Glu Tyr Pro Gly Ser Glu Met Asn
                85                  90                  95

Asn Gly Lys Thr Gly Thr Thr Asn Ser Gly Ile Tyr Asn Lys Ala His
            100                 105                 110

Gly Ser Ser Asn Asp Tyr Asn Ala Ser Asn Ser Gln Asp Lys Thr Ile
        115                 120                 125

Asn Leu His Ile Asp Glu Asn Asn Ser Asn Asn Ser Tyr Gln Pro Tyr
    130                 135                 140

Asp Ser Asn Asn Thr Asn Asn Thr Asn Ser Asn Asn Asn Ser Asn
145                 150                 155                 160

Asn Asn Ser Asn Asn Asn Ser Asn Asn Asn Ser Asn Asn Tyr Ser Asn
                165                 170                 175

Asn Asn Ser Asn Thr Asn Ser Asn Thr Asn Ser Asn Thr Ser Asn
            180                 185                 190

Asn Asn Thr Thr Asn Tyr Asp Leu Asn Ser Glu Tyr Glu Lys Ile Arg
        195                 200                 205

Arg Lys Glu Glu Glu Ala Ala Arg Arg Ile Glu Arg Glu Arg Arg Ala
```

```
                    210                 215                 220
Asp Ile Asn Arg Lys Asn Gln Asp Asn Ser Asn Lys Tyr Asn Asn
225                 230                 235                 240

Glu Gln Asn Gly Gly Tyr Glu Ser Asp Gly Asn Ser Pro Asn Ser Arg
                    245                 250                 255

Val Asn Ile Asn Ile Thr Asn Asn Gly Thr His Gly Asn Pro His Asn
                260                 265                 270

Asn Asn Ser Tyr Gly His Lys Asn Asn Met His Asn Thr Thr Asn Gly
            275                 280                 285

Asn Tyr Ala Asn Gly Asn Tyr Ala Asn Gly Asn Tyr Ser Lys Gly Asp
        290                 295                 300

Tyr Thr Asn Gly Asp Tyr Thr Asn Gly Asp Tyr Thr Asn Gly Asp Tyr
305                 310                 315                 320

Thr Asn Gly Ile Asn Asn Asn Met His Gly Lys Asn Asn Tyr Asn Thr
                325                 330                 335

Ala Asn Gly Glu Tyr Val Asn Gly Ala Tyr Asp Gly Leu Asn Asn Gly
                340                 345                 350

Ser Tyr Lys Leu Ile Gly Asn Leu Asn Asn Asn Gln Asn Val Asp Asn
            355                 360                 365

Ser Tyr Asn Gln Gly Asn Glu Asn Asp Lys Thr Tyr Thr Ser Asn Tyr
        370                 375                 380

Asn Ile Asn Leu Glu Asp Asn Lys Asn Ser Pro Asp Asn Asn Gln Asn
385                 390                 395                 400

Tyr Ile Ser Thr Phe Asn Lys Asp Ile Gly Pro Asn Lys Ser Glu Arg
                405                 410                 415

Ser Tyr Tyr Asp Val Tyr Gly Arg Glu Tyr Asp Asp Asn Lys Tyr Asn
                420                 425                 430

Pro Tyr Asn Lys Thr Asn Asn His Asn Thr Asn Gln Asn Gly Ser Thr
            435                 440                 445

Thr Tyr Gly Ser Asn Ala Asn Gly Thr Tyr Gly Pro Asn Gly Thr Tyr
        450                 455                 460

Gly Ser Asn Gly Thr Tyr Glu Pro Asn Glu Ser Tyr Gly Pro Asn Gly
465                 470                 475                 480

Ala Tyr Gly Pro Asn Gly Thr Tyr Gly His Asn Gly Lys Tyr Gly Ser
                485                 490                 495

Lys Gly Thr Tyr Gly Asn Asn Glu Thr Pro Tyr Tyr Val Glu His Pro
            500                 505                 510

Glu Tyr Asp Asn Gly Lys Ser Met Ser Asp Phe His Val Lys Asp Ser
        515                 520                 525

Lys Asp Asn Ile Gly Pro Gly Asp Tyr Pro Asn Leu Tyr Gln Asn
530                 535                 540

Ile Tyr Gly Asn Glu Lys Asn Pro Asn Ile Phe Pro Gly Ser Pro Arg
545                 550                 555                 560

Asn Ile Asn Val Tyr Ser Val His His Ile Pro Asn Asn Gly Ala Asn
                565                 570                 575

Gly Gly Leu Asn Ser Gly Ala Asn Gly Gly Leu Asn Asn Gly Ala Asn
                580                 585                 590

Asp Gly Leu Asn Asn Gly Ala Asn Gly Gly Leu Asn Asn Gly Ala Asn
            595                 600                 605

Gly Gly Leu Asn Asn Gly Ala Asn Gly Gly Leu Asn Asn Gly Met Asn
        610                 615                 620

Asn Gly Met Asn Asn Gly Met Asn Asn Gly Met Asn Asn Gly Met Asn
625                 630                 635                 640
```

```
Asn Gly Met Asn Asn Gly Met Asn Asn Gly Gly Leu Asn
            645                 650             655
Asn Gly Met Asn Asn Gly Met Asn Asn Gly Met Asn Asn Gly Met Asn
            660                 665             670
Asn Gly Ile His Asp Asp Leu Tyr Asn Ser Glu Asn Ser Thr Phe Asn
            675             680                 685
Asn Gly Leu Asn Asn Ser Gly Arg Thr Gly Leu Asn Asn Ala Tyr Pro
    690                 695                 700
His Asn Gly Met Leu Asn Asn Gly Thr Glu Tyr Asn Val His Tyr Gly
705                 710                 715                 720
Asn Ser Asp Ser Asn Thr Asn Asp Ser Met Leu Asn Glu Asn Tyr
            725                 730                 735
Tyr Ser Asp Ser Asp Tyr Asp Asp His Thr Pro Gly Asn Lys Lys Lys
            740                 745                 750
Val Tyr Lys Ser Val Ala Glu Arg Asn Lys Lys Ser Ala Ser Gln Asp
            755                 760                 765
Ser Leu Gly Ala Gly Phe Ser Asp Ser Asp Ser Asp Ser Glu Tyr Glu
    770                 775                 780
Val Val Asp Gly Glu Asn Lys Lys Tyr Lys Lys Asn Lys Glu Asn
785                 790                 795                 800
Asn Glu Lys Asp Lys Tyr Glu Asn Asn Trp Asp Ser Asn Asn Tyr Asn
                805                 810                 815
Ser Asp Asn Glu Ile Lys Asp Gly Tyr Leu Ser Glu Ser Glu Arg Glu
            820                 825                 830
Tyr Ala Arg Asn Lys Ala Asn Glu Ile Glu Asp Lys Met Lys Lys Gly
            835                 840                 845
Glu Tyr Ser Arg Lys Tyr Lys Asn Ser Lys Ser Asn Glu Ser Gly Tyr
            850                 855                 860
Ala Ser Lys Gln Thr Ser Asp Ser Asp Asp Ser Asp Ile Glu Ala Asn
865                 870                 875                 880
Ala Phe Tyr Val Asp Asn Gly Gln Glu Met Leu Ile Lys Glu Lys Glu
                885                 890                 895
His Tyr Ser Ser Asp Ser Glu His His Lys Glu Glu Ser Ala Ser Ile
                900                 905                 910
Gly Asn Leu Asn Val Phe Phe Pro Ala Glu Asn Tyr His Phe Ser Thr
            915                 920                 925
Tyr Met Gly Phe Asp Arg Arg Ser Phe Leu Pro Ser Asn Glu Ile Glu
            930                 935                 940
Leu Glu Lys Met Ile Gly Ala Asn Phe Ser Asn Glu Val Lys Asn Tyr
945                 950                 955                 960
Cys Ser Arg Gln Asn Val Ala Gln Lys Ile Gly Asp Tyr Leu Asn Ile
                965                 970                 975
Ser Phe Glu Tyr Ser Arg Ala Leu Glu Glu Leu Arg Ser Glu Met Ile
            980                 985                 990
Leu Asp Phe Asn Lys Arg Lys His Leu Thr Asn Asn Thr Asp Asp Thr
                995                 1000                1005
Ile Leu His Met Ile Glu Asn Ala Glu Lys Arg Lys Asn Asp Pro
            1010                1015                1020
Asn Tyr Lys Glu Ala Tyr Glu Asn Lys Asp Tyr Ala Asn Asn Ala
            1025                1030                1035
Asn Ile Phe Met Asn Glu Tyr Ser Asn Pro Leu Ser Thr Lys Tyr
            1040                1045                1050
```

```
Asn Lys Ile Leu Lys Glu Tyr Leu Cys His Leu Phe Val Asn Asn
1055                1060                1065

Pro Gly Thr Lys Pro Leu Glu Arg Leu Tyr Tyr Asn Ser Leu Ala
1070                1075                1080

Leu Gly Glu Leu Val Glu Pro Ile Arg Asn Lys Phe Lys Ser Leu
1085                1090                1095

Ala Ser Ser Thr Ile Asp Phe Asn Tyr Glu Ile His Met Ala Ser
1100                1105                1110

Ala Ser Asn Ile Tyr Leu Leu Ala His Phe Leu Val Leu Ser Leu
1115                1120                1125

Ala Tyr Leu Ser Tyr Asn Glu Tyr Phe Thr Thr Gly Thr Lys Ser
1130                1135                1140

Phe Tyr Ser Leu Pro Thr Ile Leu Thr Ala Asn Ser Asp Asn Ser
1145                1150                1155

Phe Phe Met Leu Asn Glu Met Cys Asn Ile His Tyr Asn Pro Asn
1160                1165                1170

Lys Asn Phe Lys Lys Asp Ile Thr Phe Ile Pro Ile Glu Ser Arg
1175                1180                1185

Pro Lys Arg Thr Thr Thr Phe Tyr Gly Glu Arg Arg Leu Thr Cys
1190                1195                1200

Asp Leu Leu Glu Leu Val Leu Asn Ala Ile Met Leu Ile Asn Ile
1205                1210                1215

Asn Glu Ile Asn Asn Val Phe Ser Asn Asn Asn Val Asp Gly Tyr
1220                1225                1230

Glu Asn Ser Leu Ser Phe Ser His Asn Ala Ile Arg Ile Phe Ser
1235                1240                1245

Lys Val Cys Pro Lys Ile Asn Asn Asp Asn Val Leu Lys Cys Glu
1250                1255                1260

Phe Glu Glu Ser Ser Leu Tyr Asn Pro Lys Ile Ile Lys Asn Asp
1265                1270                1275

Thr Ser Glu Lys Ser Ser Gln Lys Asn Leu Lys Lys Ala Phe Asp
1280                1285                1290

Leu Leu Arg Thr Tyr Ala Glu Ile Glu Gly His Ser Ala Glu Gly
1295                1300                1305

Ser Thr Ser Pro Tyr Tyr Val Ser Leu Ile Leu Asp Asp Met Lys
1310                1315                1320

Tyr Asn Asp Phe Tyr Lys Tyr Thr Leu Trp Tyr Glu Pro Arg Glu
1325                1330                1335

Leu Ile Tyr Gly Asp Ile Arg Gly Met Gln Met Lys Lys Lys Lys
1340                1345                1350

Lys Thr Lys Tyr Ile Tyr Asn Asp Phe Met Lys Lys Ser Thr Gln
1355                1360                1365

Leu Lys Lys Lys Leu Ile Lys Asn Asp Leu Lys Tyr Asn Leu Lys
1370                1375                1380

Ser Lys Gly Leu Val Phe Leu Tyr Ala Met Ile Asp Lys Tyr Gly
1385                1390                1395

Ser Ile Leu Asn Lys Ser Gln Lys Ala Lys Val Gln Phe Leu Asn
1400                1405                1410

Ser Thr Ser Ser Ile Arg Tyr Tyr Leu Tyr Leu Asn Lys Val Ile
1415                1420                1425

Phe Lys Ser Ala Lys Thr Tyr Leu Asp Ile Met Lys Arg Val Leu
1430                1435                1440

Glu Glu Leu Gln Thr Ser Thr Asn Thr Pro Leu Lys Phe Leu Val
```

-continued

```
            1445                1450                1455
Arg Gly Asn Tyr Ile Glu Asn  Ile Asn Asn Ile Ala  Arg Asn Asp
    1460                1465                1470

Asn Met Phe Tyr Ala Asn Leu  Phe Val Leu Thr Ala  Leu Ser Arg
    1475                1480                1485

Arg Asp Pro Val Lys Asp Tyr  Tyr Asn Asp Lys Arg  Lys Met Leu
    1490                1495                1500

Ser Ala Thr Leu Ala Glu Lys  Phe Ala Asn Ser Thr  Ser Met Leu
    1505                1510                1515

Ile Pro His Lys Leu Arg Lys  Leu Val Val Ser Met  Lys Lys Gly
    1520                1525                1530

Leu Leu Lys Lys Lys Leu Leu  Thr Ser Leu Ala Lys  Val Lys Leu
    1535                1540                1545

Leu Gln His Ile Pro Ala His  Met Leu Glu Asn Ile  Thr Ser Ser
    1550                1555                1560

Ile Arg Phe Thr Thr His Thr  Ile Ala Thr Met Gln  Ile Ile Gln
    1565                1570                1575

Asn Ala Lys Tyr Met Ser Lys  His Asn Phe Ser Gln  Tyr Asp Ser
    1580                1585                1590

Lys Gly Met Leu Ala Arg Gln  Ile Phe Thr Lys Gly  Gly Phe Ala
    1595                1600                1605

Glu Tyr Ala Asp Asn Leu Met  Ala Lys Trp Phe Ser  Lys Gly Phe
    1610                1615                1620

Glu Glu Tyr Lys Arg Glu Gln  Ile Glu Asn Phe Lys  Met Glu Asn
    1625                1630                1635

Ser Ile Asp Ser Glu Leu Lys  Asp Ser Glu Arg Glu  Asp Glu Asn
    1640                1645                1650

Asp Ser Ser Glu Glu Ser Ala  Lys Lys Lys Leu Gln  Asp Leu Gln
    1655                1660                1665

Leu Glu Glu Arg Glu Lys Met  Lys Lys Glu Asn Ser  Leu Leu Phe
    1670                1675                1680

Asn Gln Ser Asp Lys Trp Asp  Gln Phe Ile Asn Lys  Glu Leu Val
    1685                1690                1695

Arg Ala Leu Gly Leu Trp Leu  Glu Phe Asn Asp Asn  Pro Thr Asn
    1700                1705                1710

Ala Ser Ser Phe Val Tyr Lys  Val Val Glu Asp Ser  Lys His Leu
    1715                1720                1725

Leu Glu Asn Asn Ile Asp Asn  Asn Ile Ile Phe Ser  Arg Thr Val
    1730                1735                1740

Lys Pro Thr Lys Gln Thr Ala  Phe Arg Arg Phe Phe  Asn Lys Ile
    1745                1750                1755

Leu Ser Leu Gly Asn Met Leu  Leu Arg Lys Pro Ser  Phe Arg Val
    1760                1765                1770

Glu His Ala Leu Trp Phe Gly  Ala Thr Ile Asp Ile  Lys Lys Ala
    1775                1780                1785

Phe Ile Leu Leu Glu Lys Val  Ser Glu Leu His Lys  Met Leu Asn
    1790                1795                1800

Asn Gln Asp Glu Ser Trp Leu  Ile Asn Glu Ala Phe  Ile Glu Ile
    1805                1810                1815

Val Asp His Val Val Asp Leu  Ser Thr Tyr Lys His  Val Arg Glu
    1820                1825                1830

Pro Phe Gly Val Ala Arg Asn  Pro Gly Met Met Ala  Ile Asn Pro
    1835                1840                1845
```

Lys Tyr Ala Glu Leu Ser His Glu Asn Arg Leu Arg Glu Leu Gln
1850                1855                1860

Asn Ser Met Cys Ala Asp His Cys Ser Ser Val Trp Lys Val Ile
1865                1870                1875

Ser Ser Phe Ala Leu His His Leu Lys Asn Pro Asp Ser Leu His
1880                1885                1890

Thr Tyr Glu Ser Lys Phe Ser Lys Asn Ser Phe Gly Asn Lys Ile
1895                1900                1905

Asp Asp Lys Asp Phe Val His Asn Phe Lys Met Ile Leu Gly Gly
1910                1915                1920

Asp Ala Val Leu His Tyr Phe Asp Asn Leu Leu Pro Lys Thr Met
1925                1930                1935

Lys Lys Asp Leu Lys Ala Met Lys Tyr Gly Val Ser Leu Thr Ser
1940                1945                1950

Ala Tyr Ser Leu Lys Leu Thr Lys Ile Ile Phe Ser Gln Met Gln
1955                1960                1965

Leu Pro Tyr Leu Ser Gln Met Phe Tyr Met Gln Ala Pro Tyr Phe
1970                1975                1980

Gly His Phe Ile Gly Lys Trp Gln Lys Lys Arg Gln Gln Ser Arg
1985                1990                1995

Leu Lys Glu Ile Met Ser Phe Met Thr Leu Gly Ser Leu Ser Ala
2000                2005                2010

Tyr Thr Leu Phe Ser Ala Met Asp Ile Thr Gln Gln Ala Lys Asp
2015                2020                2025

Ile Gly Ala Gly Pro Val Ala Ser Cys Phe Thr Thr Arg Met Ser
2030                2035                2040

Pro Pro Gln Gln Ile Cys Leu Asn Ser Val Val Asn Thr Ala Leu
2045                2050                2055

Ser Thr Ser Thr Gln Ser Ala Met Lys Cys Val Phe Ser Val Gly
2060                2065                2070

Leu Phe Ala Ser Ile Gly Pro Tyr Leu Phe Ala Pro Met Ala Gly
2075                2080                2085

Leu Ala Val Trp Asn Ile Leu Lys Ser Glu Phe Lys Val Leu Gln
2090                2095                2100

Arg Ile Asp Met Ala Leu Lys Asn Val Phe Lys Asn Met Trp Asn
2105                2110                2115

Lys Phe Leu Ser Leu Lys Gly Ile Ser Lys Leu Arg Gly Ile Phe
2120                2125                2130

Lys Arg Lys Lys Ala Met Lys Lys Lys Ile Ile Glu Asn Ala Thr
2135                2140                2145

Arg Lys Met Asn Asp Met Lys Asn Asn Pro Glu Lys Ala Lys Ala
2150                2155                2160

His Lys Met Ala Leu Lys Lys Ile Asn Asn Tyr Ser Lys Gly Ser
2165                2170                2175

Tyr His Tyr Ile Ser Tyr Ala Lys Ile Arg Ile
2180                2185

<210> SEQ ID NO 7
<211> LENGTH: 1479
<212> TYPE: PRT
<213> ORGANISM: Toxoplasma gondii

<400> SEQUENCE: 7

Met Thr Lys Arg Ala Gly Leu Pro Leu Gly Arg Ala Phe Leu Val Leu

```
1               5                   10                  15
Ile Leu Leu Ser Ala Asp Ser Leu Phe Ser Phe Pro Arg
            20                  25              30
Ser Ala Leu Gln Leu Phe Ser Ser Val Leu Phe Thr Asp Ala Ala Glu
            35                  40              45
Pro Asp Ser Asp Ala Thr Pro Gly Leu Arg Pro Gln Pro Ser Pro Arg
        50                  55              60
Thr Phe Arg Pro Thr Gly Tyr Gln Arg Ile Glu Val Lys Thr Val Asp
65                  70              75                  80
Glu Glu Leu Pro Glu Asp Leu Lys Val Tyr Thr Ala Ser Thr Arg Gly
                85                  90              95
Ser Ser Ser Arg Thr Phe Glu Val Arg Asn Ala Gly Arg Gln Glu
                100                 105             110
Gly Phe Thr Leu Ser Val Leu Thr Ala Gly Pro Leu Pro His Gly
                115                 120             125
Ser Trp Ser Trp Ser Gly Thr Pro Pro Glu Val Gln Thr Thr Gly Gly
            130                 135             140
Ser Gln Ile Ser Phe Gly Trp Val Pro Asp Thr Glu Thr Pro Ser Leu
145                 150                 155                 160
Pro Glu Arg Asn Leu Leu Gln Leu Lys Arg Met Leu Arg Asp Glu Gly
                165                 170                 175
Leu Ile Glu Ala Val Gln Leu Arg Ala Ala Glu Lys Gly Cys Pro Val
                180                 185                 190
Ala Val Leu His Asn Leu Arg Gln Leu Pro Val Asn Phe Arg Glu Val
                195                 200                 205
Leu His Glu Glu Tyr Glu Ser Arg Ser Asn Pro Ala Lys Met Tyr Glu
        210                 215                 220
Val Ala Asn Ser Tyr Val Gln Gln Arg Gly Ser Asp Ala Ala Arg Trp
225                 230                 235                 240
Ser Val Ser Gln Ser Val Glu Leu Ser Leu Glu Met His Ala Thr
                245                 250                 255
Ser Thr Thr Asp Pro Arg Gly Ser Ser Ala Val Pro Ser Phe Leu Glu
                260                 265                 270
Thr Gly Pro Gln Val Arg Val Ala Met Thr Asp Ala Val Pro Ser Gly
            275                 280                 285
Ile Arg Val Tyr Ala Thr Pro Pro Ala Pro Arg Pro Val Pro Val Gln
            290                 295                 300
Ser Asn Gln Thr Glu Lys Glu Arg Ser Pro Thr Ser Lys Arg Leu Val
305                 310                 315                 320
Gly Met Gln Leu Gly Leu Tyr Leu Ile Cys Lys Leu Ala Ala Leu Phe
                325                 330                 335
Gly His Pro Thr Leu Phe Leu Asn Pro Tyr Tyr Thr Glu Gln Gln Leu
                340                 345                 350
Leu Glu Ala Val Ala Gln Ala Leu Gly Ile Ala Pro Pro His Arg Gly
                355                 360                 365
Asp Phe Glu Asn Glu Gly Asn Glu Ala Gln Ala Thr Ala Asn Gln His
        370                 375                 380
Asn Gly Ser Ala Asp Gln Leu Leu Ala Ala Ile Glu Ile Phe Arg Leu
385                 390                 395                 400
Gly Pro Asn Pro Tyr Thr Ile Gly His Val Leu Thr Leu Met Ile Ala
                405                 410                 415
Tyr Leu Asp Tyr Glu Ser Phe Phe Gly Ala Ser Pro Ser Lys Pro Phe
            420                 425                 430
```

-continued

His Ser Trp Val Ser Leu Ala Ala Ser Ala Gly Asn Asn Thr Gly Phe
        435                 440                 445

Ala Met Leu Asp Glu Met Cys Asp Asn His Arg Gly Pro Lys Arg Arg
450                 455                 460

Gly Gln Lys His Trp Tyr Gln Thr Gly Gly Ala Arg Lys His Lys Asn
465                 470                 475                 480

Arg Asp Met Leu Pro Leu His Arg Gln Leu Cys Asp Ala Leu Glu Leu
                485                 490                 495

Val Leu Asn Gly Val Gln Gln Ile Gln Ile Asp Leu Met Asp Glu Leu
            500                 505                 510

Gly Lys Tyr Lys Thr Gly Val Glu Pro Leu Val Asp Pro Ala Thr Asn
        515                 520                 525

Ser Ala Arg Ile His Thr Arg Thr Cys Arg Gly Leu Ser Pro Val Cys
    530                 535                 540

Asp Tyr Glu Ala Thr Ile Leu Ala Pro Val Arg Ala Leu Glu Pro His
545                 550                 555                 560

Glu Gln Gln Asp Ser Leu Arg Thr Lys Lys Ala Phe Asn Leu Val Thr
                565                 570                 575

Gly Tyr Gly Ser Gly His Val Gly Gln Ile Thr Gly Ser Ile Ala Glu
            580                 585                 590

Pro Phe Ser His Ser Trp Arg Thr Arg Trp Gly Lys Val Val Ala Asp
        595                 600                 605

Pro Thr Ala Tyr Gly Glu Ile Phe Glu Arg Thr Leu Trp Phe Asp Asp
    610                 615                 620

Arg Glu Leu Met Ala Lys Ser Ser Gly Ala Leu Phe Arg Gln Tyr Asp
625                 630                 635                 640

Arg Ile Ala Lys Asp Ser Met Ser Phe Gly Val Phe Met Asn Val Glu
                645                 650                 655

Asn Gly Leu Leu Lys Lys Asp Met Arg Ser Lys Leu Glu Ala Tyr Ile
            660                 665                 670

Ser Gln Arg Lys Ser Phe Val Glu Lys Arg Gln Gln Ser Arg Phe Ala
        675                 680                 685

Lys Leu Arg Lys Lys Ile Pro Glu Asn Asp Pro Tyr Ala Leu Arg Ala
    690                 695                 700

Ala Ile Phe Leu Ala Leu Asn Ser Arg Thr Phe Cys Ala Gln Pro Thr
705                 710                 715                 720

Ser Phe Leu Ser Ser Phe Arg Thr Phe Leu Thr Asn Gln Tyr His Lys
                725                 730                 735

Leu Ser Gln Gly Arg Asn Leu Pro Arg Ser Gln Arg Ser Leu Met Ala
            740                 745                 750

Phe Met Arg Thr Gly Gln Val Lys Phe Phe Glu Trp Cys Ser Phe
        755                 760                 765

Asp Pro Leu Ala Val Asn Ala Leu Phe Leu Phe Arg Phe Ala Val Ser
    770                 775                 780

Gly Thr Asp Pro Ala Ala Leu His Asp Arg Gln His Thr Arg Val Ser
785                 790                 795                 800

Arg Asn Lys Lys Thr Met Arg Ile Leu Asn Ser Lys Trp Thr Pro Ala
                805                 810                 815

Val Leu Lys Lys Leu Met Arg Lys Val Asn His Lys His Met Ala Arg
            820                 825                 830

Glu Ala Lys Ala Leu Leu Leu Arg Ser Leu Asp Pro Thr Val Leu Ser
        835                 840                 845

```
Ser Ile Val Thr Ala Phe Asp Phe Ile Thr His Thr Gln Ala Asn Leu
            850                 855                 860

Glu Val Asn Gln Asn Ala Phe Met Tyr His Glu Val Arg Ala Arg Glu
865                 870                 875                 880

Val Ser Arg Gln Ser Ala Ala Glu Lys Gly Ser His Arg Leu His Glu
                885                 890                 895

Arg Gly Leu Val Arg Glu Thr Asp Asp Met Ile Lys Arg Trp Ala Glu
            900                 905                 910

His Gly Ile Pro Gly Asp Ile Lys Arg Leu Ala Arg Gly Glu Lys
            915                 920                 925

Leu Pro Glu Gly Met Ser Phe Gly Gly Ile Pro Ile Pro Asn Leu Thr
930                 935                 940

Asn Trp Asp Ala Gln Leu Asn Ser Lys Trp Leu Glu Ala Tyr Asn Ala
945                 950                 955                 960

Tyr Leu Arg His Pro Tyr Gly Arg Ala Ala Leu Asn Ala Arg Asp Pro
                965                 970                 975

Val Ala Leu Leu Val Lys Asp Ser Arg Asp Arg Leu Gln Ala Glu Ala
                980                 985                 990

Glu Gly Thr Ile Phe Leu Gly Arg Ile Ala Lys Arg Val His Gln Ser
            995                 1000                1005

Lys Asn Leu Leu Arg Arg Ala Gly Arg Ala Leu Lys Thr Phe Phe
    1010            1015            1020

Leu Ser Leu Leu Arg Glu Asn Glu Arg Ser Glu Tyr Ala Val Trp
    1025            1030            1035

Phe Gly Val Lys Val Asp Met Arg Gln Val Ile Gln Thr Cys Arg
    1040            1045            1050

Gln Ile Asn Ser Val Ala Glu Val Val Lys Asn Asp Arg Leu Tyr
    1055            1060            1065

Asp Phe Ile Thr Asp Gly Trp Met Glu Leu Val Lys Asp Val Val
    1070            1075            1080

Ala Gly Tyr Thr Lys Ala Ser Val Arg Val Pro Gly Phe Asp Thr
    1085            1090            1095

Ile Ser Ala Ala Asn Glu Gln Leu Arg Lys Glu Gly Val Ala Ala
    1100            1105            1110

Ala Thr Ala Arg Asn Gln Gly Phe Leu Ser Ile His Tyr Asp Tyr
    1115            1120            1125

Ala Asn Leu Pro Glu Glu Glu Arg Lys Lys Glu Phe Gln Arg Ser
    1130            1135            1140

Met Cys Met Glu Gln Cys Glu Ala Leu Trp Lys Leu Val Met Ala
    1145            1150            1155

Phe Val Met Pro Asn Leu Gln Asn Pro Lys Lys Leu Lys Gly Tyr
    1160            1165            1170

Glu Lys Asp Phe Ser Gly Ala Lys Glu Ile Glu Lys Leu Asn Ser
    1175            1180            1185

Pro His His Val Asn Ala Phe Arg Phe Ser Leu Ser Val Gln Ile
    1190            1195            1200

Asp Phe Phe Asp Asn Met Leu Asp Lys Thr Ser Lys Lys Asn Leu
    1205            1210            1215

Lys Ala Met Lys Phe Gly Ala Ser Thr Trp Phe Thr Tyr Ala Met
    1220            1225            1230

Lys Leu Ala Gly Gln Val Asn Ser Glu Met Gly Asn Pro Asn Leu
    1235            1240            1245

Gly Thr Ala Leu Tyr Met Gln Ala Ala Tyr Tyr Gly Asn Tyr Ile
```

```
                    1250                1255                1260
Arg Lys  Trp Met Glu Gln Arg  Arg Lys Ser Arg Lys  Gln Ala Ile
    1265             1270                 1275

Ile Gly  Val Leu Thr Leu Gly  Met Met Gly Leu Tyr  Ala Leu Leu
    1280             1285                 1290

Asn Val  Ala Asp Ile Val Gln  His Met Glu Asp Ile  Gly Gly Ala
    1295             1300                 1305

Pro Pro  Val Ser Cys Val Thr  Asn Glu Ile Leu Gly  Val Thr Cys
    1310             1315                 1320

Ala Pro  Gln Ala Ile Ala Lys  Ala Thr Thr Ser Ala  Ala Arg Val
    1325             1330                 1335

Ala Thr  Gln Asp Phe Leu Lys  Val Gly Leu Phe Ala  Gly Met Ala
    1340             1345                 1350

Pro Tyr  Leu Met Leu Pro Met  Ala Val Val Ser Val  Trp Asn Ile
    1355             1360                 1365

Leu Lys  Ser Glu Ile Lys Val  Leu Leu Gln Phe Glu  Met Ala Leu
    1370             1375                 1380

Lys His  Thr Phe Thr Arg Leu  Lys Arg Trp Leu Ala  Ala Pro Phe
    1385             1390                 1395

Lys Asn  Trp Trp Ala Lys Arg  Gly Arg Leu Lys Asp  Ala Leu Phe
    1400             1405                 1410

Arg Arg  Ala Ser Gln Thr Tyr  Arg Lys Thr Glu Gln  Glu Thr Lys
    1415             1420                 1425

Gln Pro  Pro Arg Pro Arg Asn  Leu His Asn Pro Ser  Ser Trp Gly
    1430             1435                 1440

Asp Thr  Glu Leu Asp Ser Leu  Gly Val Pro Pro Glu  Pro Phe Val
    1445             1450                 1455

Gln Asp  Phe Glu Ile Lys Tyr  Thr Thr Pro Val Phe  Pro Met Ser
    1460             1465                 1470

Ala Pro  Leu Ile Lys Ala
    1475

<210> SEQ ID NO 8
<211> LENGTH: 4440
<212> TYPE: DNA
<213> ORGANISM: Toxoplasma gondii

<400> SEQUENCE: 8
atgactaaac gcgctggcct gcccttgggc agggcatttc ttgtcctgat tcttctatct      60
gcagcggatt cactcttctt ctctagcttt ccccgctctg ctctccaact ctttcttcc     120 gttcttttca cagacgctgc agaacctgac tcggacgcca ccccgggtct gcggccgcaa     180
cccagcccac gcactttccg gcctacgggg tatcagcgaa tcgaggtgaa aactgtcgat     240
gaagagttac ccgaagacct caaagtttac accgcgtcga cacgcggatc ttcgtctcgt     300
acattcgaag tcagaaatgc cggaggccga caggaaggct ttactttgtc cgtcctcacc     360
gccggcgggc tctgccgcca cggttcctgg tcttggagcg aaccccctcc ggaagtgcag     420
accacggggg gttctcaaat cagtttcggc tgggtgccag acaccgaaac gccgagtttg     480
cccgaacgga atcttctcca gttgaagaga atgcttcgcg acgagggttt gatcgaggct     540
gttcagctga gggccgcgga aaaggggtgc ccgtggccg ttctgcacaa tctgcggcaa     600
cttccggtga atttccgcga ggttctccac gaggagtacg agagccgcag caaccccgcg     660
aaaatgtacg aagtcgcgaa tagctatgtc caacagaggg gcagcgatgc tgctcgctgg     720
```

```
tcagtctctc agtccgtcga gctttctctc ctggaaatgc atgcgacgtc aaccacggat    780
ccccgcggtt cgagtgccgt cccgtccttt ctggaaactg gacctcaagt gcgagttgca    840
atgactgacg ccgtcccctc aggaattcgc gtgtacgcaa cgcctccggc gcctcgtcca    900
gtgcctgtgc aaagtaacca gacagaaaag gagagaagtc cgacctccaa gcgccttgtt    960
ggtatgcagc tcggcctcta cttgatttgc aagcttgcgg ctcttttggg ccacccgact   1020
ttgtttctaa atccgtacta cacggagcag cagctcctcg aagccgtggc gcaggctctc   1080
gggatcgcgc caccgcaccg cggtgatttc gaaaacgaag gaaatgaagc gcaagcgaca   1140
gccaaccagc acaacgggag cgccgaccag ctgcttgcag ccatcgaaat ctttcgccta   1200
gggccgaatc cctacactat cggtcacgtt ctgaccctga tgattgccta cctggactac   1260
gagtctttct cggagcctc gccgtcaaag ccttttcact cttgggtctc gttggcagct   1320
tctgcgggga acaacacagg cttcgcgatg ctcgacgaaa tgtgcgacaa ccaccgtgga   1380
cctaagcgac gtggacagaa acactggtac cagaccgggg gcgcgaggaa gcacaaaaac   1440
cgagacatgt tgcctctcca ccgccagctg tgcgacgccc tcgaactagt gctcaacggc   1500
gttcagcaga tccaaatcga cctgatggat gaacttggaa aatacaagac tggcgtcgag   1560
cctctcgtcg accccgcaac taacagcgcg agaattcaca ctcgcacctg ccgaggtttg   1620
tccccggtct gcgactacga agcaacaatt ctcgctcctg tgcgcgcttt agagccgcac   1680
gaacaacaag actctctccg taccaagaag gcgttcaacc tggtcacggg atacgggagc   1740
ggtcacgtcg acaaatcac aggaagcatc gccgagccgt ctcgcatag ctggcggacg   1800 cggtggggaa aagttgtggc ggacccaact gcctacggcg aaatcttcga gcgcactctg   1860
tggttcgacg accgcgagtt gatggcgaag agcagcggcg ctctcttcag acaatacgac   1920
agaattgcaa aagactcaat gtctttcggt gtcttcatga acgtcgaaaa cggactcctg   1980
aagaaagaca tgcgcagcaa gttggaggct tacatctcgc aaagaaagag cttcgtcgag   2040
aagagacagc agtcgagatt cgcgaagctt cgaaagaaaa tccccgaaaa cgacccttac   2100
gcactcagag ccgccatctt cctcgcgctc aattctcgga cgttctgcgc gcagccgacg   2160 tcgttttat cgagcttccg gacctttctc acgaaccaat accacaagct aagtcaagga   2220
agaaatctcc cgagatctca gagatcgttg atggcgttca tgcgcaccgg gcaggttaaa   2280
ttctttcaag agtggtgcag cttcgacccc ctcgccgtca acgccctctt tctcttccga   2340
ttcgcggtct ctggaacaga ccccgcggcg ctgcacgaca ggcaacacac ccgtgtcagc   2400
agaaacaaga gacgatgcg gattttgaat ccaagtgga ctcccgcggt gctgaagaag   2460
ctgatgcgaa aagtcaacca caaacacatg gcgcgcgaag cgaaggctct actgcttcgg   2520
agcttggatc cgacagtctt gtcgagcatc gtgacggcgt ttgacttcat cacccacaca   2580
caggcgaacc tggaagtgaa tcagaacgcg ttcatgtacc acgaggtgcg ggcgcgggag   2640
gtttcgcgcc agtcagcggc agagaaaggc tcgcacaggc tgcatgagag gggtctcgtt   2700
cgcgagacag acgacatgat caagaggtgg gcagagcacg gaattccagg ggacatcaag   2760
cgtcgcctgg cacgaggcga gaagcttcca gaagggatgt cgtttggcgg catccccatc   2820
cccaatctga cgaactggga tgcacagctg aattccaagt ggcttgaggc gtacaacgcg   2880
tatctgcgac acccgtacgg ccgagcagca ctgaacgcgc gcgacccagt tgcgttgctc   2940
gtgaaggact cgcgagaccg cctccaggct gaggccgagg gcaccatctt tcttgggcgc   3000
atcgcgaagc gcgtgcacca gagcaaaaac cttctgcgac gagccgggcg ggcgctgaag   3060
actttttttc tgtcgctgct gagagagaac gaacgcagcg agtacgccgt ctggtttggt   3120
```

```
gtgaaggtcg acatgcggca ggtgattcag acctgcaggc aaatcaactc ggtggcggaa    3180
gtcgtgaaga acgaccgcct ctacgatttc atcaccgacg gctggatgga gctcgtgaaa    3240
gacgtcgtcg cagggtacac gaaggcgtcg gtgcgagttc ctggtttcga cacgatttct    3300
gcggcaaacg agcaattgcg gaaggaggga gtagcagctg ccactgcgcg gaaccaaggt    3360
ttcctgtcga ttcactacga ttacgcgaac ctgccggagg aagagcgcaa gaaggagttc    3420
cagcggtcga tgtgcatgga gcagtgcgaa gcgctttgga agctggtcat ggcgttcgtg    3480
atgccgaatc tgcagaatcc gaagaagctg aaggggtacg agaaggactt tcgggagcg     3540 aaggaaattg agaagctgaa cagtccacac acgtgaacg cgttccgctt tagtctctct     3600
gtgcagatcg acttcttcga caacatgctc gacaagacgt ccaaaaagaa tctgaaggcg    3660
atgaagttcg gcgcgagcac ttggttcacc tacgccatga agcttgcggg acaggtcaac    3720
tcggagatgg gcaatccgaa cctcggcact gcgctgtaca tgcaggccgc gtactacggg    3780
aactacattc gaaagtggat ggagcagcgg cggaagtcgc ggaagcaagc cattatcgga    3840
gtcttgacgc tcggcatgat gggtctgtac gcgctgctga atgttgcaga catcgtgcaa    3900
catatggaag acattggcgg cgcgccgccg gtctcctgcg tgacgaacga gatcctcgga    3960
gtcacctgcg cgccgcaggc catcgccaag gccaccacga gcgccgcgag agtggcgacc    4020
caagacttcc tcaaagtcgg cctcttcgca ggcatggcgc cgtacctcat gctgcccatg    4080
gccgtcgtct ccgtctggaa catcctcaag tcggaaatca aggtgttgct gcagttcgaa    4140
atggctctca acacaccttt cacgcgcctc aagaggtggc ttgcggcgcc tttcaagaac    4200
tggtgggcga agcgcggcag actgaaggac gcgctcttcc ggagagcctc gcagacttac    4260
agaaaaacgg aacaggaaac gaagcagccg cctcgaccca gaaatctgca caacccaagc    4320
agctggggag acaccgaact cgacagtctc ggcgtgcctc cagagccctt cgtccaagac    4380
ttcgaaatca agtacacgac ccccgtcttc cccatgagtg cgcctctcat caaagcctga    4440
```

<210> SEQ ID NO 9
<211> LENGTH: 6699
<212> TYPE: DNA
<213> ORGANISM: Plasmodium yoelii

<400> SEQUENCE: 9

```
atgttaaagg ctacaattgg tataatttta tttatatgtg tgaatataga tattatacgt      60
acaacaagta gggacaatgt ggtaaatacc aaatttgtga gacaaaaaag tccaacttat     120
gatccaaaca agaaggggga tgttattttt tatatgcctg aacacaaaga tgaaatacat     180
agagccaata taagagcgc gaatattaat ttaaaaaata cccaccacg taatattaat       240 atagggtaca atacagcccc aggagtaaat catggatttg acagttttc aggcaaatca      300 tcaaatatga ataatggtat aacacatat aagaatcaac caaaacactt tcaatctatg      360
aactaccaga aaaatggacc ctttggaaat aaattagaac aaatgaatat tccagcaaat     420
ttatataata ataagaataa ttcatattat tctggtagca ataatggaaa taataattcc     480
tatggattac atggtaatat atatgataaa ataaatagta gtgtatataa caatagtaaa     540
tataataata gtaattttaa tactgataaa aataataatg ataatgaaaa taataaaacc     600
tataaatcat acttaaattt gtatgtttca gataataaaa tatctcctat tggaaataat     660
ggaaggcctg acatttgat aagtcatttt aacaatccta accaaaaact tgagttttta     720
catggttttg atggattatt taatcaaaac atacctggta tgaaccataa aggtaattat     780
```

```
ggattcaatg gagtaaatat caaaggacag ggaaaaaatg agaaatttga taattatggc      840
caaaatttag gtctaaataa aaccaatgaa tatcaacaaa tgataaatgg caataatatg      900
ggatcagatc atatttatga atccccaaac tttgtaaatg gtaacaatat gggatcagat      960
aatgctggag aataccaaag actggtaaat ggtaataata tgggatcaga tcatatttat     1020
gaatccccaa actttgtaaa tggtaacaat atgggatcag ataatgctgg agaatcccaa     1080
agactagtaa atggtaacaa tatgggatca gataatgctg gagaatcccc aaaattggta     1140
aatggtaata atatgggatc agataatgct ggagaatccc aaaattggt aaatggtaat      1200 aatatgggat cagataatgc tggagaatcc caaagactag taaatggtaa caatatggga     1260
tcagataatg ctggagaatc cccaaaattg gtaaatggta ataatatggg atcagataat     1320
gctggagaat cccaaagact agtaaatggt aataatatgg gatcagataa ttctggagaa     1380
taccaaagac tggtaaatgg taataatatg ggatcagata attctggaga ataccaaaga     1440
ctggtaaatg gtaacaatat gggatcagat catatttatg aatccccaaa ttttgtaaat     1500
ggtaataata tgggatcaga taatgctgga gaataccaaa actgataaa tggtaataat      1560 atgggatcag ataatgctgg agaataccaa agactgataa atggcaataa tatgggatca     1620
gatcatattt atgaatcccc aaattttgta atggtaata atatgggatc agataatgct      1680
ggagaatacc aaagactgat aaatggtaat aatatgggat cagataatgc tggagaatac     1740
caaagactga taaatggcaa taatatggga tcagatcata tttatgaatc ccaaatttt      1800 gtaaatggta ataatatggg atcagataat gctggagaat accaaagact ggtaaatggt     1860
aataatatgg gatcagataa tgctggagaa taccaaagac tggtaaatgg caataatatg     1920
ggatcagatc atatttatga atccccaaat cttgtaaatg gtaataatat gggatcagat     1980
aattctggag aataccaaag actggtaaat ggtaataata tgggatcaga taatgctgga     2040
gaataccaaa gactggtaaa tggcaataat atgggatcag atcatattta tgaatcccca     2100
aatcttgtaa atggtaataa tatgggatca gataattctg gagaataccca aagactggta     2160 aatggtaata atatgggatc agatgattct ggagaatacc aaaaactggt aaatggtaat     2220
aatggtgtga taccaaattt taccggaaat gaccaagaaa tatttaaaaa cattcgtggc     2280
ttgagaccag taaatcatga agagttgtat aaaaataaaa tgaacccatt aatatataat     2340
gcacatggaa tgcaaagtgg taataaaaat ggtgcaccta attccacatc tgattatgta     2400
tctgattata attctgattc tgataccgat tctgattctg attctgattc cgatcttgat     2460
tatgactctg aatcaaatga atcaaatgta tataaaataa aaactaacaa attagaaaat     2520
gacaataaag atggtaatgg aaatgtaaat gatgcaaatt attataaaaa tcaaatagac     2580
atcgcgaata aaaaccatgg gaacagatat aatagtgaaa atgattatgg agatagtatg     2640
cattcggata gtgctttatc ttatgaaaga gatttaagct ctggaaatag acatgtcaaa     2700
gaaggttcta atgatgaaat aaatatattt tatagagata tgctcaaga tagagaaaca     2760 aaagaaaagt taatgaattc gtcagaatcg gataaagatg tagaaaaccc tttaaatata     2820
acaattccag aagaaaatgt aaactatcat ttttccaatt acatgaattt tgataaaaaa     2880
aatatactta cttccaatga agaagaatta ttaaaaatga taggacctga ttttcaaaa     2940 gaagtaagta attattgtag taaaaaatca atattccctt cgaatggtaa atatttggat     3000 gtttctttg aatattctaa agaattagga aaattaagag aaaaaatgat gagtggacta     3060
tttaaaaaga aaggcaagtt agttactaaa gaaaataata ttttaaaaca aatagaaaac     3120
tctttaaaaa tggattatct ggaaagacag cagggatatg taaattatgg ttcaaaatct     3180
```

```
aatgaattaa aaaatgacga agaatcgatg ttaagcaatg aatataataa attattagaa    3240
gaatatattt gtcatatact ttctaataat cctggtaaaa ctcagtttga aaaattatat    3300
taccataacc tagcattagg agaaataatg aagccaataa aaacaaaata taaaaatgca    3360
gcaacattgt ctattgcatt aaattatgaa atatacattg tttcttcttc aaatatttat    3420
ttatttggac atatgttatt attatcatta gcatatcttt cttataattc atattttaca    3480
aaaggaacaa aatcatttta ctcaatggaa acaatgttgt tagcaaattc agattattcc    3540
ttttttatgt acaatgaaat gtgtaatgtt tattatagac ytaataaatc atttaaaaaa    3600
gatttaacat ttattccaat cgaattaaga ccaggaagat atactacata tgtcggagaa    3660
aggaaaataa tatgtaacac attagaacta atattaaacg ccatatctct tataaacatt    3720
aatgaaattt acaatgtttt tcataagaat aatgtttatg gatatgaaaa ttcggtatct    3780
ttttcaaata atgcaataag agtattttca caagtttgcc caagaaacat ggaaaaaaat    3840
attataaatt gtagttttga aaaatctact ttatataaag caaatgctcc agaagataca    3900
aatcaaaacg aatatcaaag acaaaatcaa ataaaaaatc aaaatgaatt gaaaaaagca    3960
tttgatctat taaatacatt tagtgaaata gaaagttttt caataaataa ttatcaaaat    4020
agttactata taaagcttat tatggaacaa aacttatata ccgattttta taaatattta    4080
ttttggtatg ataatagaga gcttataaaa acacatgaaa taaacggcaa aaaaaacaca    4140
aaaaaaactt caaattatat ttatgatcaa tatataaaaa ctaatagatt attagaaaaa    4200
aaattcaatg tactttctaa acataatttg aaatcgaaag gattattagc atttcattca    4260
ttaatagata gatattcaga atttgttaaa aataagaaaa ttagaaatct atatttaaaa    4320
tttgtttcat atgctcgaca ctttttattt atgaacaata caatgaaatc tctaaacaag    4380
tcagatctcg attttatgaa aatgatattc gaagaattac aaaatgaaac aaaagttcca    4440
ctaaaactta tagtacgagg taattatatg aagtctatga atgatatagc taaaaaagaa    4500
aacctttttt ttattaattt atttatatta tcattatttt caaataaaaa tccagttaaa    4560
aacttttata atggaaagcg agaaatgtta aaagcttcac tttctgaaaa atttgcgacg    4620
tctacatcgg cttttattcc acataaactt agaagaattg tagttggaat gaaaaaggga    4680
tttttaaaaa gaaagttgtt aaaaacatta atgaaaaatc gacttttaca acatatacca    4740
atcgatctgt tagaaaatat tatgactact ttccgattta caacacatgc tatcgcaact    4800
agtgaattag ctcaaaatgc acatcgtaca tcaaaatatt tgaattctaa taacacaagt    4860
aaactcgaat tcgcaaaaac tatctttttct aaaggaggtt ttccacaata cgctgataaa    4920
ttaatggaga aatggttttc caaggttttt gaagaatata aaaaagaaaa aattgataat    4980
caaaatatgg aaaatgaagt tgacaaagaa ttagatcaaa ttaaagaaat gtttatacct    5040
ggttcaaatg gaaaacacaa ttccaacact ccacctcatt tgattgaaaa cataaataca    5100
gatgttaaca attcattgga taaccaagat aaatatgata atacattggg aaaacaacga    5160
gttgataaat taatttataa tgaacatgac aaatgggatc attatataaa taagagtat    5220 gtaaaggcat taggcgcatg gatagaaatt cataaaaaat caaataatgt tatgaaaaat    5280
atacttcaag ctgtagaaga tagtaaatac cttttggaaa ataacataga ggatagcata    5340 ttttttttctc gaacttttaa agcaactaaa caatcagctt ttagaaatgt acttaataaa    5400
actctttctc ttggaaaaat gcttttaaga aaacctagtt tcaaagtgga ccatgcattg    5460
tggtttggtg ccactataaa tatgaaaaag ggatttgctt tattagaaaa agttagcgaa    5520
```

-continued

```
ttacataaat taatacgaca tgaagatgaa tcatggttaa ttaatgaggc ctttattgaa    5580
attgtcgatc acataattgc aataagtaca cctagtagca tatcatcccg agcaggttat    5640
ttaagtaatc caggaatgtt tcatattaat ccatttatc atcgcttatc aaatgaggaa     5700
agattaaaag aattcaaca atatatgtgt tatgatcatt gttcgtcatt atggaaaatg     5760
ttatcaacat ttgcattaca tcatttaaaa aatccagata gtttacaaac ttatgaagat    5820 aaatttcta agaattcact aggcaacaaa atgactgaca agatttgt caacaatttt       5880 aaaatgatac tcggaggaga cgctgcatta catttatg ataatttact tcccaaatca      5940 atgaaaaag aattaaagtc tatgaaatat ggtgtatcat tatcattttc attttcacta     6000
aaattagcaa aaatggtttt tggtgaaatg caattacctc atttaagtca catgttttat    6060
gcacaagctc catattttgg ccattttatt ggaaaatggc aaaaggaaag acaacaaggt    6120
agattaaaag aaatttagg agctatgaca ttaggaactt tatcgacata tactgtatta     6180
agtgctatgg ataaacaca acatgctaca gatattggta tgggacctag tactagctgc    6240
tatacatctc ttttacccc accaaaaagt atatgtatac aacaaactgt taaaactgta    6300
ttaactaatt caacattagc atctatgaaa agtgtattct cggttggttt atttgctgca    6360
attacaccat acatgtttgc cccaatggct ggtttagctg tgtggagtgt attaaaatct   6420 cagttaaag tagtaaatag aattgatatg gcacttaagg gagcattaaa aaatatgtgg     6480
aacaaattta tgtcattaaa aggtatccgt agattaaaaa atgtattcaa aaaataaaa    6540 acgataaaga aaaaatgat acaaaaaact gaaagaatt tagccgaaat acaacaaaac    6600
ccagaagctg aacaaaatca taaagcagcc gtcaacgaaa tccataataa tacaagggt     6660 aattatcact atatatctta tgctaaaatc gtagtataa                            6699
```

<210> SEQ ID NO 10
<211> LENGTH: 2232
<212> TYPE: PRT
<213> ORGANISM: Plasmodium yoelii
<220> FEATURE:
<221> NAME/KEY: misc_feature
<222> LOCATION: (1194)..(1194)
<223> OTHER INFORMATION: Xaa can be any naturally occurring amino acid

<400> SEQUENCE: 10

```
Met Leu Lys Ala Thr Ile Gly Ile Ile Leu Phe Ile Cys Val Asn Ile
1               5                   10                  15

Asp Ile Ile Arg Thr Thr Ser Arg Asp Asn Val Val Asn Thr Lys Phe
            20                  25                  30

Val Arg Gln Lys Ser Pro Thr Tyr Asp Pro Asn Lys Lys Gly Asp Val
        35                  40                  45

Ile Phe Tyr Met Pro Glu His Lys Asp Glu Ile His Arg Ala Asn Asn
    50                  55                  60

Lys Ser Ala Asn Ile Asn Leu Lys Asn Asn Pro Pro Arg Asn Ile Asn
65                  70                  75                  80

Ile Gly Tyr Asn Thr Ala Pro Gly Val Asn His Gly Phe Gly Gln Phe
                85                  90                  95

Ser Gly Lys Ser Ser Asn Met Asn Asn Gly Ile Asn Thr Tyr Lys Asn
            100                 105                 110

Gln Pro Lys His Phe Gln Ser Met Asn Tyr Gln Lys Asn Gly Pro Phe
        115                 120                 125

Gly Asn Lys Leu Glu Gln Met Asn Ile Pro Ala Asn Leu Tyr Asn Asn
    130                 135                 140
```

```
Lys Asn Asn Ser Tyr Tyr Ser Gly Ser Asn Asn Gly Asn Asn Asn Ser
145                 150                 155                 160

Tyr Gly Leu His Gly Asn Ile Tyr Asp Lys Ile Asn Ser Ser Val Tyr
                165                 170                 175

Asn Asn Ser Lys Tyr Asn Asn Ser Asn Phe Asn Thr Asp Lys Asn Asn
            180                 185                 190

Asn Asp Asn Glu Asn Asn Lys Thr Tyr Lys Ser Tyr Leu Asn Leu Tyr
            195                 200                 205

Val Ser Asp Asn Lys Ile Ser Pro Ile Gly Asn Asn Gly Arg Pro Gly
        210                 215                 220

His Leu Ile Ser His Phe Asn Asn Pro Asn Gln Lys Leu Glu Phe Leu
225                 230                 235                 240

His Gly Phe Asp Gly Leu Phe Asn Gln Asn Ile Pro Gly Met Asn His
                245                 250                 255

Lys Gly Asn Tyr Gly Phe Asn Gly Val Asn Ile Lys Gly Gln Gly Lys
            260                 265                 270

Asn Glu Lys Phe Asp Asn Tyr Gly Gln Asn Leu Gly Leu Asn Lys Thr
            275                 280                 285

Asn Glu Tyr Gln Gln Met Ile Asn Gly Asn Asn Met Gly Ser Asp His
        290                 295                 300

Ile Tyr Glu Ser Pro Asn Phe Val Asn Gly Asn Asn Met Gly Ser Asp
305                 310                 315                 320

Asn Ala Gly Glu Tyr Gln Arg Leu Val Asn Gly Asn Asn Met Gly Ser
                325                 330                 335

Asp His Ile Tyr Glu Ser Pro Asn Phe Val Asn Gly Asn Asn Met Gly
            340                 345                 350

Ser Asp Asn Ala Gly Glu Ser Gln Arg Leu Val Asn Gly Asn Asn Met
        355                 360                 365

Gly Ser Asp Asn Ala Gly Glu Ser Pro Lys Leu Val Asn Gly Asn Asn
        370                 375                 380

Met Gly Ser Asp Asn Ala Gly Glu Ser Pro Lys Leu Val Asn Gly Asn
385                 390                 395                 400

Asn Met Gly Ser Asp Asn Ala Gly Glu Ser Gln Arg Leu Val Asn Gly
            405                 410                 415

Asn Asn Met Gly Ser Asp Asn Ala Gly Glu Ser Pro Lys Leu Val Asn
            420                 425                 430

Gly Asn Asn Met Gly Ser Asp Asn Ala Gly Glu Ser Gln Arg Leu Val
        435                 440                 445

Asn Gly Asn Asn Met Gly Ser Asp Asn Ser Gly Glu Tyr Gln Arg Leu
    450                 455                 460

Val Asn Gly Asn Asn Met Gly Ser Asp Asn Ser Gly Glu Tyr Gln Arg
465                 470                 475                 480

Leu Val Asn Gly Asn Asn Met Gly Ser Asp His Ile Tyr Glu Ser Pro
                485                 490                 495

Asn Phe Val Asn Gly Asn Asn Met Gly Ser Asp Asn Ala Gly Glu Tyr
            500                 505                 510

Gln Arg Leu Ile Asn Gly Asn Asn Met Gly Ser Asp Asn Ala Gly Glu
        515                 520                 525

Tyr Gln Arg Leu Ile Asn Gly Asn Asn Met Gly Ser Asp His Ile Tyr
        530                 535                 540

Glu Ser Pro Asn Phe Val Asn Gly Asn Asn Met Gly Ser Asp Asn Ala
545                 550                 555                 560

Gly Glu Tyr Gln Arg Leu Ile Asn Gly Asn Asn Met Gly Ser Asp Asn
```

565                 570                 575
Ala Gly Glu Tyr Gln Arg Leu Ile Asn Gly Asn Asn Met Gly Ser Asp
            580                 585                 590

His Ile Tyr Glu Ser Pro Asn Phe Val Asn Gly Asn Asn Met Gly Ser
        595                 600                 605

Asp Asn Ala Gly Glu Tyr Gln Arg Leu Val Asn Gly Asn Asn Met Gly
    610                 615                 620

Ser Asp Asn Ala Gly Glu Tyr Gln Arg Leu Val Asn Gly Asn Asn Met
625                 630                 635                 640

Gly Ser Asp His Ile Tyr Glu Ser Pro Asn Leu Val Asn Gly Asn Asn
            645                 650                 655

Met Gly Ser Asp Asn Ser Gly Glu Tyr Gln Arg Leu Val Asn Gly Asn
        660                 665                 670

Asn Met Gly Ser Asp Asn Ala Gly Glu Tyr Gln Arg Leu Val Asn Gly
    675                 680                 685

Asn Asn Met Gly Ser Asp His Ile Tyr Glu Ser Pro Asn Leu Val Asn
690                 695                 700

Gly Asn Asn Met Gly Ser Asp Asn Ser Gly Glu Tyr Gln Arg Leu Val
705                 710                 715                 720

Asn Gly Asn Asn Met Gly Ser Asp Asp Ser Gly Glu Tyr Gln Lys Leu
            725                 730                 735

Val Asn Gly Asn Asn Gly Val Ile Pro Asn Phe Thr Gly Asn Asp Gln
        740                 745                 750

Glu Ile Phe Lys Asn Ile Arg Gly Leu Arg Pro Val Asn His Glu Glu
    755                 760                 765

Leu Tyr Lys Asn Lys Met Asn Pro Leu Ile Tyr Asn Ala His Gly Met
770                 775                 780

Gln Ser Gly Asn Lys Asn Gly Ala Pro Asn Ser Thr Ser Asp Tyr Val
785                 790                 795                 800

Ser Asp Tyr Asn Ser Asp Ser Asp Thr Asp Ser Asp Ser Asp Ser Asp
            805                 810                 815

Ser Asp Leu Asp Tyr Asp Ser Glu Ser Asn Glu Ser Asn Val Tyr Lys
        820                 825                 830

Ile Lys Thr Asn Lys Leu Glu Asn Asp Asn Lys Asp Gly Asn Gly Asn
    835                 840                 845

Val Asn Asp Ala Asn Tyr Tyr Lys Asn Gln Ile Asp Ile Ala Asn Lys
850                 855                 860

Asn His Gly Asn Arg Tyr Asn Ser Glu Asn Asp Tyr Gly Asp Ser Met
865                 870                 875                 880

His Ser Asp Ser Ala Leu Ser Tyr Glu Arg Asp Leu Ser Ser Gly Asn
            885                 890                 895

Arg His Val Lys Glu Gly Ser Asn Asp Glu Ile Asn Ile Phe Tyr Arg
        900                 905                 910

Asp Asn Ala Gln Asp Arg Glu Thr Lys Glu Lys Leu Met Asn Ser Ser
    915                 920                 925

Glu Ser Asp Lys Asp Val Glu Asn Pro Leu Asn Ile Thr Ile Pro Glu
930                 935                 940

Glu Asn Val Asn Tyr His Phe Ser Asn Tyr Met Asn Phe Asp Lys Lys
945                 950                 955                 960

Asn Ile Leu Thr Ser Asn Glu Glu Leu Leu Lys Met Ile Gly Pro
            965                 970                 975

Asp Phe Ser Lys Glu Val Ser Asn Tyr Cys Ser Lys Lys Ser Ile Phe
        980                 985                 990

-continued

```
Pro Ser Asn Gly Lys Tyr Leu Asp Val Ser Phe Glu Tyr Ser Lys Glu
        995                 1000                1005

Leu Gly Lys Leu Arg Glu Lys Met Met Ser Gly Leu Phe Lys Lys
    1010                1015                1020

Lys Gly Lys Leu Val Thr Lys Glu Asn Asn Ile Leu Lys Gln Ile
    1025                1030                1035

Glu Asn Ser Leu Lys Met Asp Tyr Leu Glu Arg Gln Gln Gly Tyr
    1040                1045                1050

Val Asn Tyr Gly Ser Lys Ser Asn Glu Leu Lys Asn Asp Glu Glu
    1055                1060                1065

Ser Met Leu Ser Asn Glu Tyr Asn Lys Leu Leu Glu Glu Tyr Ile
    1070                1075                1080

Cys His Ile Leu Ser Asn Asn Pro Gly Lys Thr Gln Phe Glu Lys
    1085                1090                1095

Leu Tyr Tyr His Asn Leu Ala Leu Gly Glu Ile Met Lys Pro Ile
    1100                1105                1110

Lys Thr Lys Tyr Lys Asn Ala Ala Thr Leu Ser Ile Ala Leu Asn
    1115                1120                1125

Tyr Glu Ile Tyr Ile Val Ser Ser Ser Asn Ile Tyr Leu Phe Gly
    1130                1135                1140

His Met Leu Leu Leu Ser Leu Ala Tyr Leu Ser Tyr Asn Ser Tyr
    1145                1150                1155

Phe Thr Lys Gly Thr Lys Ser Phe Tyr Ser Met Glu Thr Met Leu
    1160                1165                1170

Leu Ala Asn Ser Asp Tyr Ser Phe Phe Met Tyr Asn Glu Met Cys
    1175                1180                1185

Asn Val Tyr Tyr Arg Xaa Asn Lys Ser Phe Lys Lys Asp Leu Thr
    1190                1195                1200

Phe Ile Pro Ile Glu Leu Arg Pro Gly Arg Tyr Thr Thr Tyr Val
    1205                1210                1215

Gly Glu Arg Lys Ile Ile Cys Asn Thr Leu Glu Leu Ile Leu Asn
    1220                1225                1230

Ala Ile Ser Leu Ile Asn Ile Asn Glu Ile Tyr Asn Val Phe His
    1235                1240                1245

Lys Asn Asn Val Tyr Gly Tyr Glu Asn Ser Val Ser Phe Ser Asn
    1250                1255                1260

Asn Ala Ile Arg Val Phe Ser Gln Val Cys Pro Arg Asn Met Glu
    1265                1270                1275

Lys Asn Ile Ile Asn Cys Ser Phe Glu Lys Ser Thr Leu Tyr Lys
    1280                1285                1290

Ala Asn Ala Pro Glu Asp Thr Asn Gln Asn Glu Tyr Gln Arg Gln
    1295                1300                1305

Asn Gln Ile Lys Asn Gln Asn Glu Leu Lys Lys Ala Phe Asp Leu
    1310                1315                1320

Leu Asn Thr Phe Ser Glu Ile Glu Ser Phe Ser Asn Asn Asn Tyr
    1325                1330                1335

Gln Asn Ser Tyr Tyr Ile Lys Leu Ile Met Glu Gln Asn Leu Tyr
    1340                1345                1350

Thr Asp Phe Tyr Lys Tyr Leu Phe Trp Tyr Asp Asn Arg Glu Leu
    1355                1360                1365

Ile Lys Thr His Glu Ile Asn Gly Lys Lys Asn Thr Lys Lys Thr
    1370                1375                1380
```

-continued

| | | | | | | | | | | | | |
|---|---|---|---|---|---|---|---|---|---|---|---|---|
| Ser | Asn | Tyr | Ile | Tyr | Asp | Gln | Tyr | Ile | Lys | Thr | Asn | Arg | Leu | Leu |
| | 1385 | | | | 1390 | | | | 1395 | | | |

Ser Asn Tyr Ile Tyr Asp Gln Tyr Ile Lys Thr Asn Arg Leu Leu
        1385                1390                1395

Glu Lys Lys Phe Asn Val Leu Ser Lys His Asn Leu Lys Ser Lys
        1400                1405                1410

Gly Leu Leu Ala Phe His Ser Leu Ile Asp Arg Tyr Ser Glu Phe
        1415                1420                1425

Val Lys Asn Lys Lys Ile Arg Asn Leu Tyr Leu Lys Phe Val Ser
        1430                1435                1440

Tyr Ala Arg His Phe Leu Phe Met Asn Asn Thr Met Lys Ser Leu
        1445                1450                1455

Asn Lys Ser Asp Leu Asp Phe Met Lys Met Ile Phe Glu Glu Leu
        1460                1465                1470

Gln Asn Glu Thr Lys Val Pro Leu Lys Leu Ile Val Arg Gly Asn
        1475                1480                1485

Tyr Met Lys Ser Met Asn Asp Ile Ala Lys Lys Glu Asn Leu Phe
        1490                1495                1500

Phe Ile Asn Leu Phe Ile Leu Ser Leu Phe Ser Asn Lys Asn Pro
        1505                1510                1515

Val Lys Asn Phe Tyr Asn Gly Lys Arg Glu Met Leu Lys Ala Ser
        1520                1525                1530

Leu Ser Glu Lys Phe Ala Thr Ser Thr Ser Ala Phe Ile Pro His
        1535                1540                1545

Lys Leu Arg Arg Ile Val Val Gly Met Lys Lys Gly Phe Leu Lys
        1550                1555                1560

Arg Lys Leu Leu Lys Thr Leu Met Lys Asn Arg Leu Leu Gln His
        1565                1570                1575

Ile Pro Ile Asp Leu Leu Glu Asn Ile Met Thr Thr Phe Arg Phe
        1580                1585                1590

Thr Thr His Ala Ile Ala Thr Ser Glu Leu Ala Gln Asn Ala His
        1595                1600                1605

Arg Thr Ser Lys Tyr Leu Asn Ser Asn Asn Thr Ser Lys Leu Glu
        1610                1615                1620

Phe Ala Lys Thr Ile Phe Ser Lys Gly Gly Phe Pro Gln Tyr Ala
        1625                1630                1635

Asp Lys Leu Met Glu Lys Trp Phe Ser Lys Gly Phe Glu Glu Tyr
        1640                1645                1650

Lys Lys Glu Lys Ile Asp Asn Gln Asn Met Glu Asn Glu Val Asp
        1655                1660                1665

Lys Glu Leu Asp Gln Ile Lys Glu Met Phe Ile Pro Gly Ser Asn
        1670                1675                1680

Gly Lys His Asn Ser Asn Thr Pro Pro His Leu Ile Glu Asn Ile
        1685                1690                1695

Asn Thr Asp Val Asn Asn Ser Leu Asp Asn Gln Asp Lys Tyr Asp
        1700                1705                1710

Asn Thr Leu Gly Lys Gln Arg Val Asp Lys Leu Ile Tyr Asn Glu
        1715                1720                1725

His Asp Lys Trp Asp His Tyr Ile Asn Lys Glu Tyr Val Lys Ala
        1730                1735                1740

Leu Gly Ala Trp Ile Glu Ile His Lys Lys Ser Asn Asn Val Met
        1745                1750                1755

Glu Asn Ile Leu Gln Ala Val Glu Asp Ser Lys Tyr Leu Leu Glu
        1760                1765                1770

Asn Asn Ile Glu Asp Ser Ile Phe Phe Ser Arg Thr Phe Lys Ala

-continued

```
            1775                1780                1785
Thr Lys Gln Ser Ala Phe Arg Asn Val Leu Asn Lys Thr Leu Ser
        1790                1795                1800
Leu Gly Lys Met Leu Leu Arg Lys Pro Ser Phe Lys Val Asp His
        1805                1810                1815
Ala Leu Trp Phe Gly Ala Thr Ile Asn Met Lys Lys Gly Phe Ala
        1820                1825                1830
Leu Leu Glu Lys Val Ser Glu Leu His Lys Leu Ile Arg His Glu
        1835                1840                1845
Asp Glu Ser Trp Leu Ile Asn Glu Ala Phe Ile Glu Ile Val Asp
        1850                1855                1860
His Ile Ile Ala Ile Ser Thr Pro Ser Ser Ile Ser Ser Arg Ala
        1865                1870                1875
Gly Tyr Leu Ser Asn Pro Gly Met Phe His Ile Asn Pro Phe Tyr
        1880                1885                1890
His Arg Leu Ser Asn Glu Glu Arg Leu Lys Glu Leu Gln Gln Tyr
        1895                1900                1905
Met Cys Tyr Asp His Cys Ser Ser Leu Trp Lys Met Leu Ser Thr
        1910                1915                1920
Phe Ala Leu His His Leu Lys Asn Pro Asp Ser Leu Gln Thr Tyr
        1925                1930                1935
Glu Asp Lys Phe Ser Lys Asn Ser Leu Gly Asn Lys Met Thr Asp
        1940                1945                1950
Lys Asp Phe Val Asn Asn Phe Lys Met Ile Leu Gly Gly Asp Ala
        1955                1960                1965
Ala Leu His Phe Tyr Asp Asn Leu Leu Pro Lys Ser Met Lys Lys
        1970                1975                1980
Glu Leu Lys Ser Met Lys Tyr Gly Val Ser Leu Ser Phe Ser Phe
        1985                1990                1995
Ser Leu Lys Leu Ala Lys Met Val Phe Gly Glu Met Gln Leu Pro
        2000                2005                2010
His Leu Ser His Met Phe Tyr Ala Gln Ala Pro Tyr Phe Gly His
        2015                2020                2025
Phe Ile Gly Lys Trp Gln Lys Glu Arg Gln Gln Gly Arg Leu Lys
        2030                2035                2040
Glu Ile Leu Gly Ala Met Thr Leu Gly Thr Leu Ser Thr Tyr Thr
        2045                2050                2055
Val Leu Ser Ala Met Asp Ile Thr Gln His Ala Thr Asp Ile Gly
        2060                2065                2070
Met Gly Pro Ser Thr Ser Cys Tyr Thr Ser Leu Leu Pro Pro Pro
        2075                2080                2085
Lys Ser Ile Cys Ile Gln Gln Thr Val Lys Thr Val Leu Thr Asn
        2090                2095                2100
Ser Thr Leu Ala Ser Met Lys Ser Val Phe Ser Val Gly Leu Phe
        2105                2110                2115
Ala Ala Ile Thr Pro Tyr Met Phe Ala Pro Met Ala Gly Leu Ala
        2120                2125                2130
Val Trp Ser Val Leu Lys Ser Gln Phe Lys Val Val Asn Arg Ile
        2135                2140                2145
Asp Met Ala Leu Lys Gly Ala Leu Lys Asn Met Trp Asn Lys Phe
        2150                2155                2160
Met Ser Leu Lys Gly Ile Arg Arg Leu Lys Asn Val Phe Lys Lys
        2165                2170                2175
```

-continued

Ile Lys Thr Ile Lys Lys Lys Met Ile Gln Lys Thr Glu Lys Asn
    2180                2185                2190

Leu Ala Glu Ile Gln Gln Asn Pro Glu Ala Glu Gln Asn His Lys
    2195                2200                2205

Ala Ala Val Asn Glu Ile His Asn Asn Thr Arg Gly Asn Tyr His
    2210                2215                2220

Tyr Ile Ser Tyr Ala Lys Ile Val Val
    2225                2230

<210> SEQ ID NO 11
<211> LENGTH: 47
<212> TYPE: PRT
<213> ORGANISM: Plasmodium berghei

<400> SEQUENCE: 11

Asp Ile Thr Gln His Ala Thr Asp Ile Gly Met Gly Pro Ser Thr Ser
1               5                   10                  15

Cys Tyr Thr Ser Leu Val Pro Pro Lys Ser Ile Cys Ile Gln Gln
            20                  25                  30

Thr Val Lys Ala Val Leu Thr Asn Ser Thr Leu Ala Ser Met Lys
        35                  40                  45

<210> SEQ ID NO 12
<211> LENGTH: 47
<212> TYPE: PRT
<213> ORGANISM: Plasmodium yoelli

<400> SEQUENCE: 12

Asp Ile Thr Gln His Ala Thr Asp Ile Gly Met Gly Pro Ser Thr Ser
1               5                   10                  15

Cys Tyr Thr Ser Leu Leu Pro Pro Lys Ser Ile Cys Ile Gln Gln
            20                  25                  30

Thr Val Lys Thr Val Leu Thr Asn Ser Thr Leu Ala Ser Met Lys
        35                  40                  45

<210> SEQ ID NO 13
<211> LENGTH: 47
<212> TYPE: PRT
<213> ORGANISM: Plasmodium knowlesi

<400> SEQUENCE: 13

Asp Ile Thr Gln His Ala Ser Asp Ile Gly Met Gly Pro Val Thr Ser
1               5                   10                  15

Cys Tyr Thr Ser Thr Ile Pro Pro Lys Gln Val Cys Ile Gln Gln
            20                  25                  30

Ala Val Lys Val Thr Leu Thr Asn Ser Thr Gln Ala Cys Met Lys
        35                  40                  45

<210> SEQ ID NO 14
<211> LENGTH: 47
<212> TYPE: PRT
<213> ORGANISM: Plasmodium vivax

<400> SEQUENCE: 14

Asp Ile Ser Gln His Ala Thr Asp Ile Gly Met Gly Pro Ala Thr Ser
1               5                   10                  15

Cys Tyr Thr Ser Thr Ile Pro Pro Lys Gln Val Cys Ile Gln Gln
            20                  25                  30

Ala Val Lys Ala Thr Leu Thr Ser Ser Thr Gln Ala Cys Met Lys

<210> SEQ ID NO 15
<211> LENGTH: 47
<212> TYPE: PRT
<213> ORGANISM: Plasmodium falciparum

<400> SEQUENCE: 15

Asp Ile Thr Gln Gln Ala Lys Asp Ile Gly Ala Gly Pro Val Ala Ser
1               5                   10                  15

Cys Phe Thr Thr Arg Met Ser Pro Gln Gln Ile Cys Leu Asn Ser
            20                  25                  30

Val Val Asn Thr Ala Leu Ser Thr Ser Thr Gln Ser Ala Met Lys
        35                  40                  45

<210> SEQ ID NO 16
<211> LENGTH: 45
<212> TYPE: PRT
<213> ORGANISM: Toxoplasma gondii

<400> SEQUENCE: 16

Asp Ile Val Gln His Met Glu Asp Ile Gly Gly Ala Pro Pro Val Ser
1               5                   10                  15

Cys Val Thr Asn Glu Ile Leu Gly Val Thr Cys Ala Pro Gln Ala Ile
            20                  25                  30

Ala Lys Ala Thr Thr Ser Ala Ala Arg Val Ala Thr Gln
        35                  40                  45

<210> SEQ ID NO 17
<211> LENGTH: 557
<212> TYPE: PRT
<213> ORGANISM: Plasmodium yoelii

<400> SEQUENCE: 17

Met Lys Glu Ile Tyr Tyr Ile Phe Ile Leu Cys Ser Ile Tyr Leu Ile
1               5                   10                  15

Asn Leu Ser Tyr Cys Ser Glu Gly Pro Asn Gln Val Ile Ser Glu Asp
20 25 30

Gly Asn Ile Asn Tyr Glu Ser Ile Pro Lys Glu Asn Thr Glu Arg Ser
35 40 45

Ile Lys Leu Ile Asn Pro Trp Asp Lys Tyr Met Glu Lys Tyr Asp Ile
50 55 60

Glu Lys Val His Gly Ser Gly Ile Arg Val Asp Leu Gly Glu Asp Ala
65 70 75 80

Arg Val Glu Asn Arg Asp Tyr Arg Ile Pro Ser Gly Lys Cys Pro Val
85 90 95

Ile Gly Lys Gly Ile Thr Ile Gln Asn Ser Glu Val Ser Phe Leu Lys
100 105 110

Pro Val Ala Thr Gly Asp Lys Pro Val Arg Ser Gly Gly Leu Ala Phe
115 120 125

Pro Glu Thr Asp Val His Ile Ser Pro Ile Thr Ile Thr Asn Leu Lys
130 135 140

Thr Met Tyr Lys Asp His Gln Asp Ile Val Asn Leu Asn Asp Met Ser
145 150 155 160

Leu Cys Ala Lys His Thr Ser Leu Tyr Val Pro Gly Lys Asp Ala Thr
165 170 175

Ser Ala Tyr Arg His Pro Val Val Tyr Asp Lys Ser Asn Ser Thr Cys
180 185 190

Tyr Met Leu Tyr Val Ala Ala Gln Glu Asn Met Gly Pro Arg Tyr Cys
            195                 200                 205

Ser Asn Asp Ala Asn Asn Glu Asn Gln Pro Phe Cys Phe Thr Pro Glu
    210                 215                 220

Lys Ile Glu Asn Tyr Lys Asp Leu Ser Tyr Leu Thr Lys Asn Leu Arg
225                 230                 235                 240

Asp Asp Trp Glu Thr Ser Cys Pro Asn Lys Ser Ile Lys Asn Ala Lys
                245                 250                 255

Phe Gly Ile Trp Val Asp Gly Tyr Cys Thr Asp Tyr Gln Lys His Val
                260                 265                 270

Val His Asp Ser Asp Ser Leu Leu Lys Cys Asn Gln Ile Ile Phe Asn
            275                 280                 285

Glu Ser Ala Ser Asp Gln Pro Lys Gln Tyr Glu Arg His Leu Glu Asp
290                 295                 300

Ala Thr Lys Ile Arg Gln Gly Ile Val Glu Arg Asn Gly Lys Leu Ile
305                 310                 315                 320

Gly Glu Ala Leu Leu Pro Ile Gly Ser Tyr Lys Ser Gly Gln Ile Lys
                325                 330                 335

Ser His Gly Lys Gly Tyr Asn Trp Gly Asn Tyr Asp Ser Lys Asn Asn
            340                 345                 350

Lys Cys Tyr Ile Phe Glu Thr Lys Pro Thr Cys Leu Ile Asn Asp Lys
            355                 360                 365

Asn Phe Ile Ala Thr Thr Ala Leu Ser Ser Thr Glu Glu Phe Glu Glu
370                 375                 380

Asn Phe Pro Cys Glu Ile Tyr Lys Asn Lys Ile Ala Glu Glu Ile Lys
385                 390                 395                 400

Val Leu Asn Leu Asn Gln Asn Thr Ser Asn Gly Asn Asn Ser Ile Lys
                405                 410                 415

Phe Pro Arg Ile Phe Ile Ser Thr Asp Lys Asn Ser Leu Asn Cys Pro
            420                 425                 430

Cys Asp Pro Thr Lys Leu Thr Glu Ser Thr Cys Glu Phe Tyr Val Cys
            435                 440                 445

Ser Cys Val Glu Gln Arg Gln Tyr Ile Ala Glu Asn Asn Asp Val Ile
            450                 455                 460

Ile Lys Glu Glu Phe Ile Gly Asp Tyr Glu Asn Pro Lys Gln Lys Leu
465                 470                 475                 480

Leu Ile Ile Ile Val Leu Ile Gly Val Gly Ile Ile Val Ile Leu
                485                 490                 495

Leu Val Ala Tyr Tyr Phe Lys Ser Gly Lys Lys Gly Glu Asn Tyr Asp
                500                 505                 510

Arg Met Gly Gln Ala Asp Asp Tyr Gly Lys Ser Lys Ser Arg Lys Asp
            515                 520                 525

Glu Met Leu Asp Pro Glu Val Ser Phe Trp Gly Glu Asp Lys Arg Ala
530                 535                 540

Ser His Thr Thr Pro Val Leu Met Glu Lys Pro Tyr Tyr
545                 550                 555

<210> SEQ ID NO 18
<211> LENGTH: 50
<212> TYPE: PRT
<213> ORGANISM: Plasmodium falciparum

<400> SEQUENCE: 18

Ser Asn Thr Thr Phe Leu Thr Pro Val Ala Thr Gly Asn Gln Tyr Leu

```
1               5                   10                  15
Lys Asp Gly Gly Phe Ala Phe Pro Pro Thr Glu Pro Leu Met Ser Pro
            20                  25                  30

Thr Leu Asp Glu Met Arg His Phe Tyr Lys Asp Asn Lys Tyr Val Lys
            35                  40                  45

Asn Leu
    50

<210> SEQ ID NO 19
<211> LENGTH: 66
<212> TYPE: PRT
<213> ORGANISM: Plasmodium falciparum

<400> SEQUENCE: 19

Leu Thr Pro Val Ala Thr Gly Asn Gln Tyr Leu Lys Phe Pro Pro Thr
1               5                   10                  15

Glu Pro Leu Met Ser Leu Asp Glu Met Arg His Phe Tyr Lys Asp Asn
            20                  25                  30

Lys Tyr Val Lys Asn Leu Met Ile Pro Asp Asn Asp Lys Asn Ser Asn
            35                  40                  45

Tyr Lys Tyr Tyr Cys Asn Lys Asp Glu Ser Lys Arg Asn Ser Met Phe
    50                  55                  60

Cys Phe
65

<210> SEQ ID NO 20
<211> LENGTH: 66
<212> TYPE: PRT
<213> ORGANISM: Plasmodium falciparum

<400> SEQUENCE: 20

Leu Thr Pro Val Ala Thr Gly Asn Gln Tyr Leu Lys Phe Pro Pro Thr
1               5                   10                  15

Lys Pro Leu Met Ser Leu Asp Asp Met Arg Leu Leu Tyr Lys Asp Asn
            20                  25                  30

Glu Asp Val Lys Asn Leu Met Asn Pro Asp Asn Asp Lys Asn Ser Asn
            35                  40                  45

Tyr Lys Tyr Tyr Cys Asn Lys Asp Glu Ser Lys Arg Asn Ser Met Phe
    50                  55                  60

Cys Phe
65

<210> SEQ ID NO 21
<211> LENGTH: 66
<212> TYPE: PRT
<213> ORGANISM: Plasmodium falciparum

<400> SEQUENCE: 21

Leu Thr Pro Val Ala Thr Glu Asn Gln Asp Leu Lys Phe Pro Pro Thr
1               5                   10                  15

Glu Pro Leu Met Ser Leu Asp Asp Met Arg Arg Phe Tyr Lys Asp Asn
            20                  25                  30

Glu Tyr Val Lys Asn Leu Met Asn Pro Asp Asn Asp Lys Asn Ser Asn
            35                  40                  45

Tyr Lys Tyr Tyr Cys Asn Lys Asp Glu Ser Lys Arg Asn Ser Met Phe
    50                  55                  60

Cys Phe
65
```

-continued

```
<210> SEQ ID NO 22
<211> LENGTH: 66
<212> TYPE: PRT
<213> ORGANISM: Plasmodium falciparum

<400> SEQUENCE: 22

Leu Thr Pro Val Ala Thr Glu Asn Gln Asp Leu Lys Phe Pro Pro Thr
1               5                   10                  15

Glu Pro Leu Ile Ser Leu Asp Gln Met Arg His Leu Tyr Lys Asp Asn
            20                  25                  30

Glu Tyr Val Lys Asn Leu Met Asn Pro Asp Asn Asp Lys Asn Ser Asn
        35                  40                  45

Tyr Lys Tyr Tyr Cys Asn Lys Asp Glu Ser Lys Arg Asn Ser Met Phe
    50                  55                  60

Cys Phe
65

<210> SEQ ID NO 23
<211> LENGTH: 66
<212> TYPE: PRT
<213> ORGANISM: Plasmodium falciparum

<400> SEQUENCE: 23

Leu Lys Pro Val Ala Thr Gly Asn Gln Asp Leu Lys Phe Pro Pro Thr
1               5                   10                  15

Glu Pro Leu Ile Ser Leu Asn Gly Met Arg Asp Phe Tyr Lys Asn Asn
            20                  25                  30

Glu Tyr Val Lys Asn Leu Met Asn Pro Asp Lys Asp Glu Asn Ser Asn
        35                  40                  45

Tyr Lys Tyr Tyr Cys Asn Lys Asp Glu Ser Lys Arg Asn Ser Met Phe
    50                  55                  60

Cys Phe
65

<210> SEQ ID NO 24
<211> LENGTH: 66
<212> TYPE: PRT
<213> ORGANISM: Plasmodium falciparum

<400> SEQUENCE: 24

Leu Lys Pro Val Ala Thr Gly Asn Gln Asp Leu Lys Phe Pro Pro Thr
1               5                   10                  15

Asn Pro Leu Ile Ser Leu Asn Gly Met Arg Asp Phe Tyr Lys Asn Asn
            20                  25                  30

Glu Tyr Val Lys Asn Leu Met Asn Pro Asp Asn Asp Lys Asn Ser Asn
        35                  40                  45

Tyr Lys Tyr Tyr Cys Asn Lys Asp Gln Ser Lys Arg Asn Ser Met Phe
    50                  55                  60

Cys Phe
65

<210> SEQ ID NO 25
<211> LENGTH: 66
<212> TYPE: PRT
<213> ORGANISM: Plasmodium falciparum

<400> SEQUENCE: 25

Leu Lys Pro Val Ala Thr Gly Asn Gln Asp Leu Lys Phe Pro Pro Thr
1               5                   10                  15
```

-continued

Asn Pro Leu Ile Ser Leu Asp His Met Arg Asp Phe Tyr Lys Asn Asn
            20                  25                  30

Glu Tyr Val Lys Asn Leu Met Asn Pro Asp Asn Asp Lys Asn Ser Asn
            35                  40                  45

Tyr Lys Tyr Tyr Cys Asn Lys Asp Glu Ser Lys Arg Asn Ser Met Phe
        50                  55                  60

Cys Phe
65

<210> SEQ ID NO 26
<211> LENGTH: 66
<212> TYPE: PRT
<213> ORGANISM: Plasmodium falciparum

<400> SEQUENCE: 26

Leu Lys Pro Val Ala Thr Gly Asn Gln Asp Leu Lys Phe Pro Pro Thr
1               5                   10                  15

Glu Pro Leu Ile Ser Leu Asp Asp Met Arg Asp Phe Tyr Lys Asn Asn
            20                  25                  30

Glu Tyr Val Lys Asn Leu Met Asn Pro Asp Asn Asp Lys Asn Ser Asn
            35                  40                  45

Tyr Lys Tyr Tyr Cys Asn Lys Asp Gln Ser Lys Arg Asn Ser Met Phe
        50                  55                  60

Cys Phe
65

<210> SEQ ID NO 27
<211> LENGTH: 66
<212> TYPE: PRT
<213> ORGANISM: Plasmodium falciparum

<400> SEQUENCE: 27

Leu Thr Pro Val Ala Thr Glu Asn Gln Asp Leu Lys Phe Pro Pro Thr
1               5                   10                  15

Lys Pro Leu Met Ser Leu Asp Gln Met Arg Asp Phe Tyr Lys Asn Asn
            20                  25                  30

Glu Tyr Val Lys Asn Leu Met Asn Pro Asp Asn Asp Glu Asn Ser Asn
            35                  40                  45

Tyr Lys Tyr Tyr Cys Asn Lys Asp Gln Ser Lys Arg Asn Ser Met Phe
        50                  55                  60

Cys Phe
65

<210> SEQ ID NO 28
<211> LENGTH: 48
<212> TYPE: PRT
<213> ORGANISM: Plasmodium yoelii

<400> SEQUENCE: 28

Cys Asp Ile Thr Gln His Ala Thr Asp Ile Gly Met Gly Pro Ser Thr
1               5                   10                  15

Ser Cys Tyr Thr Ser Leu Leu Pro Pro Pro Lys Ser Ile Cys Ile Gln
            20                  25                  30

Gln Thr Val Lys Thr Val Leu Thr Asn Ser Thr Leu Ala Ser Met Lys
            35                  40                  45

<210> SEQ ID NO 29
<211> LENGTH: 47
<212> TYPE: PRT

<213> ORGANISM: Plasmodium yoelii

<400> SEQUENCE: 29

Asp Ile Thr Gln His Ala Thr Asp Ile Gly Met Gly Pro Ser Thr Ser
1               5                   10                  15

Cys Tyr Thr Ser Leu Leu Pro Pro Lys Ser Ile Cys Ile Gln Gln
            20                  25                  30

Thr Val Lys Thr Val Leu Thr Asn Ser Thr Leu Ala Ser Met Lys
        35                  40                  45

<210> SEQ ID NO 30
<211> LENGTH: 48
<212> TYPE: PRT
<213> ORGANISM: Plasmodium falciparum

<400> SEQUENCE: 30

Cys Asp Ile Thr Gln Gln Ala Lys Asp Ile Gly Ala Gly Pro Val Ala
1               5                   10                  15

Ser Cys Phe Thr Thr Arg Met Ser Pro Pro Gln Gln Ile Cys Leu Asn
            20                  25                  30

Ser Val Val Asn Thr Ala Leu Ser Thr Ser Thr Gln Ser Ala Met Lys
        35                  40                  45

<210> SEQ ID NO 31
<211> LENGTH: 47
<212> TYPE: PRT
<213> ORGANISM: Plasmodium falciparum

<400> SEQUENCE: 31

Asp Ile Thr Gln Gln Ala Lys Asp Ile Gly Ala Gly Pro Val Ala Ser
1               5                   10                  15

Cys Phe Thr Thr Arg Met Ser Pro Pro Gln Gln Ile Cys Leu Asn Ser
            20                  25                  30

Val Val Asn Thr Ala Leu Ser Thr Ser Thr Gln Ser Ala Met Lys
        35                  40                  45

<210> SEQ ID NO 32
<211> LENGTH: 16
<212> TYPE: PRT
<213> ORGANISM: Plasmodium falciparum

<400> SEQUENCE: 32

Leu Gly Glu Asp Ala Glu Val Ala Gly Thr Gln Tyr Arg Leu Pro Ser
1               5                   10                  15

<210> SEQ ID NO 33
<211> LENGTH: 24
<212> TYPE: PRT
<213> ORGANISM: Plasmodium falciparum

<400> SEQUENCE: 33

Glu Asn Ser Asn Thr Thr Phe Leu Thr Pro Val Ala Thr Gly Asn Gln
1               5                   10                  15

Tyr Leu Lys Asp Gly Gly Phe Ala
            20

<210> SEQ ID NO 34
<211> LENGTH: 16
<212> TYPE: PRT
<213> ORGANISM: Plasmodium falciparum

<400> SEQUENCE: 34

```
Thr Leu Asp Glu Met Arg His Phe Tyr Lys Asp Asn Lys Tyr Val Lys
1               5                   10                  15

<210> SEQ ID NO 35
<211> LENGTH: 14
<212> TYPE: PRT
<213> ORGANISM: Plasmodium falciparum

<400> SEQUENCE: 35

Gly Asn Met Ile Pro Asp Asn Asp Lys Asn Ser Asn Tyr Lys
1               5                   10

<210> SEQ ID NO 36
<211> LENGTH: 17
<212> TYPE: PRT
<213> ORGANISM: Plasmodium falciparum

<400> SEQUENCE: 36

Arg Tyr Cys Asn Lys Asp Glu Ser Lys Arg Asn Ser Met Phe Cys Phe
1               5                   10                  15

Arg

<210> SEQ ID NO 37
<211> LENGTH: 47
<212> TYPE: PRT
<213> ORGANISM: Plasmodium falciparum

<400> SEQUENCE: 37

Ser Asp Gln Pro Lys Gln Tyr Glu Gln His Leu Thr Asp Tyr Glu Lys
1               5                   10                  15

Ile Lys Glu Gly Phe Lys Asn Lys Asn Ala Ser Met Ile Lys Ser Ala
            20                  25                  30

Phe Leu Pro Thr Gly Ala Phe Lys Ala Asp Arg Tyr Lys Ser His
        35                  40                  45

<210> SEQ ID NO 38
<211> LENGTH: 58
<212> TYPE: PRT
<213> ORGANISM: Plasmodium falciparum

<400> SEQUENCE: 38

Ser Pro Met Thr Leu Asp Glu Met Arg His Phe Tyr Lys Asp Asn Lys
1               5                   10                  15

Tyr Val Lys Asn Leu Asp Glu Leu Thr Leu Cys Ser Arg His Ala Gly
            20                  25                  30

Asn Met Ile Pro Asp Asn Asp Lys Asn Ser Asn Tyr Lys Tyr Pro Ala
        35                  40                  45

Val Tyr Asp Asp Lys Asp Lys Lys Cys His
    50                  55

<210> SEQ ID NO 39
<211> LENGTH: 50
<212> TYPE: PRT
<213> ORGANISM: Plasmodium falciparum

<400> SEQUENCE: 39

Ser Asn Thr Thr Phe Leu Thr Pro Val Ala Thr Gly Asn Gln Tyr Leu
1               5                   10                  15

Lys Asp Gly Gly Phe Ala Phe Pro Pro Thr Glu Pro Leu Met Ser Pro
            20                  25                  30
```

-continued

```
Thr Leu Asp Glu Met Arg His Phe Tyr Lys Asp Asn Lys Tyr Val Lys
        35                  40                  45
Asn Leu
    50
```